US011963533B2

(12) United States Patent
Jin et al.

(10) Patent No.: US 11,963,533 B2
(45) Date of Patent: Apr. 23, 2024

(54) **COMPOSITIONS AND METHODS FOR TREATING *LIBERIBACTER* DISEASES AND OTHER BACTERIAL DISEASES**

(71) Applicant: The Regents of the University of California, Oakland, CA (US)

(72) Inventors: Hailing Jin, Oakland, CA (US); Chien Yu Huang, Oakland, CA (US)

(73) Assignee: The Regents of The University of California, Oakland, CA (US)

(*) Notice: Subject to any disclaimer, the term of this patent is extended or adjusted under 35 U.S.C. 154(b) by 121 days.

(21) Appl. No.: 16/757,284

(22) PCT Filed: Oct. 23, 2018

(86) PCT No.: PCT/US2018/057153
§ 371 (c)(1),
(2) Date: Apr. 17, 2020

(87) PCT Pub. No.: WO2019/084040
PCT Pub. Date: May 2, 2019

(65) Prior Publication Data

US 2021/0186028 A1 Jun. 24, 2021

Related U.S. Application Data

(60) Provisional application No. 62/677,817, filed on May 30, 2018, provisional application No. 62/575,993, filed on Oct. 23, 2017.

(51) Int. Cl.
*C12N 15/82* (2006.01)
*A01N 63/50* (2020.01)
*C07K 14/415* (2006.01)

(52) U.S. Cl.
CPC ............ *A01N 63/50* (2020.01); *C07K 14/415* (2013.01); *C12N 15/8281* (2013.01)

(58) Field of Classification Search
None
See application file for complete search history.

(56) References Cited

U.S. PATENT DOCUMENTS 10,285,333 B2 5/2019 Mirkov et al.
2016/0186201 A1 6/2016 Xoconostle Cázares et al.

FOREIGN PATENT DOCUMENTS

CN 104244705 A 12/2014
CN 106337059 A 1/2017

OTHER PUBLICATIONS

UniProtKB accession No. A0A067G105_CITSI. (Year: 2015).*
Genbank accession KDO72075.1 (Year: 2014).*
NCBI Reference Sequence: XP_006355724.1 (Year: 2016).*
Genbank locus KDO72074.1 (Year: 2014).*
Genbank4 (GenBank: ESR37559.1) (Year: 2015).*
Gomes et al. "Gene expression and functional analysis of soybean genes with diurnal oscillation during drought stress". Plant & Animal Genome XXIII. San Diego, USA. (Year: 2015).*
Anonymous; "CISIN_1G033887mg—Stress-response A/B barrel domain-containing protein—*Citrus sinensis* (Sweet orange)—CISIN_1G03887mg gene & protein"; https://www.uniprot.org/uniprot/A0A067G105; Sep. 3, 2014.
Supplemental Partial European Search Report in EP dated Mar. 27, 2019.
Anonymous; "UniProtKB/TrEMBL—Full=Stress-response A/B barrel domain-containing protein"; Sep. 3, 2014.
Park et al., "Characterization of a heat-stable protein with antimicrobial activity from *Arabidopsis thaliana*," Biochemical and Biophysical Research Communications, Sep. 11, 2007, pp . 562-567, 362(3), Elsevier, Amsterdam, Netherlands.
Extended European Search Report in EP 18870019, dated Sep. 24, 2021.
International Search Report in PCT/US2018/057153, dated Mar. 27, 2019.
UniProtKB accession nmber A0A067G105_CITSI, Dec. 9, 2015 [online], retrieved from the internet at https://www.uniprot.org/uniprot/A0A067G105.txt, whole document.
Hao et al., "Transgenic Expression of Antimicrobial Peptide D2A21 Confers Resistance to Diseases Incited by *Pseudomonas syringae* pv. Tabaci and Xanthomonas Citri, but Not Candidatus Liberibacter Asiaticus," PLOS One, 12(10), Oct. 19, 2017, pp. 1-17.
Kou et al., "Molecular analyses of the rice tubby-like protein gene family and their response to bacterial infection," Plant Cell Rep., 28(1), Sep. 26, 2008, pp. 113-121.
Xu et al., "Genome-Wide Identification and Expression Analysis of the Tubby-Like Protein Family in the Malus domestica Genome," Front Plant Sci., Nov. 14, vol. 7, Nov. 14, 2016, pp. 1-12.
"Stress-Response A/B Barrel Domain-Containing Protein At5g22580 [Citrus Clementina]", NCBI Reference Sequence: XP_006424319.1, Feb. 26, 2018, 1 page.

* cited by examiner

*Primary Examiner* — Matthew R Keogh
*Assistant Examiner* — David R Byrnes
(74) *Attorney, Agent, or Firm* — Kilpatrick Townsend & Stockton LLP

(57) ABSTRACT

The disclosure provides stable antimicrobial (e.g., antibacterial or antifungal or both) peptides (SAMPs) that may be used in methods of preventing or treating a bacterial disease (e.g., a *Liberibacter* disease, such as *citrus* greening disease (also called Huanglongbing (HLB)) or potato Zebra Chip disease, and other bacterial diseases such as those caused by *Agrobacterium tumefaciens* (also known as *Rhizobium radiobacter*) and *Pseudomonas syringae*) in plants (e.g., *citrus* plants or potato plants). SAMPs disclosed herein may be heat stable, as well as stable in plant extracts and/or in plant lysates (e.g., *citrus* lysates).

24 Claims, 14 Drawing Sheets

Specification includes a Sequence Listing.

SAMP treatment on HLB-positive citrus trees 5 weeks post treatment

*C. Las* titer measurement

SAMP treatment on C.Lso-positive potato plants

Mock SAMP 3 μM SAMP 10 μM

Biomass of tomato plants pre-treated with SAMP

***Pt-* *Poncirus trifoliate***

***Ma-* *Microcitrus australasica* (Australian finger lime)**

***Eg-* *Eremocitrus glauca* (Australian desert lime)**

*L. crescens* incubated with pre-treated SAMP or buffer only (Mock) for 2 hours

*Pseudomonas syringae pv DC3000*

*Agrobacterium tumefaciens*

COMPOSITIONS AND METHODS FOR TREATING *LIBERIBACTER* DISEASES AND OTHER BACTERIAL DISEASES

BACKGROUND

Huanglongbing (HLB), also called *citrus* greening, is one of the most devastating *citrus* plant diseases. This *citrus* plant disease causes multibillion-dollar loss annually in the United States alone. According to research from the Institute of Food and Agricultural Sciences at the University of Florida, Florida has lost approximately 162,200 acres of *citrus* plants and 7,513 jobs since detection of HLB in Florida in 2005. The most recent forecasts from the National Association of Academies of Science predicted that *citrus* production from 2016 to 2017 is approximately 70% lower than peak production levels from 1997 to 1998. Moreover, HLB also spreads rapidly in Texas and California. Recently, more than 400 confirmed cases of HLB-infected trees have been reported in southern California. HLB is caused by the phloem-limited Gram-negative bacteria of the *Liberibacter* species, e.g., *Candidatus Liberibacter* species (e.g., *Candidatus Liberibacter asiaticus* (*Ca. L. asiaticus*)), which is transmitted by insects of the Psyllidae family, e.g., Asian *citrus* psyllids (ACP).

Another important disease cause by the *Liberibacter* species is Potato Zebra Chip (ZC) disease, also called Potato Zebra complex disease. ZC disease is associated with *Candidatus Liberibacter solanacearum* (*Ca. L. solanacearum*), which is transmitted by potato psyllids (e.g., *Bactericera cockerelli*). ZC disease reached epidemic level in northern Texas in 2006 and has spread to Arizona, California, Colorado, Idaho, Oregon, Kansas, Nebraska, and New Mexico. ZC disease has caused millions of dollars loss to the potato industry in the southwestern United States, particularly Texas. In addition to potato, other solanaceous crops, including tomato, eggplant and pepper, can also be infected. There exists a need in the art for innovative compositions and methods to treat diseases in plants caused by *Liberibacter* species (e.g., *Candidatus Liberibacter* species).

SUMMARY

The disclosure provides stable antimicrobial (e.g., antibacterial or antifungal or both) peptides (SAMPs) that may be used in methods of preventing or treating bacterial diseases, such as those caused by Gram-negative bacteria, e.g., a *Liberibacter* disease (e.g., *citrus* greening disease (also called Huanglongbing (HLB)) or potato Zebra Chip disease) in plants (e.g., *citrus* plants or potato plants). The SAMPs disclosed herein may be heat stable, as well as stable in plant extracts and/or in plant lysates (e.g., *citrus* lysates). The SAMPs described herein can effectively inhibit/kill different bacteria species, such as Gram-negative bacterial species, e.g., *Liberibacter* species, for example, *Candidatus Liberibacter asiaticus* (*C. Las*) that infects *citrus, Candidatus Liberibacter solanacearum* that infects all solanaceous plants, and *Liberibacter crescens*, which is a culturable bacterium that infects *papaya. Liberibacter crescens* can be used as a surrogate for the unculturable *Candidatus Liberibacter* species (e.g., *C. Las*). Furthermore, the SAMPs disclosed herein can also inhibit and kill other bacterial pathogens (e.g., other Gram-negative bacterial pathogens), such as *Agrobacterium tumefaciens* (also known as *Rhizobium radiobacter*) and *Pseudomonas syringae* strains. *Agrobacterium tumefaciens* can cause crown gall disease or tumors in more than 140 eudicot species. Different strains of

*Pseudomonas syringae* can cause bacterial canker or blast diseases on many dicot and monocot crops.

In one aspect, the disclosure features an isolated stable antimicrobial (e.g., antibacterial or antifungal or both) peptide (SAMP) comprising a sequence that is substantially identical (e.g., at least 50%, 55%, 60%, 65%, 70%, 75%, 80%, 85%, 90%, 91%, 92%, 93%, 94% 95%, 96%, 97%, 98%, or 99% identical) to a sequence of any one of SEQ ID NOs:1-13 and 35-37. In some embodiments, the peptide comprises a sequence having at least 75% sequence identity (e.g., at least 80%, 85%, 90%, 91%, 92%, 93%, 94% 95%, 96%, 97%, 98%, or 99% sequence identity) to a sequence of any one of SEQ ID NOs:1-13 and 35-37. In particular embodiments, the peptide comprises a sequence having at least 75% sequence identity (e.g., at least 80%, 85%, 90%, 91%, 92%, 93%, 94% 95%, 96%, 97%, 98%, or 99% sequence identity) to a sequence of any one of SEQ ID NOs:1 and 2.

In another aspect, the disclosure features an isolated stable antimicrobial (e.g., antibacterial) peptide (SAMP) comprising a sequence of $X_1GX_2X_3VSX_4ENX_5X_6QGFX_7HX_8FEX_9TFX_{10}SX_{11}EGX_{12}AEYX_{13}X_{14}HPX_{15}HVEX_{16}ANX_{17}X_{18}LX_{19}X_{20}LEKX_{21}LX_{22}X_{23}DYKPX_{24}TX_{25}RV$ (SEQ ID NO:27), in which $X_1$ is R, K, or W; $X_2$ is K or E; $X_3$ is N or D; $X_4$ is T or I; $X_5$ is L, F, or R; $X_6$ is H or Q; $X_7$ is P or T; $X_8$ is I, L, or V; $X_9$ is S or F; $X_{10}$ is E or D; $X_{11}$ is T or L; $X_{12}$ is V or I; $X_{13}$ is V or I; $X_{14}$ is S, A, or D; $X_{15}$ is S, A, or V; $X_{16}$ is Y or F; $X_{17}$ is L or T; $X_{18}$ is F, M, or L; $X_{19}$ is A, P, or T; $X_{20}$ is N or Q; $X_{21}$ is V or F; $X_{22}$ is V or I; $X_{23}$ is V or I; $X_{24}$ is T, E, or Q; and $X_{25}$ is V, E, L.

In some embodiments of this aspect, the isolated SAMP comprising a sequence of SEQ ID NO:27, in which $X_1$ in SEQ ID NO:27 is R; $X_2$ is K; $X_3$ is N; $X_4$ is I; $X_5$ is L; $X_6$ is H; $X_{10}$ is E; $X_{11}$ is T; $X_{12}$ is V; $X_{13}$ is V; $X_{16}$ is Y; $X_{17}$ is L; $X_{18}$ is F; $X_{19}$ is A; $X_{20}$ is N; $X_{21}$ is V; $X_{22}$ is V, $X_{23}$ is I; and $X_{24}$ is T.

In another aspect, the disclosure features an agricultural composition comprising an isolated stable antimicrobial (e.g., antibacterial) peptide (SAMP) described herein. The agricultural composition may further comprise at least one of an herbicide, an herbicide safener, a surfactant, a fungicide, a pesticide, a nematicide, a plant activator, a synergist, a plant growth regulator, an insect repellant, an acaricide, a molluscicide, or a fertilizer.

In another aspect, the disclosure features a nucleic acid molecule encoding an isolated stable antimicrobial (e.g., antibacterial) peptide (SAMP) described herein. Also provided is a polynucleotide comprising a promoter operably linked to the nucleic acid molecule (optionally where the promoter is heterologous to the nucleic acid molecule). The disclosure also features a cell comprising the nucleic acid molecule of the previous aspect. In some embodiments, the cell is a bacterial, yeast, plant, insect, or mammalian (e.g., human) cell. In particular embodiments, the cell is a plant cell.

In another aspect, the disclosure features a plant comprising an isolated stable antimicrobial (e.g., antibacterial) peptide (SAMP) described herein or the polynucleotide discussed above or the nucleic acid molecule encoding an isolated SAMP described herein. In some embodiments, the plant is a *citrus* plant or a solanaceous plant. In some embodiments, the plant is more tolerant to a bacterial pathogen compared to a control plant (otherwise identical) in which the SAMP is absent.

In another aspect, the disclosure features a plant comprising an in situ altered stable antimicrobial (e.g., antibacterial)

peptide (SAMP) comprising at least one amino acid substitution corresponding to an amino acid at any one of positions $X_1$ to $X_{25}$ as set forth in SEQ ID NO:27, wherein the mutated SAMP provides *Liberibacter* disease (e.g., Huanglongbing (HLB)) resistance or *Liberibacter* disease (e.g., HLB) tolerance, *Pseudomonas* disease (e.g., bacterial canker or blast diseases) resistance or *Pseudomonas* disease tolerance, or *Agrobacterium* disease (e g., Crown Gall disease or tumors) resistance or *Agrobacterium* disease tolerance to the plant.

In another aspect, the disclosure features an expression cassette comprising a promoter operably linked to a polynucleotide encoding an isolated stable antimicrobial (e.g., antibacterial) peptide (SAMP) described herein, wherein introduction of the expression cassette into a plant results in the plant having enhanced *Liberibacter* disease (e.g., HLB) resistance or *Liberibacter* disease (e.g., HLB) tolerance, *Pseudomonas* disease (e.g., bacterial canker or blast diseases) resistance or *Pseudomonas* disease tolerance, or *Agrobacterium* disease (e g., Crown Gall disease or tumors) resistance or *Agrobacterium* disease tolerance. In some embodiments, the promoter of the expression cassette is heterologous to the polynucleotide. In some embodiments, the promoter is inducible. In some embodiments, the promoter is plant tissue-specific (e.g., phloem-specific, tuber-specific, root-specific, stem-specific, trunk-specific, or leaf-specific. In some embodiments, the phloem-specific promoter is the sucrose transporter protein SUC2 promoter.

In another aspect, the disclosure features a transgenic plant comprising the expression cassette of the previous aspect, wherein the plant has enhanced *Liberibacter* disease (e.g., HLB) resistance or *Liberibacter* disease (e.g., HLB) tolerance, *Pseudomonas* disease (e.g., bacterial canker or blast diseases) resistance or *Pseudomonas* disease tolerance, or *Agrobacterium* disease (e g., Crown Gall disease or tumors) resistance or *Agrobacterium* disease tolerance, as compared to a control plant lacking the expression cassette. In some embodiments, the transgenic plant is a *citrus* plant or a solanaceous plant.

In another aspect, the disclosure features a method of preventing or treating a *Liberibacter* disease (e.g., HLB), a *Pseudomonas* disease (e.g., bacterial canker or blast diseases), or an *Agrobacterium* disease (e.g., Crown Gall disease or tumors) in a plant by contacting the plant with an isolated stable antimicrobial (e.g., antibacterial) peptide (SAMP) described herein or an agricultural composition comprising an isolated SAMP. In some embodiments of these aspects, the isolated peptide or agricultural composition is injected into the trunk of the plant. In some embodiments, the isolated peptide or agricultural composition is injected into the stem of the plant. In other embodiments, the isolated peptide or agricultural composition is foliar sprayed onto the plant. In other embodiments, the isolated peptide or agricultural composition is applied to the root of the plant. In other embodiments, the isolated peptide or agricultural composition is applied to the plant by dripping irrigation to the roots. In other embodiments, the isolated peptide or agricultural composition is applied by laser ablation.

In another aspect, the disclosure features a method of preventing or treating potato Zebra Chip (ZC) disease in a plant by contacting the plant with an isolated stable antimicrobial (e.g., antibacterial) peptide (SAMP) described herein or an agricultural composition comprising an isolated SAMP. In yet another aspect, the disclosure features a method of preventing or treating a bacterial infection in a plant caused by bacteria in the genus *Liberibacter* (e.g., *Candidatus Liberibacter* species or *Liberibacter crescens*) by contacting the plant with an isolated SAMP described herein or an agricultural composition comprising an isolated SAMP. In still another aspect, the disclosure features a method of preventing or treating a bacterial infection in a plant caused by bacteria in the genus *Agrobacterium* (e.g., *Agrobacterium tumefaciens* species) by contacting the plant with an isolated SAMP described herein or an agricultural composition comprising an isolated SAMP. In still yet another aspect, the disclosure features a method of preventing or treating a bacterial infection in a plant caused by bacteria in the genus *Pseudomonas* (e.g., *Pseudomonas syringae* species) by contacting the plant with an isolated SAMP described herein or an agricultural composition comprising an isolated SAMP.

In another aspect, the disclosure features a method of inhibiting the growth of bacteria or killing bacteria in the genus *Liberibacter* (e.g., *Candidatus Liberibacter* species or *Liberibacter crescens*) in a plant by contacting the plant with an isolated stable antimicrobial (e.g., antibacterial) peptide (SAMP) described herein or an agricultural composition comprising an isolated SAMP. In yet another aspect, the disclosure features a method of inhibiting the growth of bacteria or killing bacteria in the genus *Agrobacterium* (e.g., *Agrobacterium tumefaciens* species) in a plant by contacting the plant with an isolated stable antimicrobial (e.g., antibacterial) peptide (SAMP) described herein or an agricultural composition comprising an isolated SAMP. In still yet another aspect, the disclosure features a method of inhibiting the growth of bacteria or killing bacteria in the genus *Pseudomonas* (e.g., *Pseudomonas syringae* species) in a plant by contacting the plant with an isolated stable antimicrobial (e.g., antibacterial) peptide (SAMP) described herein or an agricultural composition comprising an isolated SAMP.

In another aspect, the disclosure features a method of preventing or treating a *Liberibacter* disease (e.g., HLB) in a plant or preventing or treating a bacterial infection in a plant caused by bacteria in the genus *Liberibacter* (e.g., *Candidatus Liberibacter* species (e.g., *Candidatus Liberibacter asiaticus, Candidatus Liberibacter africanus*, and *Candidatus Liberibacter americanus*) or *Liberibacter crescens*) by introducing an expression cassette described herein (e.g., an expression cassette comprising a promoter operably linked to a polynucleotide encoding an isolated stable antimicrobial (e.g., antibacterial) peptide described herein) into the plant. In another aspect, the disclosure features a method of preventing or treating potato ZC disease in a plant or preventing or treating a bacterial infection in a plant caused by bacteria in the genus *Liberibacter* (e.g., *Candidatus Liberibacter* species (e.g., *Candidatus Liberibacter solanacearum* (*Ca. L. solanacearum*)) or *Liberibacter crescens*) by introducing an expression cassette described herein (e.g., an expression cassette comprising a promoter operably linked to a polynucleotide encoding an isolated SAMP described herein) into the plant.

In yet another aspect, the disclosure features a method of preventing or treating a *Pseudomonas* disease (e.g., bacterial canker or blast diseases) in a plant or preventing or treating a bacterial infection in a plant caused by bacteria in the genus *Pseudomonas* (e.g., *Pseudomonas syringae* species) by introducing an expression cassette described herein (e.g., an expression cassette comprising a promoter operably linked to a polynucleotide encoding an isolated stable antimicrobial (e.g., antibacterial) peptide described herein) into the plant.

In still yet another aspect, the disclosure features a method of preventing or treating a *Agrobacterium* disease (e.g., Crown Gall disease or tumors) in a plant or preventing or treating a bacterial infection in a plant caused by bacteria in the genus *Agrobacterium* (e.g., *Agrobacterium tumefaciens* species) by introducing an expression cassette described herein (e.g., an expression cassette comprising a promoter operably linked to a polynucleotide encoding an isolated stable antimicrobial (e.g., antibacterial) peptide described herein) into the plant.

In another aspect, the disclosure features a method of inhibiting the growth of bacteria or killing bacteria in the genus *Liberibacter* (e.g., *Candidatus Liberibacter* species or *Liberibacter crescens*) in a plant by introducing an expression cassette described herein (e.g., an expression cassette comprising a promoter operably linked to a polynucleotide encoding an isolated stable antimicrobial (e.g., antibacterial) peptide described herein) into the plant.

In another aspect, the disclosure features a method of inhibiting the growth of bacteria or killing bacteria in the genus *Agrobacterium* (e.g., *Agrobacterium tumefaciens* species) in a plant by introducing an expression cassette described herein (e.g., an expression cassette comprising a promoter operably linked to a polynucleotide encoding an isolated stable antimicrobial (e.g., antibacterial) peptide described herein) into the plant.

In yet another aspect, the disclosure features a method of inhibiting the growth of bacteria or killing bacteria in the genus *Pseudomonas* (e.g., *Pseudomonas syringae* species) in a plant by introducing an expression cassette described herein (e.g., an expression cassette comprising a promoter operably linked to a polynucleotide encoding an isolated stable antimicrobial (e.g., antibacterial) peptide described herein) into the plant.

In another aspect, the disclosure features a method of producing a plant having enhanced *Liberibacter* disease (e.g., HLB) resistance or *Liberibacter* disease (e.g., HLB) tolerance by introducing an isolated stable antimicrobial (e.g., antibacterial) peptide described herein or an expression cassette comprising a promoter operably linked to a polynucleotide encoding an isolated stable antimicrobial (e.g., antibacterial) peptide into a plurality of plants; and selecting a plant that comprises the isolated peptide or expresses the polynucleotide from the plurality of plants.

In another aspect, the disclosure features a method of producing a plant having enhanced potato ZC disease resistance or potato ZC disease tolerance by introducing an isolated stable antimicrobial (e.g., antibacterial) peptide (SAMP) described herein or an expression cassette comprising a promoter operably linked to a polynucleotide encoding an isolated SAMP into a plurality of plants; and selecting a plant that comprises the isolated peptide or expresses the polynucleotide from the plurality of plants.

In another aspect, the disclosure features a method of producing a plant having enhanced *Pseudomonas* disease (e.g., bacterial canker or blast diseases) resistance or *Pseudomonas* disease (e.g., bacterial canker or blast diseases) tolerance by introducing an isolated stable antimicrobial (e.g., antibacterial) peptide described herein or an expression cassette comprising a promoter operably linked to a polynucleotide encoding an isolated stable antimicrobial (e.g., antibacterial) peptide into a plurality of plants; and selecting a plant that comprises the isolated peptide or expresses the polynucleotide from the plurality of plants.

In another aspect, the disclosure features a method of producing a plant having enhanced *Agrobacterium* disease (e.g., Crown Gall disease or tumors) resistance or *Agrobacterium* disease (e.g., Crown Gall disease or tumors) tolerance by introducing an isolated stable antimicrobial (e.g., antibacterial) peptide described herein or an expression cassette comprising a promoter operably linked to a polynucleotide encoding an isolated stable antimicrobial (e.g., antibacterial) peptide into a plurality of plants; and selecting a plant that comprises the isolated peptide or expresses the polynucleotide from the plurality of plants.

In another aspect, the disclosure features a method of producing a plant having enhanced *Liberibacter* disease (e.g., HLB) resistance or *Liberibacter* disease (e.g., HLB) tolerance (i.e., enhanced resistance or tolerance to a bacterial infection caused by bacteria in the genus *Liberibacter* (e.g., *Candidatus Liberibacter* species (e.g., *Candidatus Liberibacter asiaticus, Candidatus Liberibacter africanus*, and *Candidatus Liberibacter americanus*) or *Liberibacter crescens*)) by introducing a mutation into a polynucleotide in the plant, wherein the mutated polynucleotide encodes an isolated stable antimicrobial (e.g., antibacterial) peptide described herein (e.g., an isolated SAMP having at least 75% sequence identity to the sequence of SEQ ID NO:1 or 2). In another aspect, the disclosure features a method of producing a plant having enhanced potato ZC disease resistance or potato ZC disease tolerance (i.e., enhanced resistance or tolerance to a bacterial infection caused by bacteria in the genus *Liberibacter* (e.g., *Candidatus Liberibacter* species (e.g., *Candidatus Liberibacter solanacearum* (*Ca. L. solanacearum*)) or *Liberibacter crescens*) by introducing a mutation into a polynucleotide in the plant, wherein the mutated polynucleotide encodes an isolated stable antimicrobial (e.g., antibacterial) peptide (SAMP) described herein (e.g., an isolated SAMP having at least 75% sequence identity to the sequence of SEQ ID NO:1 or 2). In some embodiments of these aspects, the introducing occurs in situ in the genome of a plant cell. In particular embodiments, the introducing comprises clustered regularly interspaced short palindromic repeats (CRISPR)/Cas genome editing. In some embodiments of these aspects, the plant is a *citrus* plant or a solanaceous plant (e.g., a potato plant).

In still another aspect, the disclosure features a method of producing a plant having enhanced *Agrobacterium* disease resistance or *Agrobacterium* disease tolerance (i.e., enhanced resistance or tolerance to a bacterial infection caused by bacteria in the genus *Agrobacterium* (e.g., Crown Gall disease or tumors caused by *Agrobacterium* strains)) by introducing a mutation into a polynucleotide in the plant, wherein the mutated polynucleotide encodes an isolated stable antimicrobial (e.g., antibacterial) peptide (SAMP) described herein (e.g., an isolated SAMP having at least 75% sequence identity to the sequence of SEQ ID NO:1 or 2). In some embodiments of these aspects, the introducing occurs in situ in the genome of a plant cell. In particular embodiments, the introducing comprises clustered regularly interspaced short palindromic repeats (CRISPR)/Cas genome editing. In some embodiments of these aspects, the plant is eudicot plant.

In still another aspect, the disclosure features a method of producing a plant having enhanced *Pseudomonas* disease resistance or *Pseudomonas* disease tolerance (i.e., enhanced resistance or tolerance to a bacterial infection caused by bacteria in the genus *Pseudomonas* (e.g., bacterial canker or blast diseases caused by *Pseudomonas* strains)) by introducing a mutation into a polynucleotide in the plant, wherein the mutated polynucleotide encodes an isolated stable antimicrobial (e.g., antibacterial) peptide (SAMP) described herein (e.g., an isolated SAMP having at least 75% sequence identity to the sequence of SEQ ID NO:1 or 2). In some embodiments of these aspects, the introducing occurs in situ in the genome of a plant cell. In particular embodiments, the introducing comprises clustered regularly interspaced short palindromic repeats (CRISPR)/Cas genome editing. In some embodiments of these aspects, the plant is a monocot or dicot plant (e.g., a tomato plant).

In any of the compositions or methods described in the present disclosure, the plant may species be from the genus *Citrus* (e.g., *Citrus maxima, Citrus medica, Citrus micrantha, Citrus reticulate, Citrus aurantiifolia, Citrus aurantium, Citrus latifolia, Citrus limon, Citrus limonia, Citrus paradise, Citrus sinensis*, and *Citrus tangerine*) or species from the family Solanaceae (e.g., *Solanum* spp., *Capsicum* spp., and *Nicotiana* spp.). Species from the genus *Solanum* include, e.g., *Solanum tuberosum, Solanum lycopersicum, Solanum melongena, Solanum aviculare, Solanum capsicastrum, Solanum crispum, Solanum laciniatum, Solanum laxum, Solanum pseudocapsicum, Solanum rantonnetii, Solanum seaforthianum*, and *Solanum wendlandii*. Species from the genus *Capsicum* include, e.g., *Capsicum annuum, Capsicum baccatum, Capsicum campylopodium, Capsicum cardenasii, Capsicum chacoense, Capsicum cornutum, Capsicum dusenii, Capsicum eximium, Capsicum friburgense, Capsicum frutescens, Capsicum geminifolium, Capsicum havanense, Capsicum lanceolatum, Capsicum lycianthoides, Capsicum minutiflorum, Capsicum mositicum, Capsicum pubescens, Capsicum recurvatum, Capsicum schottianum, Capsicum spina-alba, Capsicum tovarii*, and *Capsicum villosum*. Species from the genus *Nicotiana* include, e.g., *Nicotiana acuminate, Nicotiana benthamiana, Nicotiana glauca, Nicotiana longiflora, Nicotiana rustica, Nicotiana tabacum*, and *Nicotiana occidentalis*.

In particular embodiments, the plant is selected from the group consisting of *Citrus reticulata, Citrus sinensis, Citrus clementina, Capsicum annuum, Solanum tuberosum, Solanum lycopersicum, Solanum melongena*, and *Nitotiana benthamiana*. In particular embodiments, the plant is a sweet orange plant (*Citrus sinensis*). In particular embodiments, the plant is a clementine plant (*Citrus* Clementina). In particular embodiments, the plant is a potato plant (*Solanum tuberosum*). In some embodiment, the plant is a vegetable- or fruit-producing plant.

In any of the aspects of the disclosure described herein, in some embodiments, the SAMP is a heat stable (HS) peptide.

Furthermore, in any of the aspects of the disclosure described herein, in some embodiments, the SAMP may also provide resistance or tolerance to bacterial diseases caused by other bacterial pathogens, such as *Agrobacterium tumefaciens* (also known as *Rhizobium radiobacter*) and *Pseudomonas syringae*.

Definitions

As used herein, the term "*Liberibacter* disease" refers to a disease, such as an infection, caused by bacteria in the genus *Liberibacter* (e.g., *Candidatus Liberibacter* species or *Liberibacter crescens*). A *Liberibacter* disease may infect plants such as *citrus* plants (e.g., orange, grapefruit, tangerine, lemon, line, key line, papeda, citron, and pomelo) and solanaceous plants (e.g., potato, tomato, eggplant, and pepper). Huanglongbing (HLB) is a type of *Liberibacter* disease that infects *citrus* plants.

As used herein, the terms "*citrus* greening disease" and "Huanglongbing (HLB)" refer to a bacterial infection of plants (e.g., *citrus* plants) caused by bacteria in the genus *Liberibacter* (e.g., *Candidatus Liberibacter* species (e.g., *Candidatus Liberibacter asiaticus, Candidatus Liberibacter africanus*, and *Candidatus Liberibacter americanus*) or *Liberibacter crescens*). The infection is vectored and transmitted by the Asian *citrus* psyllid, *Diaphorina citri*, and the African *citrus* psyllid, *Trioza erytreae*. Three different types of HLB are currently known: the heat-tolerant Asian form, and the heat-sensitive African and American forms.

As used herein, the term "Potato Zebra Chip (ZC) disease" refers to a bacterial infection of plants (e.g., potato plants) caused by bacteria in the genus *Liberibacter* (e.g., *Candidatus Liberibacter* species (e.g., *Candidatus Liberibacter solanacearum* (*Ca. L. solanacearum*)) or *Liberibacter crescens*). The infection is vectored and transmitted by potato psyllids (e.g., *Bactericera cockerelli*).

As used herein, the term "*Agrobacterium* disease" refers to a disease, such as an infection, caused by bacteria in the genus *Agrobacterium* (e.g., *Agrobacterium tumefaciens* species, also known as *Rhizobium radiobacter*). *Agrobacterium* diseases can comprise Crown Gall disease, or tumors, in more than 140 eudicot species.

As used herein, the term "*Pseudomonas* disease" refers to a disease, such as an infection, caused by bacteria in the genus *Pseudomonas* (e.g., *Pseudomonas syringae* species). *Pseudomonas* diseases can comprise bacterial canker or blast diseases on many dicot and monocot crops (e.g., Tomato Bacterial Speck, Tomato Bacterial Spot, and Tomato Bacterial Canker).

As used herein, the term "disease resistance" refers to the ability of a plant to not be affected by a *Liberibacter* disease (e.g., HLB), *Agrobacterium* disease, or *Pseudomonas* disease; or infection by *Liberibacter* bacteria (e.g., *Candidatus Liberibacter* species or *Liberibacter crescens*), *Agrobacterium* bacteria (e.g., *Agrobacterium tumefaciens* species), or *Pseudomonas* bacteria (e.g., *Pseudomonas syringae* species).

As used herein, the term "disease tolerance" refers to the ability of a plant to continuously grow and survive despite being infected by bacteria (e.g., gram-negative bacteria, such as *Liberibacter* bacteria, *Agrobacterium* bacteria or *Pseudomonas* bacteria).

As used herein, the term "*Liberibacter* disease resistance" refers to the ability of a plant to not be affected by a *Liberibacter* disease (e.g., HLB) or infection by *Liberibacter* bacteria (e.g., *Candidatus Liberibacter* species or *Liberibacter crescens*).

As used herein, the term "*Liberibacter* disease tolerance" refers to the ability of a plant to continuously grow and survive despite being infected by *Liberibacter* bacteria (e.g., *Candidatus Liberibacter* species or *Liberibacter crescens*) or having a *Liberibacter* disease (e.g., HLB). In some embodiments, a plant with a *Liberibacter* disease (e.g., HLB) may show minor symptoms of the disease, such as yellowing of leaves, blotchy mottle of the leaves, zinc-deficiency-like mottle, chlorosis, and reduced fruit yield, but is still able to grow or produce fruit despite the infection.

As used herein, the term "potato ZC disease resistance" refers to the ability of a plant to not be affected by potato ZC disease or infection by *Liberibacter* (e.g., *Candidatus Liberibacter* species (e.g., *Candidatus Liberibacter solanacearum* (*Ca. L. solanacearum*)) or *Liberibacter crescens*) bacteria.

As used herein, the term "potato ZC disease tolerance" refers to the ability of a plant to continuously grow and survive despite being infected by *Liberibacter* (e.g., *Candidatus Liberibacter* species (e.g., *Candidatus Liberibacter solanacearum* (*Ca. L. solanacearum*)) or *Liberibacter crescens*) bacteria or having potato ZC disease. In some embodiments, a plant with potato ZC disease may show minor symptoms of potato ZC disease, such as chlorosis, leaf scorching, swollen nodes, vascular tissue browning, curled leaves, collapsed stolons, enlarged lenticels, vascular tissue browning, medullary ray discoloration, and necrotic flecking of tuber tissue, but is still able to grow or produce potato despite the infection.

As used herein, the term "*Agrobacterium* disease resistance" refers to the ability of a plant to not be affected by an *Agrobacterium* disease (e.g., Crown Gall disease) or infection by *Agrobacterium* bacteria (e.g., *Agrobacterium tumefaciens* species, also known as *Rhizobium radiobacter*).

As used herein, the term "*Agrobacterium* disease tolerance" refers to the ability of a plant to continuously grow and survive despite being infected by *Agrobacterium* bacteria (e.g., *Agrobacterium tumefaciens* species, also known as *Rhizobium radiobacter*) or having an *Agrobacterium* disease (e.g., Crown Gall disease).

As used herein, the term "*Pseudomonas* disease resistance" refers to the ability of a plant to not be affected by a *Pseudomonas* disease (e.g., Tomato Bacterial Speck, Tomato Bacterial Spot, and Tomato Bacterial Canker) or infection by *Pseudomonas* bacteria (e.g., *Agrobacterium tumefaciens* species).

As used herein, the term "*Pseudomonas* disease tolerance" refers to the ability of a plant to continuously grow and survive despite being infected by *Pseudomonas* bacteria (e.g., *Agrobacterium tumefaciens* species) or having a *Pseudomonas* disease (e.g., Tomato Bacterial Speck, Tomato Bacterial Spot, and Tomato Bacterial Canker).

As used herein, the term "stable antimicrobial peptides" or "SAMPs" refers to peptides identified in plants that are *Liberibacter* disease-resistant/tolerant (e.g., HLB-resistant/tolerant). Such peptides are expressed at a higher level in *Liberibacter* disease-resistant/tolerant (e.g., HLB-resistant/tolerant) plants than *Liberibacter* disease-susceptible (e.g., HLB-susceptible) plants. These SAMPs may be injected into plants to prevent or treat a *Liberibacter* disease (e.g., HLB). In some embodiments, the isolated SAMPs disclosed herein have antibacterial or antifungal or both properties. In some embodiments, the isolated SAMPs disclosed herein are heat stable (e.g., heat stable (HS) peptides). In some embodiments, the isolated SAMPs disclosed herein are also stable in plant extracts. In further embodiments, the isolated SAMPs disclosed herein are also stable in plant lysates (e.g., *citrus* lysates).

As used herein, the term "agricultural composition" refers to a composition formulated for application to a plant or plant part (e.g., seed, cutting, shoots, etc.). An agricultural composition is typically in liquid form, e.g., for application by spraying or soaking, but can be in a powder for rehydration or application (dusting or dry coating), or gaseous form (e.g., for enclosed environments). The agricultural composition can be concentrated, e.g., for dilution or water or other solvent. An agricultural composition can also include more than one active ingredient, e.g., a SAMP (e.g., an HS peptide) described herein, alone or in combination with a fungicide, herbicide, fertilizer, etc.

As used herein, the term "treat" or "treating" a *Liberibacter* disease (e.g., an HLB or a potato ZC disease) in plants refers to the reduction or eradication of symptoms caused by the *Liberibacter* disease by methods described herein. Symptoms of HLB include, but are not limited to, yellowing of leaves, blotchy mottle of the leaves, zinc-deficiency-like mottle, severe chlorosis, and reduced fruit yield. Symptoms of potato ZC disease include, but are not limited to, chlorosis, leaf scorching, swollen nodes, vascular tissue browning, curled leaves, collapsed stolons, enlarged lenticels, vascular tissue browning, medullary ray discoloration, and necrotic flecking of tuber tissue. In some embodiments, the disclosed methods may not necessarily result in eradication or cure of the *Liberibacter* disease (e.g., HLB or potato ZC disease), but can significantly reduce the symptoms caused by the disease.

As used herein, the term "prevent" or "preventing" a *Liberibacter* disease (e.g., an HLB or a potato ZC disease) in plants refers protecting a plant that is at risk for the disease from developing the disease, or decreasing the risk that a plant may develop the disease. A plant may be contacted with a SAMP (e.g., an HS peptide) described herein before the plant develops the disease, or shows signs of the disease.

As used herein, the term "plant" includes whole plants, shoot vegetative organs/structures (e.g., leaves, stems and tubers), roots, flowers and floral organs/structures (e.g., bracts, sepals, petals, stamens, carpels, anthers and ovules), seed (including embryo, endosperm, and seed coat) and fruit (the mature ovary), plant tissue (e.g., vascular tissue, ground tissue, and the like) and cells (e.g., guard cells, egg cells, and the like), and progeny of same. Plants that can be treated as described herein include, e.g., *citrus* plants (e.g., orange, grapefruit, tangerine, lemon, line, key line, papeda, citron, and pomelo) and solanaceous plants (e.g., potato, tomato, eggplant, and pepper).

The term "plant" also includes naturally occurring mutants and genetically modified plants. A "genetically modified plant" or "transgenic plant" refers to one whose genome has been manipulated so that it is different than a wild-type plant of the same species, variety or cultivar, e.g., to add a gene or genetic element, remove a gene or genetic element, mutate a gene or genetic element, change chromatin structure, change gene or protein expression levels, etc. A transgenic plant may contain an expression vector or cassette. The expression cassette typically comprises a polypeptide-encoding sequence or a modulating nucleic acid (e.g., an antisense, an siRNA or ribozyme) operably linked (i.e., under regulatory control of) to an appropriate inducible or constitutive regulatory sequences that allow for the expression of a polypeptide or modulating nucleic acid. The expression cassette can be introduced into a plant by transformation or by breeding after transformation of a parent plant. Such methods can be used in a whole plant, including seedlings and mature plants, as well as to a plant part, such as seed, fruit, leaf, or root, plant tissue, plant cells or any other plant material, e.g., a plant explant, as well as to progeny thereof, and to in vitro systems that mimic biochemical or cellular components or processes in a cell. In the context of the present disclosure, genetically modified plants may include genetic modifications in a gene encoding a SAMP (e.g., an HS peptide). In some embodiments, the modified gene in the genetically modified plant may encode a SAMP (e.g., an HS peptide) described herein (e.g., a SAMP having at least 75% sequence identity or at least one amino acid substitution relative to the sequence of any one of SEQ ID NOs:1-13 and 35-37 (e.g., SEQ ID NOs:1 and 2)).

An "expression cassette" refers to a nucleic acid construct that, when introduced into a host cell, results in transcription and/or translation of an RNA or polypeptide, respectively.

As used herein, the term "polynucleotide" refers to an oligonucleotide, or nucleotide, and fragments or portions thereof, and to DNA or RNA of genomic or synthetic origin, which may be single- or double-stranded, and represent the sense or anti-sense strand. A single polynucleotide is translated into a single polypeptide.

As used herein, the terms "peptide" and "polypeptide" are used interchangeably and describe a single polymer in which the monomers are amino acid residues which are joined together through amide bonds. A polypeptide is intended to encompass any amino acid sequence, either naturally occurring, recombinant, or synthetically produced.

As used herein, the term "substantial identity" or "substantially identical," used in the context of nucleic acids or polypeptides, refers to a sequence that has at least 50% sequence identity with a reference sequence. Alternatively, percent identity can be any integer from 50% to 100%. In some embodiments, a sequence is substantially identical to a reference sequence if the sequence has at least 50%, 55%, 60%, 65%, 70%, 75%, 80%, 85%, 90%, 91%, 92%, 93%, 94%, 95%, 96%, 97%, 98%, or 99% sequence identity to the reference sequence as determined using the methods described herein; preferably BLAST using standard parameters, as described below. Embodiments of the present disclosure provide for SAMPs (e.g., HS peptides) that are substantially identical to any of SEQ ID NOs:1-13 and 35-37 (SEQ ID NOs:1 and 2).

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A comparison window includes reference to a segment of any one of a number of contiguous positions, e.g., a segment of at least 10 residues. In some embodiments, the comparison window has from 10 to 600 residues, e.g., about 10 to about 30 residues, about 10 to about 20 residues, about 50 to about 200 residues, or about 100 to about 150 residues, in which a sequence may be compared to a reference sequence of the same number of contiguous positions after the two sequences are optimally aligned.

Algorithms that are suitable for determining percent sequence identity and sequence similarity are the BLAST and BLAST 2.0 algorithms, which are described in Altschul et al. (1990) *J. Mol. Biol.* 215: 403-410 and Altschul et al. (1977) *Nucleic Acids Res.* 25: 3389-3402, respectively. Software for performing BLAST analyses is publicly available through the National Center for Biotechnology Information (NCBI) web site. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et at supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, *Proc. Natl. Acad Sci. USA* 89:10915 (1989)).

The BLAST algorithm also performs a statistical analysis of the similarity between two sequences (see, e.g., Karlin & Altschul, *Proc. Nat'l. Acad Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, an amino acid sequence is considered similar to a reference sequence if the smallest sum probability in a comparison of the test amino acid sequence to the reference amino acid sequence is less than about 0.01, more preferably less than about $10^{-5}$, and most preferably less than about 10−20.

BRIEF DESCRIPTION OF THE DRAWINGS

FIG. 4A shows HLB-positive *citrus* plants with similar *C. Las* titer were treated with buffer (mock), or SAMP (at 100 nM or 10 μM) once by trunk injection. Pictures were taken after 5 weeks of treatment. FIG. 4B shows the titer of *C. Las* was measured by PCR on genomic DNA isolated from 8 new leaves from each mock or SAMP-treated *citrus* plants.

FIG. 5A shows potato plants were pre-treated with SAMP (10 μM) or buffer only (mock), and then were exposed to *C. Lso* positive potato psyllids for 5 days. Plants are 3 weeks post infection. FIG. 5B shows potato tubers harvested from mock or SAMP pre-treated plants. FIG. 5C shows frying test of potato tubers harvested from SAMP or mock pre-treated *C. Lso* infected plants and healthy plants.

FIG. 6A shows tomato plants were pre-treated with SAMP or buffer only (mock) and then were exposed to *C. Lso* positive potato psyllids for 5 days. Plants are 4 weeks post infection. FIG. 6B shows above-ground biomass of SAMP pre-treated tomato plants.

DETAILED DESCRIPTION OF THE EMBODIMENTS

I. Introduction

Figure 1A:
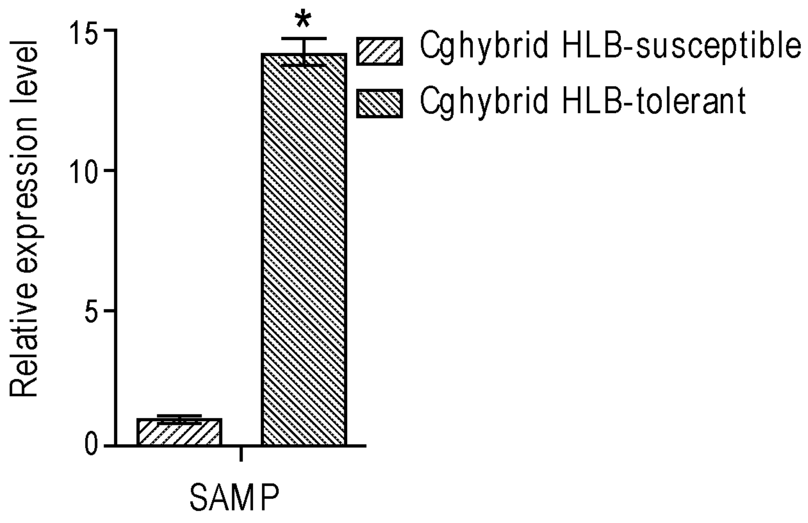
FIGS. 1A and 1B are bar graphs showing the expression levels of stable antimicrobial peptides (SAMPs) in HLB-susceptible and HLB-tolerant plants.

*Citrus* greening disease or "Huanglongbing" (HLB), caused by bacteria *Candidatus Liberibacter*, is a type of *Liberibacter* disease that specifically infects *citrus* plants. HLB is one of the most destructive diseases of *citrus*. *Liberibacter* (e.g., *Candidatus Liberibacter* species (*Ca. Liberibacter* or *Ca. L.*) or *Liberibacter crescens*) is a Gram-negative bacterial pathogen restricted to the phloem. HLB has caused in a significant reduction in *citrus* quality and quantity, resulting in billions of dollars in losses of *citrus* products every year, and seriously impacts the viability of the *citrus* industry. Current methods of treating HLB mainly involve removal of infected plants and chemical treatment against the insect vector and only led to partial control of the disease. No sustainable disease control methods for HLB have been found. The expansive and fast spread of the disease to multiple locations has already made complete removal of the infected trees an impractical strategy.

To identify and characterize important *citrus* defense regulators, a comparative analysis of small RNAs (sRNAs) and sRNA target genes between HLB-resistant and HLB-tolerant hybrid varieties and HLB-susceptible varieties. Several *citrus* defense regulators that uniquely respond to *Ca. L.* infection in HLB-resistant and HLB-tolerant hybrid varieties, but not in HLB-susceptible varieties were identified. Among the identified *citrus* defense regulators, putative antibacterial genes encoding stable antimicrobial proteins were found to express at a much higher level in the HLB-resistant and HLB-tolerant hybrid varieties than in HLB-susceptible varieties. The HLB-resistant and HLB-tolerant hybrid rootstocks are from completely different geographic and genetic backgrounds.

After the identification of these stable antimicrobial proteins that provide HLB-resistance or HLB-tolerance, a functional analysis of these stable antimicrobial proteins was performed in Solanaceae plant *Nicotiana benthamiana* (*Nb*) that is infected with *Candidatus Liberibacter solanacearum* (*Ca. L. solanacearum*) transmitted by potato psyllid (Example 2). The result showed that applying SAMPs to infected plants can effectively inhibit or kill *Liberibacter* species (e.g., *Candidatus Liberibacter* species) and achieve plant protection.

The disclosure includes isolated stable antimicrobial (e.g., antibacterial) peptides (SAMPs) (e.g., heat stable (HS) peptides), agricultural compositions containing such peptides, plants comprising such peptides, transgenic plants expressing such peptides, methods of using such peptides to prevent or treat bacterial diseases, such as those caused by Gram-negative bacteria, e.g., a *Liberibacter* disease (e.g., an HLB or a potato ZC disease), bacterial diseases caused by *Agrobacterium tumefaciens* (also known as *Rhizobium radiobacter*), and bacterial diseases caused by *Pseudomonas syringae*, and methods of producing plants that comprise such peptides or express such peptides. The SAMPs disclosed herein can inhibit and kill bacterial pathogens, such as Gram-negative bacterial pathogens, e.g., *Liberibacter* species, *Agrobacterium tumefaciens* (also known as *Rhizobium radiobacter*), and *Pseudomonas syringae* strains. The SAMPs disclosed herein can also provide plants with resistance or tolerance to bacterial diseases, such as those caused by Gram-negative bacteria, e.g., bacterial diseases caused by *Liberibacter* species, *Agrobacterium tumefaciens*, and *Pseudomonas syringae* strains.

II. Stable Antimicrobial Peptides (SAMPs)

Figure 1B:
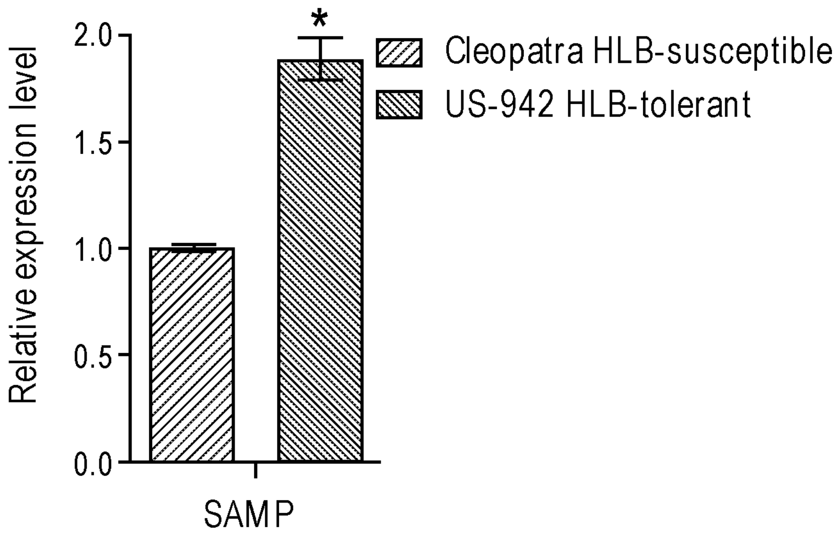
Figure 1C:
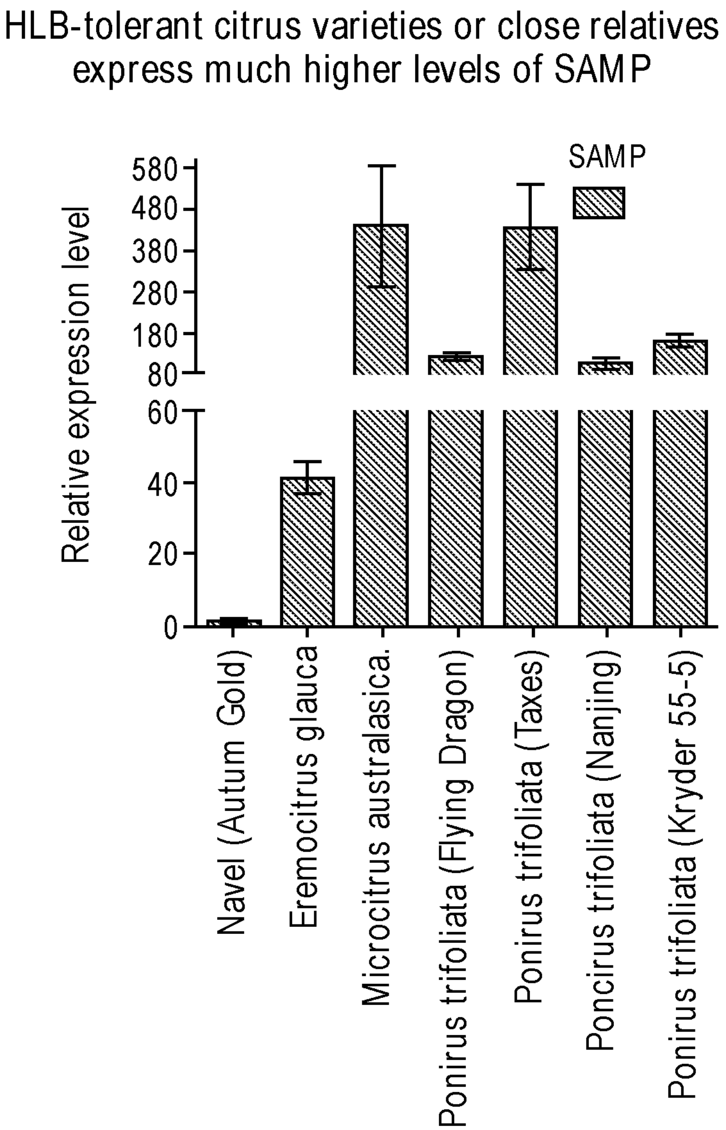
FIG. 1C shows HLB-tolerant *citrus* varieties or close relatives express elevated levels of SAMPs.

The disclosure provides stable antimicrobial (e.g., antibacterial) peptides (SAMPs) that may be injected into plants to prevent or treat a bacterial disease, such as a Gram-negative bacterial disease, e.g., a *Liberibacter* disease (e.g., HLB). The SAMPs disclosed herein may also be used to prevent or treat bacterial diseases caused by other bacterial pathogens, such as *Agrobacterium tumefaciens* (also known as *Rhizobium radiobacter*) and *Pseudomonas syringae* strains. The plants may also be genetically modified to express one or more of the SAMPs described herein. The present disclosure identified genes in plants encoding SAMPs that are differentially expressed in *Liberibacter* disease-resistant/tolerant (e.g., HLB-resistant/tolerant) plants and *Liberibacter* disease-susceptible (e.g., HLB-susceptible) plants. In some embodiments, the SAMPs disclosed herein are heat stable (e.g., heat stable (HS) peptides). In some embodiments, the SAMPs disclosed herein are also stable in plant extracts. In further embodiments, the SAMPs disclosed herein are also stable in plant lysates (e.g., *citrus* lysates). As shown in FIGS. 1A and 1B, these SAMPs expressed at a much higher level in *Liberibacter* disease-resistant/tolerant (e.g., HLB-resistant/tolerant) plants than in *Liberibacter* disease-susceptible (e.g., HLB-susceptible) plants. By comparing the amino acid sequences of SAMPs from different *citrus* plants and solanaceous plants, it is found that the SAMPs expressed in some HLB-resistant/tolerant *citrus* plants and pepper (Ca: *Capsicum annuum*) are shorter while the SAMPs expressed in HLB-susceptible solanaceous plants are longer. Table 1 below provides amino acid sequences of SAMPs in various hybrid plants, *citrus* plants, and solanaceous plants.

TABLE 1

| SAMP | Plant Source | Amino Acid Sequence | Nucleic Acid Sequence |
|---|---|---|---|
| CghSAMPa | *Eremocitrus glauca* x *citrus* sp. | MCCNRGKNVSIENLHQ GFTHIFESTFESTEGVAE YVSHPSHVEYANLFLA NLEKVLVIDYKPTTVRV (SEQ ID NO: 1) | ATGTGCTGCAACAGGGGCAAGAATGTGAGCATTGAGA ATCTTCATCAGGGTTTCACTCATATTTTTGAATCTACC TTTGAGAGCACAGAGGGTGTTGCAGAGTATGTATCTC ATCCGTCACATGTTGAATACGCAAACTTGTTCCTGGCC AACTTGGAGAAAGTTCTCGTGATTGACTACAAACCGA CAACAGTACGTGTCTGAGAAGGGTGGGCGCGCCGACC CAGCTTTCTTGTACAAAGTTGGCATTATAAGAAAG (SEQ ID NO: 14) or ATGTGCTGCAACAGGGGCAAGAATGTGAGCATTGAGA ATCTTCATCAGGGTTTCACTCATATTTTTGAATCTACC TTTGAGAGCACAGAGGGTGTTGCAGAGTATGTATCTC ATCCGTCACATGTTGAATACGCAAACTTGTTCCTGGCC AACTTGGAGAAAGTTCTCGTGATTGACTACAAACCGA CAACAGTACGTGTCTGA (SEQ ID NO: 28) |
| CghSAMPb | *Eremocitrus glauca* x *citrus* sp. | MCCNRGKNVSIENLHQ GFPHLFEFTFESTEGVAE YVSHPAHVEYANLFLA NLEKVLVIDYKPTTVRV (SEQ ID NO: 2) | ATGTGCTGCAACAGGGGCAAGAATGTGAGCATTGAGA ATCTTCATCAGGGTTTCCCTCATCTTTTCGAATTTACCT TTGAGAGCACAGAGGGTGTTGCAGAGTATGTATCTCA TCCGGCACATGTTGAATACGCAAACTTGTTCCTGGCC AACTTGGAGAAAGTTCTCGTGATTGACTACAAACCGA CAACAGTACGTGTCTGAGAAGGGTGGGCGCGCCGACC CAGCTTTCTT (SEQ ID NO: 15) or ATGTGCTGCAACAGGGGCAAGAATGTGAGCATTGAGA ATCTTCATCAGGGTTTCCCTCATCTTTTCGAATTTACCT TTGAGAGCACAGAGGGTGTTGCAGAGTATGTATCTCA TCCGGCACATGTTGAATACGCAAACTTGTTCCTGGCC AACTTGGAGAAAGTTCTCGTGATTGACTACAAACCGA CAACAGTACGTGTCTGA (SEQ ID NO: 29) |
| 942SAMP1, US-942 | *Citrus reticulata* x *Poncirus trifoliata* | MCCNRGKNVSIENLHQ GFTHIFESTFESTEGVAE YVAHPAHVEYANLFLA NLEKVLVIDYKPTTERV (SEQ ID NO: 3) | ATGTGCTGCAACAGGGGCAAGAATGTGAGCATTGAGA ATCTTCATCAGGGTTTCACTCATATTTTTGAATCTACC TTTGAGAGCACAGAGGGTGTTGCAGAGTATGTAGCTC ATCCGGCACATGTTGAATACGCAAACTTGTTCCTGGC CAACTTGGAGAAAGTTCTCGTGATTGACTACAAACCG ACAACAGAACGTGTCTAAGGGTGGGCGCGCCGACCCA GCTTTCTTGTACAA (SEQ ID NO: 16) or ATGTGCTGCAACAGGGGCAAGAATGTGAGCATTGAGA ATCTTCATCAGGGTTTCACTCATATTTTTGAATCTACC TTTGAGAGCACAGAGGGTGTTGCAGAGTATGTAGCTC ATCCGGCACATGTTGAATACGCAAACTTGTTCCTGGC CAACTTGGAGAAAGTTCTCGTGATTGACTACAAACCG ACAACAGAACGTGTCTAA (SEQ ID NO: 30) |
| CsSAMP1 | *Citrus sinensis* | MCCNRGKNVSIENLHQ GFTHIFESTEESTEGVAE YVAHPAHVEYANLFLA NLEKVLVIDYKPTTVRV (SEQ ID NO: 4) | ATGTGCTGCAACAGGGGCAAGAATGTGAGCATTGAGA ATCTTCATCAGGGTTTCACTCATATTTTTGAATCTACC TTTGAGAGCACAGAGGGTGTTGCAGAGTATGTAGCTC ATCCGGCACATGTTGAATACGCAAACTTGTTCCTGGC CAACTTGGAGAAAGTTCTCGTGATTGACTACAAACCG ACAACAGTACGTGTCTGAGTTGTACTAGTAGGGAA (SEQ ID NO: 17) or ATGTGCTGCAACAGGGGCAAGAATGTGAGCATTGAGA ATCTTCATCAGGGTTTCACTCATATTTTTGAATCTACC TTTGAGAGCACAGAGGGTGTTGCAGAGTATGTAGCTC ATCCGGCACATGTTGAATACGCAAACTTGTTCCTGGC CAACTTGGAGAAAGTTCTCGTGATTGACTACAAACCG ACAACAGTACGTGTCTGA (SEQ ID NO: 31) |
| CsSAMP2 | *Citrus sinensis* | MIAELIRSCCGLELLAV KYKGKNVSIENLHQGFT HIFESTEESTEGVAEYV AHPAHVEYANLFLANL EKVLVIDYKPTTVRV (SEQ ID NO: 5) | ATGGAAGAAGCTAAAGGAGTGGTGAAGCACGTACTTC TGGCCAAGTTCAAAGAAGGGACTGCTCAAGATCAAAT TGATCAGCTCATCAAAGACTATGCAAATCTTGTGAAT CTCATTGAACCCATGAAGTCTTTCCAATGGGGCAAGA ATGTGAGCATTGAGAATCTTCATCAGGGTTTCACTCAT ATTTTTGAATCTACCTTTGAGAGCACAGAGGGTGTTGC AGAGTATGTAGCTCATCCGGCACATGTTGAATACGCA AACTTGTTCCTGGCCAACTTGGAGAAAGTTCTCGTGAT TGACTACAAACCGACAACAGTACGTGTCTGA (SEQ ID NO: 18) |
| CsSAMP3 | *Citrus sinensis* | MEEAKGVVKHVLLAKF KEGTAQDQIDQLIKDYA NLVNLIEPMKSFQWGK DVSIENRHQGFTHIFEST FESTEGVAEYVAHPAH | ATGGAAGAAGCTAAAGGAGTGGTGAAGCACGTACTTC TGGCCAAGTTCAAAGAAGGGACTGCTCAAGATCAAAT TGATCAGCTCATCAAAGACTATGCAAATCTTGTGAAT CTCATTGAACCCATGAAGTCTTTCCAATGGGGCAAGA ATGTGAGCATTGAGAATCTTCATCAGGGTTTCACTCAT |

TABLE 1-continued

| SAMP | Plant Source | Amino Acid Sequence | Nucleic Acid Sequence |
|---|---|---|---|
| | | VEYANLFLANLEKVLVI DYKPTTVRV (SEQ ID NO: 6) | ATTTTTGAATCTACCTTTGAGAGCACAGAGGGTGTTGC AGAGTATGTAGCTCATCCGGCACATGTTGAATACGCA AACTTGTTCCTGGCCAACTTGGAGAAAGTTCTCGTGAT TGACTACAAACCGACAACAGTACGTGTCTGA (SEQ ID NO: 19) |
| CsSAMP4 | *Citrus sinensis* | MGEGEEAAMGEFKHLV IVKFKEGVVVEDIVKG MKKLVSEIDAVKSFEW GQDVEGQEMLRQGFTH AFLMTENKKEDYTTFAS HPSHVEFSATFSAAIEKI VLLDFPTVLGKAPAA (SEQ ID NO: 7) | ATGGGTGAGGGTGAAGAGGCAGCAATGGGAGAGTTC AAGCACTTGGTGATTGTTAAGTTCAAGGAAGGTGTGG TTGTGGAGGATATTGTCAAAGGGATGAAAAAGCTGGT TTCAGAGATTGATGCTGTCAAATCTTTTGAATGGGGCC AAGATGTAGAAGGGCAGGAGATGCTTAGGCAAGGCT TCACACATGCATTCTTGATGACATTCAACAAGAAGGA AGACTATACAACCTTGCAAGCCATCCCAGCCACGTC GAATTCTCGGCTACATTTTCAGCTGCTATTGAGAAGAT TGTCCTGCTTGATTTCCCTACCGTGCTTGGCAAAGCAC CAGCAGCATGA (SEQ ID NO: 20) |
| CcSAMP1 | *Citrus clementina* | MKAETKGRDMEEAKG VVKHVLLAKFKEGTAQ DQIDQLIKDYANLVNLI EPMKSFQWGKDVSIEN LHQGFTHIFESTFESTEG VAEYVAHPAHVEYANL FLANLEKVLVIDYKPTT VRV (SEQ ID NO: 8) | ATGAAAGCCGAAACAAAAGGCAGAGATATGGAAGAA GCTAAAGGAGTGGTGAAGCACGTACTTCTGGCCAAGT TCAAAGAAGGGACTGCTCAAGATCAAATTGATCAGCT CATCAAAGACTATGCAAATCTTGTGAATCTCATTGAA CCCATGAAGTCTTTCCAATGGGGCAAGGATGTGAGCA TTGAGAATCTTCATCAGGGTTTCACTCATATTTTTGAA TCTACCTTTGAGAGCACAGAGGGTGTTGCAGAGTATG TAGCTCATCCGGCACATGTTGAATACGCAAACTTGTTC CTGGCCAACTTGGAGAAAGTTCTCGTGATTGACTACA AACCGACAACTGTACGTGTCTGA (SEQ ID NO: 21) |
| CaSAMP | *Capsicum annuum* | MSYGRGKDVSTENLQQ GFTHVFESTFDSTEGVA EYVSHPVHVEFANLML PQLEKVLVIDYKPEKVG P (SEQ ID NO: 9) | ATGTCATATGGCAGGGGTAAGGATGTGAGCACAGAG AACCTCAAGGTTTCACTCATGTTTTTGAGTCAAC GTTCGACAGTACAGAAGGTGTTGCAGAGTATGTAAGT CATCCGGTTCATGTTGAATTTGCAAATCTAATGCTTCC TCAGCTGGAGAAAGTCCTCGTCATCGACTACAAACCG GAGAAAGTCGGTCCCTAA (SEQ ID NO: 22) |
| NbSAMP | *Nicotiana benthamiana* | MEGGKVKHILLAKFKD GIPADQIDQLIKQYANL VNLIEPMKAFHWGENV STENFHQGFTHVFESTFD STEGIAEYIDHPAHVEY ANTLLPQLEKVLVIDYK PEKVGP (SEQ ID NO: 10) | ATGGAGGGTGGTAAAGTGAAGCACATATTGCTGGCCA AGTTCAAAGATGGAATTCCAGCAGACCAAATCGACCA ACTGATTAAGCAATATGCTAATCTTGTCAATCTCATCG AACCAATGAAAGCTTTTCATTGGGGTGAGAATGTGAG CATAGAGAACTTCCACCAAGGTTTCACTCATGTTTTTG AGTCAACGTTCGACAGTACAGAAGGAATTGCAGAGTA TATAGATCATCCGGCTCATGTTGAATATGCAAATACA TTGCTTCCTCAGCTGGAGAAAGTCCTTGTCATCGACTA CAAACCAGAGAAAGTTGGTCCC (SEQ ID NO: 23) or ATGGAGGGTGGTAAAGTGAAGCACATATTGCTGGCCA AGTTCAAAGATGGAATTCCAGCAGACCAAATCGACCA ACTGATTAAGCAATATGCTAATCTTGTCAATCTCATCG AACCAATGAAAGCTTTTCATTGGGGTGAGAATGTGAG CATAGAGAACTTCCACCAAGGTTTCACTCATGTTTTTG AGTCAACGTTCGACAGTACAGAAGGAATTGCAGAGTA TATAGATCATCCGGCTCATGTTGAATATGCAAATACA TTGCTTCCTCAGCTGGAGAAAGTCCTTGTCATCGACTA CAAACCAGAGAAAGTTGGTCCCTAA (SEQ ID NO: 32) |
| SlSAMP | *Solanum lycopersicum* | MEGGKGGVVKHILLAK FKDGIPPEQIDQLIKQYA NLVNLVEPMKAFQWG KDVSIENLHQGFTHVFE STFDSLEGVAEYIAHPV HVEYANTLLPQLEKFLI VDYKPQ (SEQ ID NO: 11) | ATGGAGGGTGGCAAAGGAGGAGTTGTGAAGCACATTT TGCTAGCAAAGTTCAAAGATGGGATCCCACCTGAACA GATTGATCAACTCATTAAGCAGTATGCTAATCTTGTCA ATCTTGTTGAACCCATGAAGGCTTTTCAATGGGGTAA GGATGTGAGCATAGAAAATCTTCATCAAGGTTTCACT CATGTTTTCGAGTCTACGTTTGACAGTTTAGAAGGTGT TGCAGAGTATATAGCTCATCCTGTTCATGTTGAATATG CAAATACATTGCTTCCTCAGCTGGAGAAATTCCTTATC GTCGACTACAAACCACAG (SEQ ID NO: 24) or ATGGAGGGTGGCAAAGGAGGAGTTGTGAAGCACATTT TGCTAGCAAAGTTCAAAGATGGGATCCCACCTGAACA GATTGATCAACTCATTAAGCAGTATGCTAATCTTGTCA ATCTTGTTGAACCCATGAAGGCTTTTCAATGGGGTAA GGATGTGAGCATAGAAAATCTTCATCAAGGTTTCACT CATGTTTTCGAGTCTACGTTTGACAGTTTAGAAGGTGT TGCAGAGTATATAGCTCATCCTGTTCATGTTGAATATG CAAATACATTGCTTCCTCAGCTGGAGAAATTCCTTATC GTCGACTACAAACCACAGTAA (SEQ ID NO: 33) |
| SmSAMP | *Solanum melongena* | MNIAVFLPSSCPALPRS KASRPSPPGQFPPLAKN | ATGAATATTGCTGTCTTTCTCCCTTCGTCCTGCCCTGC CCTGCCCCGCTCAAAGGCTTCCCGCCCATCCCCACCCG |

TABLE 1-continued

| SAMP | Plant Source | Amino Acid Sequence | Nucleic Acid Sequence |
|---|---|---|---|
| | | VQLLLVLRSYSSTARA<br>MSLRGENVSIENLHQGF<br>THVFESTFDSVEGIAEYI<br>DHPAHVEYANILLTQLE<br>KVLVIDYKPEKLSP<br>(SEQ ID NO: 12) | GCCAATTTCCGTTCCTAGCCAAGAATGTTCAGCTTCTA<br>CTAGTCTTGAGGTCTTATAGTTCCACCGCTCGTGCTAT<br>GTCACTTAGGGGTGAGAATGTGAGCATAGAGAACCTC<br>CACCAAGGTTTCACTCACGTTTTCGAGTCAACGTTTGA<br>CAGTGTAGAAGGCATTGCAGAGTATATAGATCATCCT<br>GCTCATGTTGAATATGCAAATATATTGCTTACTCAGCT<br>GGAGAAAGTCCTTGTCATCGACTACAAACCAGAGAAA<br>CTCAGCCCCTAA (SEQ ID NO: 25) |
| StSAMP | *Solanum tuberosum* | MEGGKGGVVKHILLAK<br>FKDGIPPEQIDQLIKQYA<br>NLVNLIEPMKAFQWGK<br>DVSIENLHQGFTHVFES<br>TFDSLEGVAEYIAHPVH<br>VEFANTMLPQLEKVLII<br>DYKPQ (SEQ ID<br>NO: 13) | CTCATACAATCAACCAAATAAAGGACCCTTTTCTCTCC<br>ACTATTTTTGCTTGTCTAGTCAAGGAAGAAGAGTGAT<br>AAAATAGAAATGGAGGGTGGTAAAGGAGGAGTGGTG<br>AAGCACATTTTGCTAGCAAAGTTCAAAGATGGGATCC<br>CACCTGAACAAATTGATCAACTCATTAAGCAGTATGC<br>TAATCTTGTCAATCTTATTGAACCCATGAAGGCTTTTC<br>AATGGGGCAAGGATGTGAGCATAGAAAACCTTCACCA<br>AGGTTTCACTCATGTTTTTGAGTCGACGTTTGACAGTT<br>TAGAAGGCGTTGCAGAGTATATAGCTCATCCTGTTCA<br>TGTFGAATTTGCAAATACAATGCTTCCTCAGCTGGAG<br>AAAGTCCTTATCATTGACTACAAACCACAGTAACTCA<br>GTCCCTAAACTGGATTCACAAATTGATGCACTTGATGT<br>AATAGGTATATCAGTTTTACTTTACTGTACTGAAATCC<br>AATAAGAACACAAACTTTTATTAAGGGTGTGTGTCTT<br>GCTTGTTTGCAATTATTGTATTCACTTCGTAGACGCTA<br>ATGCGAGTAACTTATGGTCAGCTTGGGCTGTTTAAACT<br>CGAGGAAGAATGCTCTTCGTTCTTCTCTTCCCAGGGAG<br>AATGAATGATGAACAACATATAAGTGCATCAATAAAC<br>TCAGATTGGTGTTTCCATTTCCT (SEQ ID NO: 26)<br>or<br>ATGGAGGGTGGTAAAGGAGGAGTGGTGAAGCACATT<br>TTGCTAGCAAAGTTCAAAGATGGGATCCCACCTGAAC<br>AAATTGATCAACTCATTAAGCAGTATGCTAATCTTGTC<br>AATCTTATTGAACCCATGAAGGCTTTTCAATGGGGCA<br>AGGATGTGAGCATAGAAAACCTTCACCAAGGTTTCAC<br>TCATGTTTTTGAGTCGACGTTTGACAGTTTAGAAGGCG<br>TTGCAGAGTATATAGCTCATCCTGTTCATGTTGAATTT<br>GCAAATACAATGCTTCCTCAGCTGGAGAAAGTCCTTA<br>TCATTGACTACAAACCACAGTAA (SEQ ID NO: 34) |
| PtSAMP1a | *Ponirus trifoliata* | MCCNRGKNVSIENLHQ<br>GFTHIFESTFESTEGVAE<br>YVAHPAHVEYANSFLA<br>NLEKVLVIDYKPTTVRV<br>(SEQ ID NO: 35) | ATGTGCTGCAACAGGGGCAAGAATGTGAGCATTGAGA<br>ATCTTCATCAGGGTTTCACTCATATTTTTGAATCTACC<br>TTTGAGAGCACAGAGGGTGTTGCAGAGTATGTAGCTC<br>ATCCGGCACATGTTGAATACGCAAACTCGTTCCTGGC<br>CAACTTGGAGAAAGTTCTCGTGATTGACTACAAACCG<br>ACAACAGTACGTGTCTGA (SEQ ID NO: 38) |
| PtSAMP1b | *Ponirus trifoliata* | MCCNRGKNVSIENLHQ<br>GFTHIFESTFESTEGVAE<br>YVAHPAHVEYTNSFLA<br>NLEKVLVIDYKPTTVRV<br>(SEQ ID NO: 36) | ATGTGCTGCAACAGGGGCAAGAATGTGAGCATTGAGA<br>ATCTTCATCAGGGTTTCACTCATATTTTTGAATCTACC<br>TTTGAGAGCACAGAGGGTGTTGCAGAGTATGTAGCTC<br>ATCCGGCACATGTTGAATACACAAACTCGTTCCTGGC<br>CAACTTGGAGAAAGTTCTCGTGATTGACTACAAACCG<br>ACAACAGTACGTGTCTGA (SEQ ID NO: 39) |
| MCaSAMP | *Microcitrus australasica* | MCCNRGKNVSIENLHQ<br>GFTHIFESTFESTEGVAE<br>YVSHPAHVEYANLFLA<br>NLEKVLVIDYKPTTVRV<br>(SEQ ID NO: 37) | ATGTGCTGCAACAGGGGCAAGAATGTGAGTATTGAGA<br>ATCTTCATCAGGGTTTCACTCATATTTTTGAATCTACC<br>TTTGAGAGCACAGAGGGTGTTGCAGAGTATGTATCTC<br>ATCCGGCACATGTTGAATACGCAAACTTGTTCCTCGCC<br>AACTTGGAGAAAGTTCTCGTGATTGACTACAAACCGA<br>CAACAGTACGTGTCTGA (SEQ ID NO: 40) |

Figures 2A, 2B, 2C:
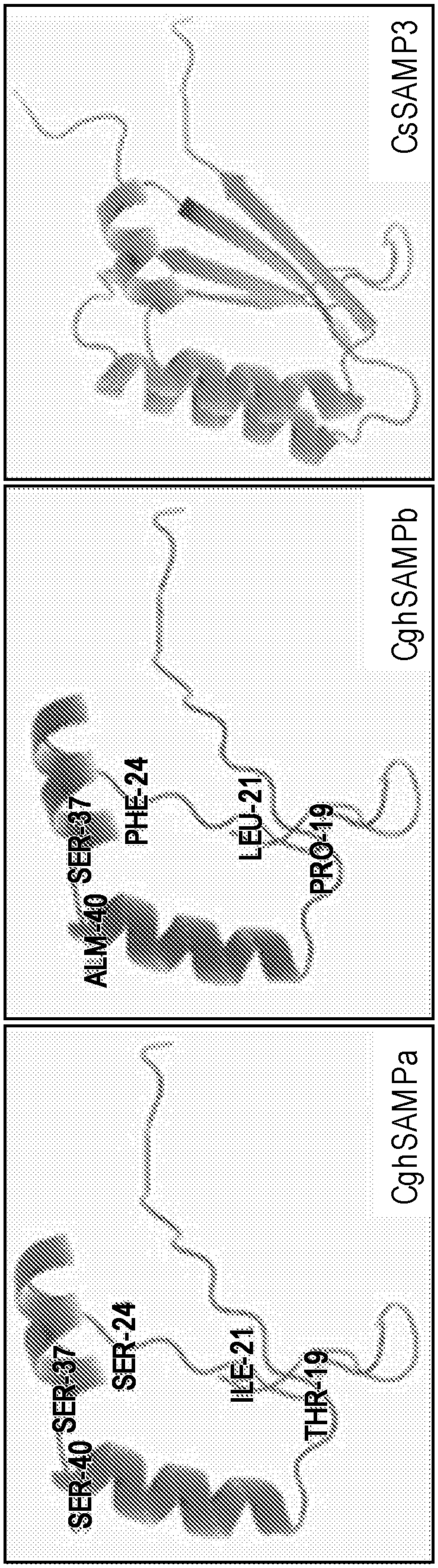
FIGS. 2A-2C are peptide structures showing key amino acids in the loop between two α-helixes of SAMPs. The prediction of peptide structure is performed by Swiss-model with AtSAMP1 as the template (PDB ID: 1Q4R). The sequences of CghSAMPa (also referred to as SAMPa herein) and CghSAMPb (also referred to as SAMPb herein) are shown in Table 1.

Further, SAMPs (e.g., HS peptides) from the *Liberibacter* disease-resistant/tolerant (e.g., HLB-resistant/tolerant) plants contain a few different amino acids within the α-β barrel domain as compared to the corresponding amino acids in the *Liberibacter* disease-susceptible (e.g., HLB-susceptible) plants. Two key amino acid differences between the *Liberibacter* disease-resistant/tolerant (e.g., HLB-resistant/tolerant) plants and the *Liberibacter* disease-susceptible (e.g., HLB-susceptible) plants are identified in the loop between two α-helixes of SAMPs (FIGS. 2A-2C). These two amino acid positions are indicated as bold and underlined in the sequence alignment of SEQ ID NOs:1-13 and 35-37.

```
CghSAMPa  -----------------------------------------MCC-----------NR 5

CghSAMPb  -----------------------------------------MCC-----------NR 5
```

-continued

```
942SAMP1   ---------------------------------------------MCC------------NR 5

CsSAMP1    ---------------------------------------------MCC------------NR 5

CsSAMP2    -------------------------------------MIAELIRSCC----GLELLAVKYK 20

CsSAMP3    ---------MEEAKGVVKHVILAKETEGTAQDQIDQLIKDYANLVN----LIEPMKSFQW 47

CsSAMP4    -----MGEGEEAAMGEFKHLVIVKFKEGVVVEDIVKGMK---KLVS----EIDAVKSFEW 48

CcSA11P1   MKAETKGRDMEEAKGVVKHVLLAKFKEGTAQDQIDQLIKDYANLVN----LIEPMKSFQW 56

CaSANP     ----------------------------------------------------------MSYGR 5

NbSAMP     -----------MEGGKVKHILLAKFKDGIPADQIDQLIKQYANLVN----LIEPMKAFHW 45

S1SANP     --------MEGGKGGVVKHILLAKFKDGIPPEQIDQLIKQYANLVN----LVEPMKAFQW 48

SmSAMP     MNIAV------FLPSSCPALPRSKASRPSPPGQFPFLAKNVQLLLVLRSYSSTARAMSLR 54

StSAMP     --------MEGGKGGVVKHILLAKFKDGIPPEQIDQLIKQYANLVN----LIEPMKAFQW 48

PtSANP1a   ---------------------------------------------MCC------------NR 5

PtSAMP1b   ---------------------------------------------MCC------------NR 5

MCaSAMP    ---------------------------------------------MCC------------NR 5

CghSAMPa   GKNVSI-ENLHQGFTHIFESTFESTEGVAEYVSHPSHVEYANLFLANLEKVLVIDYKPTT 64

CghSAMPb   GKNVSI-ENLHQGFPHLFEFTFESTEGVAEYVSHPAHVEYANLFLANLEKVLVIDYKPTT 64

942SAMP1   GKNVSI-ENLHQGFTHIFESTFESTEGVAEYVAHPAHVEYANLFLANLEKVLVIDYKPTT 64

CsSANP1    GKNVSI-ENLHQGFTHIFESTFESTEGVAEYNAHPAHVEYANLFLANLEKVLVIDYKPTT 64

CsSAMP2    GKNVSI-ENLHQGFTHIFESTFESTEGVAEYVAHPAHVEYANLFLANLEKVLVIDYKPTT 79

CsSAMP3    GKDVSI-ENRHQGFTHIFESTFESTEGVAEYVAHPAHVEYANLFLANLEKVLVIDYKPTT 106

CsSAMP4    GQDVEGQEMLRQGFTHAFLMTFNKKEDYTTFASHPSHVEFSATFSAAIEKIVLLDFPTVL 108

CcSAMP1    GKDVSI-ENLHQGFTHIFESTFESTEGVAEYVAHPAHVEYANLFLANLEKVLVIDYKPTT 115

CaSAMP     GKDVST-ENLQQGFTHVFESTFDSTEGVAEYVSHPVHVEFANLMLPQLEKVLVIDYKPEK 64

NbSAMP     GENVSI-ENFHQGFTHVFESTFDSTEGIAEYIDHPAHVEYANTLLPQLEKVLVIDYKPEK 104

S1SANP     GKDVSI-ENLHQGFTHVFESTFDSLEGVAEYIAHPVHVEYANTLLPQLEKFLIVDYKPQ- 106

SmSAMP     GENVSI-ENLHQGFTHVFESTFDSVEGIAEYIDHPAHVEYANILLTQLEKVLVIDYKPEK 113

StSAMP     GKDVSI-ENLHQGFTHVFESTFDSLEGVAEYIAHPVHVEFANTMLPQLEKVLIIDYKPQ- 106

PtSAMP1a   GKNVSI-ENLHQGFTHIFESTFESTEGVAEYVAHPAHVEYANSFLANLEKVLVIDYKPTT 64

PtSAMP1b   GKNVSI-ENLHQGFTHIFESTFESTEGVAEYVAHPAHVEYTNSFLANLEKVLVIDYKPTT 64

MCaSAMP    GKNVSI-ENLHQGFTHIFESTFESTEGVAEYVSHPAHVEYANLFLANLEKVLVIDYKPTT 64
           *::*.  *  :*** * *  **:. *. : :  ** ***::  :   :**.:::*:

CghSAMPa   VRV--- 67

CghSAMPb   VRV--- 67

9428AMP1   ERV--- 67

CsSAMP1    VRV--- 67

CsSAMP2    VRV--- 82

CsSAMP3    VRV--- 109

CsSAMP4    GKAPAA 114

CcSAMP1    VRV--- 118

CaSAMP     VGP--- 67

NbSAMP     VGP--- 107
```

-continued

```
SlSAMP    ------ 106

SmSAMP    LSP--- 116

StSAMP    ------ 106

PtSAMP1a  VRV--- 67

PtSAMP1b  VRV--- 67

MCaSAMP   VRV--- 67
```

In particular, SAMPs disclosed herein include the following:

*Poncirus trifoliata* Flying Dragon 1, Kryder 55-5, Nanjing (SEQ ID NO: 35)
MCCNRGKNVSIENLHQGFTHIFESTFESTEGVAEYVAHPAHVEYANSFL

ANLEKVLVIDYKPTTVRV

*Poncirus trifoliata* Flying Dragon 2

(SEQ ID NO: 36)
MCCNRGKNVSIENLHQGFTHIFESTFESTEGVAEYVAHPAHVEYTNSFL

ANLEKVLVIDYKPTTVRV

*Microcitrus australasica* and *Poncirus trifoliate* (Texas):

(SEQ ID NO: 37)
MCCNRGKNVSIENLHQGFTHIFESTFESTEGVAEYVSHPAHVEYANLFL

ANLEKVLVIDYKPTTVRV

Australian desert lime *Eremocitrus glauca* 1

(SEQ ID NO: 1)
MCCNRGKNVSIENLHQGFTHIFESTFESTEGVAEYVSHPSHVEYANLFL

ANLEKVLVIDYKPTTVRV

The present disclosure provides isolated stable antimicrobial (e.g., antibacterial) peptides (SAMPs) (e.g., HS peptides) comprising a sequence that is substantially identical (e.g., at least 50%, 55%, 60%, 65%, 70%, 75%, 80%, 85%, 90%, 91%, 92%, 93%, 94% 95%, 96%, 97%, 98%, or 99% identical to) to a sequence of any one of SEQ ID NOs:1-13 and 35-37 (e.g., SEQ ID NOs:1-5 and 9). In some embodiments, the isolated peptides comprise a sequence having at least 75% sequence identity (e.g., at least 80%, 85%, 90%, 91%, 92%, 93%, 94% 95%, 96%, 97%, 98%, or 99% sequence identity) to a sequence of any one of SEQ ID NOs:1-13 and 35-37 (e.g., SEQ ID NOs:1-5 and 9). In particular embodiments, the isolated peptides comprise a sequence having at least 75% sequence identity (e.g., at least 80%, 85%, 90%, 91%, 92%, 93%, 94% 95%, 96%, 97%, 98%, or 99% sequence identity) to a sequence of any one of SEQ ID NOs:1 and 2.

The present disclosure provides isolated SAMPs (e.g., HS peptides) comprising a sequence having at least one amino acid substitution (e.g., 2, 3, 4, 5, 6, 7, 8, 9, 10, 11, 12, 13, 14, or 15 amino acid substitutions) relative to a sequence of any one of SEQ ID NOs:1-13 and 35-37 (e.g., SEQ ID NOs: 1-5 and 9). In particular embodiments, the isolated peptides comprise a sequence having at least one amino acid substitution (e.g., 2, 3, 4, 5, 6, 7, 8, 9, 10, 11, 12, 13, 14, or 15 amino acid substitutions) relative to a sequence of any one of SEQ ID NOs:1 and 2.

Isolated SAMPs (e.g., HS peptides) of the present disclosure may also comprise a sequence of $X_1GX_2X_3VSX_4ENX_5X_6QGFX_7HX_8FEX_9TFX_{10}SX_{11}EGX_{12}AEYX_{13}X_{14}HPX_{15}HVEX_{16}ANX_{17}X_{18}LX_{19}X_{20}LEKX_{21}LX_{22}X_{23}DYKPX_{24}TX_{25}RV$ (SEQ ID NO:27), in which $X_1$ is R, K, or W; $X_2$ is K or E; $X_3$ is N or D; $X_4$ is T or I; $X_5$ is L, F, or R; $X_6$ is H or Q; $X_7$ is P or T; $X_8$ is I, L, or V; $X_9$ is S or F; $X_{10}$ is E or D; $X_{11}$ is T or L; $X_{12}$ is V or I; $X_{13}$ is V or I; $X_{14}$ is S, A, or D; $X_{15}$ is S, A, or V; $X_{16}$ is Y or F; $X_{17}$ is L or T; $X_{18}$ is F, M, or L; $X_{19}$ is A, P, or T; $X_{20}$ is N or Q; $X_{21}$ is V or F; $X_{22}$ is V or I; $X_{23}$ is V or I; $X_{24}$ is T, E, or Q; and $X_{25}$ is V, E, L. In particular embodiments of isolated SAMPs (e.g., HS peptides) comprising a sequence of SEQ ID NO:27, $X_1$ may be R; $X_2$ may be K; $X_3$ may be N; $X_4$ may be I; $X_5$ may be L; $X_6$ may be H; $X_{10}$ may be E; $X_{11}$ may be T; $X_{12}$ may be V; $X_{13}$ may be V; $X_{16}$ may be Y; $X_{17}$ may be L; $X_{18}$ may be F; $X_{19}$ may be A; $X_{20}$ may be N; $X_{21}$ may be V; $X_{22}$ may be V, $X_{23}$ may be I; and/or $X_{24}$ may be T.

In certain embodiments, the disclosure also provides methods of producing a plant (e.g., a *citrus* plant) having enhanced *Liberibacter* disease resistance (e.g., HLB resistance) or *Liberibacter* disease tolerance (e.g., HLB tolerance) (i.e., enhanced resistance or tolerance to a bacterial infection caused by bacteria in the genus *Liberibacter* (e.g., *Candidatus Liberibacter* species) or *Liberibacter crescens*) by introducing a mutation into a polynucleotide in the plant, in which the mutated polynucleotide encodes a SAMP of the present disclosure, such as the SAMPs described above (e.g., SAMPs having at least 75% sequence identity (e.g., at least 80%, 85%, 90%, 91%, 92%, 93%, 94% 95%, 96%, 97%, 98%, or 99% sequence identity) or at least one amino acid substitution (e.g., 2, 3, 4, 5, 6, 7, 8, 9, 10, 11, 12, 13, 14, or 15 amino acid substitutions) relative to the sequence of any one of SEQ ID NOs:1-13 and 35-37 (e.g., SEQ ID NOs: 1-5 and 9). In particular, the mutated polynucleotide may encode a SAMP having at least 75% sequence identity (e.g., at least 80%, 85%, 90%, 91%, 92%, 93%, 94% 95%, 96%, 97%, 98%, or 99% sequence identity) or at least one amino acid substitution (e.g., 2, 3, 4, 5, 6, 7, 8, 9, 10, 11, 12, 13, 14, or 15 amino acid substitutions) relative to the sequence of any one of SEQ ID NOs:1 and 2.

In other embodiments, methods of producing a plant (e.g., a *citrus* plant) having enhanced *Liberibacter* disease resistance (e.g., HLB resistance) or *Liberibacter* disease tolerance (e.g., HLB tolerance) (i.e., enhanced resistance or tolerance to a bacterial infection caused by bacteria in the genus *Liberibacter* (e.g., *Candidatus Liberibacter* species) or *Liberibacter crescens*) may be achieved by introducing one or more mutations into a polynucleotide in the plant, in which the mutations specifically alter the amino acids in the native SAMP in the plant that correspond to the two bold and underlined amino acids in the sequence alignment shown above. For example, the positions in a polynucleotide sequence encoding a native SAMP in a plant that correspond to the two bold and underlined amino acids in the sequence alignment shown above may be mutated to encode S, A, or D as the first of two bold and underlined amino acids and S, A, or V as the second of the two bold and underlined amino acids.

In some embodiments, one of skill in the art may perform sequence alignment of a polynucleotide sequence encoding a native SAMP in a plant and a polynucleotide sequence encoding an effective SAMP (e.g., SEQ ID NO: 14 or 15) to determine specific nucleic acids in the polynucleotide of the plant that need to be mutated such that the resulting mutated polynucleotide in the plant encodes the substantially the same polynucleotide sequence as that of an effective SAMP (e.g., SEQ ID NO: 14 or 15).

The disclosure also provides methods of preventing or treating a *Liberibacter* disease (e.g., HLB) and/or preventing or treating a bacterial infection caused by bacteria in the genus *Liberibacter* (e.g., *Candidatus Liberibacter* species or *Liberibacter crescens*) in a plant by contacting the plant with a SAMP described above (e.g., SAMPs having at least 75% sequence identity to or at least one amino acid substitution relative to the sequence of any one of SEQ ID NOs:1-13 and 35-37 (e.g., SEQ ID NOs:1-5 and 9 (e.g., SEQ ID NOT and 2)). Without being bound by any theory, SAMPs (e.g., HS peptides) may target and destroy bacterial cells, and/or induce defense response in plants, thus, enhancing the *Liberibacter* disease resistance or *Liberibacter* disease tolerance of plants. An example of a bacterial infection caused by bacteria in the genus *Liberibacter* (e.g., *Candidatus Liberibacter* species or *Liberibacter crescens*) that can be treated or prevented as described herein is potato zebra chip disease. For example, potato zebra disease can be treated or prevented in potato or tomato plants.

III. Agricultural Compositions

The disclosure also provides agricultural compositions that contain one or more of the SAMPs (e.g., HS peptides) described herein for use in preventing or treating a bacterial disease (e.g., a *Liberibacter* disease (HLB) or potato Zebra Chip disease, and other bacterial diseases such as those caused by *Agrobacterium tumefaciens* (also known as *Rhizobium radiobacter*) and *Pseudomonas syringae*) in a plant. In some embodiments, the agricultural composition further includes at least one of an herbicide, an herbicide safener, a surfactant, a fungicide, a pesticide, a nematicide, a plant activator, a synergist, a plant growth regulator, an insect repellant, an acaricide, a molluscicide, or a fertilizer.

An agricultural composition comprising one or more SAMPs (e.g., HS peptides) described herein can also include one or more of: a surface-active agent, an inert carrier, a preservative, a humectant, a feeding stimulant, an attractant, an encapsulating agent, a binder, an emulsifier, a dye, a UV protective, a buffer, a flow agent, a fertilizer, a nitrogen fixation agent, micronutrient donors, or other preparations that influence plant growth. The agricultural composition can also include one or more agrochemicals including: herbicides, insecticides, fungicides, bactericides, nematicides, molluscicides, acaracides, plant growth regulators, harvest aids, and fertilizers, which can also be combined with carriers, surfactants or adjuvants as appropriate for the agrochemical. Suitable carriers and adjuvants can be solid or liquid and correspond to the substances ordinarily employed in formulation technology, e.g., natural or regenerated mineral substances, solvents, dispersants, wetting agents, tackifiers, binders, or fertilizers. The active ingredients of the present disclosure are normally applied in the form of compositions and can be applied to the crop area, plant, or seed to be treated. For example, the compositions of the present disclosure may be applied during growth, seeding, or storage.

Surface-active agents that can be used with the presently described SAMPs (e.g., HS peptides) include anionic compounds such as a carboxylate of, for example, a metal; carboxylate of a long chain fatty acid; an N-acylsarcosinate; mono- or di-esters of phosphoric acid with fatty alcohol ethoxylates or salts of such esters; fatty alcohol sulfates such as sodium dodecyl sulfate, sodium octadecyl sulfate or sodium cetyl sulfate; ethoxylated fatty alcohol sulfates; ethoxylated alkylphenol sulfates; lignin sulfonates; petroleum sulfonates; alkyl aryl sulfonates such as alkyl-benzene sulfonates or lower alkylnaphtalene sulfonates, e.g., butyl-naphthalene sulfonate; salts of sulfonated naphthalene-formaldehyde condensates; salts of sulfonated phenol-formaldehyde condensates; more complex sulfonates such as the amide sulfonates, e.g., the sulfonated condensation product of oleic acid and N-methyl taurine; or the dialkyl sulfosuccinates, e.g., the sodium sulfonate or dioctyl succinate. Non-ionic agents include condensation products of fatty acid esters, fatty alcohols, fatty acid amides or fatty-alkyl- or alkenyl-substituted phenols with ethylene oxide, fatty esters of polyhydric alcohol ethers, e.g., sorbitan fatty acid esters, condensation products of such esters with ethylene oxide, e.g., polyoxyethylene sorbitar fatty acid esters, block copolymers of ethylene oxide and propylene oxide, acetylenic glycols such as 2,4,7,9-tetraethyl-5-decyn-4,7-diol, or ethoxylated acetylenic glycols. Examples of a cationic surface-active agent include, for instance, an aliphatic mono-, di-, or polyamine such as an acetate, naphthenate or oleate; or oxygen-containing amine such as an amine oxide of polyoxyethylene alkylamine; an amide-linked amine prepared by the condensation of a carboxylic acid with a di- or polyamine; or a quaternary ammonium salt.

Examples of inert materials or inert carriers that can be used include, but are not limited to, inorganic minerals such as kaolin, phyllosilicates, carbonates, sulfates, phosphates, or botanical materials such as cork, powdered corncobs, peanut hulls, rice hulls, and walnut shells.

Herbicides that can be used with the presently described SAMPs (e.g., HS peptides) include compounds that kill or inhibit growth or replication of undesired plants, typically a subset of plants that is distinct from the desired plant or crop. There are several modes of action: ACCase inhibition, carotenoid biosynthesis inhibition, cell wall synthesis inhibition, ALS inhibition, ESP synthase inhibition, glutamine synthase inhibition, HPPD inhibition, microtubule assembly inhibition, PPO inhibition, etc. Examples of commercially available herbicides include One-Time®, MSMA, Corvus®, Volunteer®, Escalade®, Q4®, Raptor®, Acumen®, Sencor®, Bullet®, TopNotch®, Valor®, PastureGard®, glycophosate (Roundup®), DSMA, Break-Up®, Hyvar®, Barricade®, etc. Herbicides can be mixed with "herbicide safeners" to reduce general toxicity of the herbicide, as described, e.g., in Riechers et al. (2010) *Plant Physiol.* 153:3.

Pesticides (e.g., nematicides, molluscicides, insecticides, miticide/acaricides) can be used in combination with the presently disclosed SAMPs (e.g., HS peptides) to kill or reduce the population of undesirable pests affecting the plant. Pesticides can also be used with repellants or pheromones to disrupt mating behavior. Insectides are directed to insects, and include, e.g., those of botanical origin (e.g., allicin, nicotine, oxymatrine, jasmolin I and II, quassia, rhodojaponin III, and limonene), carbamate insecticides (e.g., carbaryl, carbofuran, carbosulfan, oxamyl, nitrilacarb, CPMC, EMPC, fenobucarb), fluorine insecticides, formamidine insecticides, fumigants (e.g., ethylene oxide, methyl bromide, carbon disulfide), chitin synthesis inhibitors, macrocyclic lactone insecticides, neonicotinoid insecticides, organophosphate insectides, urea and thiourea insecticides, etc. Nematicides affect nematodes, and include, e.g., organophosphorus nematicides (e.g., diamidafos, fosthiazate, heterophos, phsphamidon, triazophos), fumigant nematicides (e.g., carbon disulfide, methyl bromide, methyl iodide), abamectin, carvacrol, carbamate nematicides (e.g., benomyl, oxamyl), etc. Molluscicides are directed to slugs and snails, and include, e.g., allicin, bromoacetamide, thiocarb, trifenmorph, fentin, copper sulfate, etc. Many pesticides target more than one type of pest, so that one or two can be selected to target insects, mollusks, nematodes, mitogens, etc.

Fertilizers typically provide macro- and micronutrients in a form that they can be utilized by the plant, or a plant-associated organism. These include, e.g., nitrogen, phosphorus, potassium, sulfur, calcium, potassium, boron, chlorine, copper, iron, manganese, molybdenum, zinc, nickel, and selenium. Fertilizers are often tailored to specific soil conditions or for particular crops or plants. Fertilizers that can be used include naturally-occurring, modified, concentrated and/or chemically synthesized materials, e.g., manure, bone meal, compost, fish meal, wood chips, etc., or can be chemically synthesized, UAN, anhydrous ammonium nitrate, urea, potash, etc. Suppliers include Scott®, Sure-Crop®, BCF®, RVR®, Gardenline®, and many others known in the art.

Fungicides are compounds that can kill fungi or inhibit fungal growth or replication. Fungicides that can be used with the presently disclosed SAMPs (e.g., HS peptides) include contact, translaminar, and systemic fungicides. Examples include sulfur, neem oil, rosemary oil, jojoba, tea tree oil, *Bacillus subtilis*, Ulocladium, cinnamaldehyde, etc.

The agricultural compositions of the disclosure can be in a suitable form for direct application or as a concentrate of primary composition that requires dilution with a suitable quantity of water or other diluent before application. The concentration of the SAMP (e.g., an HS peptide) in the agricultural composition will vary depending upon the nature of the particular formulation, specifically, whether it is a concentrate or to be used directly, the type of plant, and in some cases, on the nature of the use, e.g., for preventing a plant that is at risk of a *Liberibacter* disease (e.g., HLB) or for treating a plant that is already infected with a *Liberibacter* disease (e.g., HLB).

IV. Methods of Preventing or Treating a Bacterial Disease

As described herein, SAMPs may be used to prevent or treat a bacterial disease, e.g., a Gram-negative bacterial disease. A *Liberibacter* disease refers to an infection caused by Gram-negative bacteria in the genus *Liberibacter* (e.g., *Candidatus Liberibacter* species or *Liberibacter crescens*). A *Liberibacter* disease may infect plants such as *citrus* plants (e.g., orange, grapefruit, tangerine, lemon, line, key line, papeda, citron, and pomelo) and solanaceous plants (e.g., potato, tomato, eggplant, and pepper). Huanglongbing (HLB) is a type of *Liberibacter* disease that infects *citrus* plants. Potato Zebra Chip (ZC) disease is a type of *Liberibacter* disease that infects potato plants. The infection is vectored and transmitted by potato psyllids (e.g., *Bactericera cockerelli*). The methods of utilizing the SAMPs disclosed herein may also be used to prevent or treat other bacterial diseases (e.g., other Gram-negative bacterial diseases), such as those caused by *Agrobacterium tumefaciens* (also known as *Rhizobium radiobacter*) and *Pseudomonas syringae*.

HLB

The present disclosure also provides methods of preventing or treating HLB in plants. In some embodiments of the methods, the plants with HLB may be contacted with a SAMPs (e.g., an HS peptide) described herein (e.g., a SAMP comprising at least 75% sequence identity to the sequence of SEQ ID NO:1 or 2) or an agricultural composition comprising one or more SAMPs (e.g., HS peptides) described herein. In some embodiments, the SAMP or agricultural composition may be injected into the trunk of the plant. In other embodiments, the SAMP or agricultural composition may be injected into the stem of the plant. In yet other embodiments, the SAMP or agricultural composition may be foliar sprayed onto the plant. In yet other embodiments, the SAMP or agricultural composition may be applied by dripping irrigation to the plant. Once the plants are contacted with the SAMPs (e.g., HS peptides) described herein, the peptides may enhance HLB resistance or HLB tolerance of the plants, thus, preventing or treating HLB in the plants.

The methods described herein can be used to reduce symptoms caused by HLB, including yellowing of leaves, blotchy mottle of the leaves, zinc-deficiency-like mottle, severe chlorosis, and reduced fruit yield. It will be understood that symptoms of HLB vary according to the time of infection, stage of the disease, tree species, and tree maturity, among other things. It will be further understood that in some embodiments, the disclosed methods may not necessarily result in eradication or cure of the infection but can significantly reduce the symptoms caused by HLB.

Thus, in some embodiments, the methods provided herein reduce the symptoms of HLB by reducing the yellowing of leaves, resulting in a greener appearance, increasing the growth rate of the plant, and/or increasing the fruit yield of the plant. Thus, in some embodiments, the fruit yield is improved by 5%, 10%, 20%, 30%, 40%, 50%, 60% 70%, 80%, 90%, 100%, 200%, 500% or more compared to a plant that is not treated according to the methods. In some embodiments, the fruit yield is increased to 10%, 20%, 30%, 40%, 50%, 60%, 70%, 80%, 90%, or 100% of the yield of a similar plant that was not infected by HLB.

The methods described herein may also be used to prevent HLB-infection in plants. For example, a plant that is not yet infected with HLB, but is at risk for infection (i.e., the plant is located in an area where HLB is identified in surrounding plants) may be contacted by one or more SAMPs (e.g., HS peptides) as described in the methods of the disclosure. The plant at risk for HLB may also be genetically modified to express one or more SAMPs (e.g., HS peptides) described herein to prevent HLB.

Potato ZC Disease

The present disclosure also provides methods of preventing or treating potato ZC disease in potato plants. In some embodiments of the methods, the plants with potato ZC disease may be contacted with a SAMP (e.g., an HS peptide) described herein (e.g., a SAMP comprising at least 75% sequence identity to the sequence of SEQ ID NOT or 2) or an agricultural composition comprising one or more SAMPs (e.g., HS peptides) described herein. In some embodiments, the SAMP or agricultural composition may be injected into the tuber of the plant. In other embodiments, the SAMP or agricultural composition may be applied to the roots of the plants. In yet other embodiments, the SAMP or agricultural composition may be foliar sprayed onto the plant. Once the plants are contacted with the SAMPs (e.g., HS peptides) described herein, the peptides may enhance potato ZC disease resistance or potato ZC disease tolerance of the plants, thus, preventing or treating potato ZC disease in the plants.

The methods described herein can be used to reduce symptoms caused by potato ZC disease, including chlorosis, leaf scorching, swollen nodes, vascular tissue browning, curled leaves, collapsed stolons, enlarged lenticels, vascular tissue browning, medullary ray discoloration, and necrotic flecking of tuber tissue. It will be understood that symptoms of potato ZC disease vary according to the time of infection, stage of the disease, plant species, and maturity, among other things. It will be further understood that in some embodiments, the disclosed methods may not necessarily result in eradication or cure of the infection, but can significantly reduce the symptoms caused by potato ZC disease.

Thus, in some embodiments, the methods provided herein reduce the symptoms of potato ZC disease as described above, resulting in a more healthy appearance, increasing the growth rate of the plant, and/or increasing the yield of the plant. Thus, in some embodiments, the yield is improved by 5%, 10%, 20%, 30%, 40%, 50%, 60% 70%, 80%, 90%, 100%, 200%, 500% or more compared to a plant that is not treated according to the methods. In some embodiments, the yield is increased to 10%, 20%, 30%, 40%, 50%, 60%, 70%, 80%, 90%, or 100% of the yield of a similar plant that was not infected by potato ZC disease.

The methods described herein may also be used to prevent potato ZC disease-infection in plants. For example, a plant that is not yet infected with potato ZC disease, but is at risk for infection (i.e., the plant is located in an area where potato ZC disease is identified in surrounding plants) may be contacted by one or more SAMPs (e.g., HS peptides) as described in the methods of the disclosure. The plant at risk for potato ZC disease may also be genetically modified to express one or more SAMPs (e.g., HS peptides) described herein to prevent potato ZC disease.

V. Production of Plants Comprising SAMPs

In another aspect, the present disclosure provides for transgenic plants comprising recombinant expression cassettes for expressing a SAMP (e.g., an HS peptide) as described herein in a plant. In some embodiments, a transgenic plant is generated that contains a complete or partial sequence of a polynucleotide that is derived from a species other than the species of the transgenic plant. It should be recognized that transgenic plants encompass the plant or plant cell in which the expression cassette is introduced as well as progeny of such plants or plant cells that contain the expression cassette, including the progeny that have the expression cassette stably integrated in a chromosome.

A recombinant expression vector comprising a SAMP (e.g., an HS peptide) coding sequence driven by a heterologous promoter may be introduced into the genome of the desired plant host by a variety of conventional techniques. For example, the DNA construct may be introduced directly into the genomic DNA of the plant cell using techniques such as electroporation and microinjection of plant cell protoplasts, or the DNA construct can be introduced directly to plant tissue using ballistic methods, such as DNA particle bombardment. An exemplary vector is a viral vector that can express and optionally replicate in the plant. Exemplary viral vectors can include, for example, *citrus* tristeza vims (CTV) for expressing the peptide in a phloem-limited manner in *citrus*, or tobacco rattle virus (TRV) to express the antimicrobial peptides in potato or other plants. Alternatively, the DNA construct may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. While transient expression of the constitutively active SAMP is encompassed by the disclosure, generally, expression of a construct of the disclosure will be from insertion of expression cassettes into the plant genome, e.g., such that at least some plant offspring also contain the integrated expression cassette.

Microinjection techniques are also useful for this purpose. These techniques are well known in the art and thoroughly described in the literature. The introduction of DNA constructs using polyethylene glycol precipitation is described in Paszkowski et al. *EMBO J.* 3:2717-2722 (1984). Electroporation techniques are described in Fromm et al. *Proc. Natl. Acad Sci. USA* 82:5824 (1985). Ballistic transformation techniques are described in Klein et al. *Nature* 327:70-73 (1987).

*Agrobacterium tumefaciens*-mediated transformation techniques, including disarming and use of binary vectors, are well described in the scientific literature. See, for example, Horsch et al. *Science* 233:496-498 (1984), and Fraley et al. *Proc. Natl. Acad. Sci. USA* 80:4803 (1983).

Transformed plant cells derived by any of the above transformation techniques can be cultured to regenerate a whole plant that possesses the transformed genotype and thus the desired phenotype, e.g., resistance or tolerance to a *Liberibacter* disease (e.g., HLB). Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al., Protoplasts Isolation and Culture, Handbook of Plant Cell Culture, pp. 124-176, MacMillilan Publishing Company, New York, 1983; and Binding, Regeneration of Plants, Plant Protoplasts, pp. 21-73, CRC Press, Boca Raton, 1985. Regeneration can also be obtained from plant callus, explants, organs, or parts thereof. Such regeneration techniques are described generally in Klee et al. *Ann. Rev. of Plant Phys.* 38:467-486 (1987).

One of skill in the art will recognize that after the expression cassette is stably incorporated in transgenic plants and confirmed to be operable, it can be introduced into other plants by sexual crossing. Any of a number of standard breeding techniques can be used, depending upon the species to be crossed.

The expression cassettes and other constructs of the disclosure can be used to confer *Liberibacter* disease resistance or tolerance on essentially any plant. Thus, the disclosure has use over a broad range of plants, including species from the genus *Citrus* (e.g., *Citrus maxima, Citrus medica, Citrus micrantha, Citrus reticulate, Citrus aurantiifolia, Citrus aurantium, Citrus latifolia, Citrus limon, Citrus limonia, Citrus paradise, Citrus sinensis*, and *Citrus tangerine*) or species from the family Solanaceae (e.g., *Solanum* spp., *Capsicum* spp., and *Nicotiana* spp.). Species from the genus *Solanum* include, e.g., *Solanum tuberosum, Solanum lycopersicum, Solanum melongena, Solanum aviculare, Solanum capsicastrum, Solanum crispum, Solanum laciniatum, Solanum laxum, Solanum pseudocapsicum, Solanum rantonnetii, Solanum seaforthianum*, and *Solanum wendlandii*. Species from the genus *Capsicum* include, e.g., *Capsicum annuum, Capsicum baccatum, Capsicum campylopodium, Capsicum cardenasii, Capsicum chacoense, Cap-*

*sicum cornutum, Capsicum dusenii, Capsicum eximium, Capsicum friburgense, Capsicum frutescens, Capsicum geminifolium, Capsicum havanense, Capsicum lanceolatum, Capsicum lycianthoides, Capsicum minutiflorum, Capsicum mositicum, Capsicum pubescens, Capsicum recurvatum, Capsicum schottianum, Capsicum spina-alba, Capsicum tovarii*, and *Capsicum villosum*. Species from the genus *Nicotiana* include, e.g., *Nicotiana acuminate, Nicotiana benthamiana, Nicotiana glauca, Nicotiana longiflora, Nicotiana rustica, Nicotiana tabacum*, and *Nicotiana occidentalis.*

In particular embodiments, the plant is selected from the group consisting of *Citrus reticulata, Citrus sinensis, Citrus Clementina, Capsicum annuum, Solanum tuberosum, Solanum lycopersicum, Solanum melongena*, and *Nitotiana benthamiana*. In particular embodiments, the plant is a sweet orange plant (*Citrus sinensis*). In particular embodiments, the plant is a clementine plant (*Citrus clementina*). In particular embodiments, the plant is a potato plant (*Solanum tuberosum*). In some embodiment, the plant is a vegetable- or fruit-producing plant.

Those of skill will recognize that a number of plant species can be used as models to predict the phenotypic effects of transgene expression in other plants. For example, it is well recognized that both tobacco (*Nicotiana*) and *Arabidopsis* plants are useful models of transgene expression, particularly in other dicots.

In some embodiments, the plants of the disclosure have enhanced SAMP-mediated phenotypes, for example enhanced bacterial disease (e.g., a *Liberibacter* disease (e.g., HLB and ZC) and other bacterial diseases such as those caused by *Agrobacterium tumefaciens* (also known as *Rhizobium radiobacter*) and *Pseudomonas syringae*) resistance or tolerance, as compared to plants that are otherwise identical except for expression of the SAMP.

CRISPR/Cas

Plant gene manipulations can now be precisely tailored in non-transgenic organisms using the CRISPR/Cas9 genome editing method. In this bacterial antiviral and transcriptional regulatory system, a complex of two small RNAs—the CRISPR-RNA (crRNA) and the trans-activating crRNA (tracrRNA)—directs the nuclease (Cas9) to a specific DNA sequence complementary to the crRNA (Jinek, M., et al. *Science* 337, 816-821 (2012)). Binding of these RNAs to Cas9 involves specific sequences and secondary structures in the RNA. The two RNA components can be simplified into a single element, the single guide-RNA (sgRNA), which is transcribed from a cassette containing a target sequence defined by the user (Jinek, M., et al. *Science* 337, 816-821 (2012)). This system has been used for genome editing in humans, zebrafish, *Drosophila*, mice, nematodes, bacteria, yeast, and plants (Hsu, P. D., et al., *Cell* 157, 1262-1278 (2014)). In this system the nuclease creates double stranded breaks at the target region programmed by the sgRNA. These can be repaired by non-homologous recombination, which often yields inactivating mutations. The breaks can also be repaired by homologous recombination, which enables the system to be used for gene targeted gene replacement (Li, J.-F., et al. *Nat. Biotechnol.* 31, 688-691, 2013; Shan, Q., et al. *Nat. Biotechnol.* 31, 686-688, 2013). In some embodiments of the methods in the present disclosure, a gene encoding a wild-type or endogenous SAMP in a plant may be modified using the CAS9/CRISPR system to match the polynucleotide sequence encoding a SAMP described herein (e.g., a polynucleotide sequence encoding the SAMP having at least 75% sequence identity or at least one amino acid substitution relative to the sequence of any one of SEQ ID NOs:1-13 and 35-37 (e.g., SEQ ID NOs:1 and 2)). In some embodiments, a gene encoding a wild-type or endogenous SAMP in a plant may be modified using the CAS9/CRISPR system to match the polynucleotide sequence of any one of SEQ ID NOs: 14-26, 28-34, and 38-40 (e.g., SEQ ID NO: 14 and 15).

Accordingly, in some embodiments, instead of generating a transgenic plant, a native SAMP coding sequence in a plant or plant cell can be altered in situ to generate a plant or plant cell carrying a polynucleotide encoding a SAMP described herein (e.g., a SAMP having at least 75% sequence identity or at least one amino acid substitution relative to the sequence of any one of SEQ ID NOs: 1-13 and 35-37 (e.g., SEQ ID NOs:1 and 2)). For example, in some embodiments, CRISPR technology is used to introduce one or more nucleotide changes into a SAMP coding sequence in situ to change the appropriate codon to make a change corresponding to positions $X_1$ to $X_{25}$ as set forth in the sequence of SEQ ID NO:27. The CRISPR/Cas system has been modified for use in prokaryotic and eukaryotic systems for genome editing and transcriptional regulation. The "CRISPR/Cas" system refers to a widespread class of bacterial systems for defense against foreign nucleic acid. CRISPR/Cas systems are found in a wide range of eubacterial and archaeal organisms. CRISPR/Cas systems include type I, II, and III sub-types. Wild-type type II CRISPR/Cas systems utilize the RNA-mediated nuclease, Cas9 in complex with guide and activating RNA to recognize and cleave foreign nucleic acid. Cas9 homologs are found in a wide variety of eubacteria, including, but not limited to bacteria of the following taxonomic groups: Actinobacteria, Aquificae, Bacteroidetes-Chlorobi, Chlamydiae-Verrucomicrobia, Chlroflexi, Cyanobacteria, Firmicutes, Proteobacteria, Spirochaetes, and Thermotogae. An exemplary Cas9 protein is the *Streptococcus pyogenes* Cas9 protein. Additional Cas9 proteins and homologs thereof are described in, e.g., Chylinksi, et al., RNA Biol. 2013 May 1; 10(5): 726-737; Nat. Rev. Microbiol. 2011 June; 9(6): 467-477; Hou, et al., Proc Natl Acad Sci USA. 2013 Sep. 24; 110(39):15644-9; Sampson et al., Nature. 2013 May 9; 497(7448):254-7; and Jinek, et al., Science. 2012 Aug. 17; 337(6096):816-21.

Accordingly, in one aspect, a method is provided of using CRISPR/CAS9 to introduce at least one mutation into a plant cell is performed. In some embodiments, a method of altering a (e.g., native) nucleic acid encoding SAMP in a plant is provided. In some embodiments, the method comprises introducing into the plant cell containing and expressing a DNA molecule having a target nucleic acid encoding SAMP an engineered, non-naturally occurring Clustered Regularly Interspaced Short Palindromic Repeats (CRISPR)-CRISPR associated (Cas) (CRISPR-Cas) system. In some embodiments, the CRISPR-Cas system comprises one or more vectors comprising: a) a first regulatory element operable in a plant cell operably linked to at least one nucleotide sequence encoding a CRISPR-Cas system guide RNA that hybridizes with the target sequence, and b) a second regulatory element operable in a plant cell operably linked to a nucleotide sequence encoding a Type-II Cas9 protein, wherein components (a) and (b) are located on same or different vectors of the system, whereby the guide RNA targets the target sequence and the Cas9 protein cleaves the DNA molecule, whereby at least one mutation is introduced into the target nucleic acid encoding the SAMP, i.e., one or more mutations are introduced into the target nucleic acid encoding the SAMPs to alter the sequence of the target nucleic acid to match the polynucleotide sequence encoding an antimicrobial (e.g., antibacterial) peptide having the sequence of any one of SEQ ID NOs:1-13 and 35-37 (e.g., SEQ ID NOs:1 and 2). In some embodiments, the SAMP is selected from any of SEQ ID NOs:1-5 and 9, or a substantially identical polypeptide thereof.

In some embodiments, methods of using CRISPR/CAS9 technology to introduce at least one mutation into a (e.g., native) nucleic acid encoding SAMP may be applied to a broad range of plants, including species from the genus *Citrus* (e.g., *Citrus maxima, Citrus medica, Citrus micrantha, Citrus reticulate, Citrus aurantiifolia, Citrus aurantium, Citrus latifolia, Citrus limon, Citrus limonia, Citrus paradise, Citrus sinensis*, and *Citrus tangerine*) or species from the family Solanaceae (e.g., *Solanum* spp., *Capsicum* spp., and *Nicotiana* spp.). Species from the genus *Solanum* include, e.g., *Solanum tuberosum, Solanum lycopersicum, Solanum melongena, Solanum aviculare, Solanum capsicastrum, Solanum crispum, Solanum laciniatum, Solanum laxum, Solanum pseudocapsicum, Solanum rantonnetii, Solanum seaforthianum*, and *Solanum wendlandii*. Species from the genus *Capsicum* include, e.g., *Capsicum annuum, Capsicum baccatum, Capsicum campylopodium, Capsicum cardenasii, Capsicum chacoense, Capsicum cornutum, Capsicum dusenii, Capsicum eximium, Capsicum friburgense, Capsicum frutescens, Capsicum geminifolium, Capsicum havanense, Capsicum lanceolatum, Capsicum lycianthoides, Capsicum minutiflorum, Capsicum mositicum, Capsicum pubescens, Capsicum recurvatum, Capsicum schottianum, Capsicum spina-alba, Capsicum tovarii*, and *Capsicum villosum*. Species from the genus *Nicotiana* include, e.g., *Nicotiana acuminate, Nicotiana benthamiana, Nicotiana glauca, Nicotiana longiflora, Nicotiana rustica, Nicotiana tabacum*, and *Nicotiana occidentalis*. In particular embodiments, the plant is selected from the group consisting of *Citrus reticulata, Citrus sinensis, Citrus Clementina, Capsicum annuum, Solanum tuberosum, Solanum lycopersicum, Solanum melongena*, and *Nitotiana benthamiana*. In particular embodiments, the plant is a sweet orange plant (*Citrus sinensis*). In particular embodiments, the plant is a clementine plant (*Citrus clementina*). In particular embodiments, the plant is a potato plant (*Solanum tuberosum*). In some embodiment, the plant is a vegetable- or fruit-producing plant.

In some embodiments, the mutation(s) introduced to the target nucleic acid sequence change the appropriate codon in the sequence to make change(s) corresponding to positions $X_1$ to $X_{25}$ as set forth in the sequence of SEQ ID NO:27. For example, after introducing the mutations to the target nucleic acid to change the appropriate codons, the modified nucleic acid sequence encode, at its corresponding positions, one or more amino acids as set forth in positions $X_1$ to $X_{25}$ of SEQ ID NO:27. Also provided as a plant or plant cell resulting from the above-described method. Such a plant will contain a non-naturally-occurring nucleic acid sequence encoding the SAMP.

VI. Expression Cassettes

In some embodiments, the present disclosure provides expression cassettes comprising a polynucleotide encoding a SAMP (e.g., an HS peptide) of the disclosure, wherein introduction of the expression cassette into a plant results in a transgenic plant expressing the SAMP. In some embodiments, a promoter may be operably linked to the polynucleotide encoding the SAMP. The promoter may be heterologous to the polynucleotide. In some embodiments, the promoter may be inducible. In some embodiments, the promoter may plant tissue-specific (e.g., phloem-specific, tuber-specific, root-specific, stem-specific, trunk-specific, or leaf-specific).

Any of a number of means well known in the art can be used to drive SAMP expression in plants. Any organ can be targeted, such as shoot vegetative organs/structures (e.g. leaves, stems, and tubers), roots, flowers and floral organs/structures (e.g. bracts, sepals, petals, stamens, carpels, anthers and ovules), seed (including embryo, endosperm, and seed coat) and fruit. Alternatively, the polynucleotide encoding a SAMP (e.g., an HS peptide) described herein can be expressed specifically in certain cell and/or tissue types within one or more organs (e.g., guard cells in leaves using a guard cell-specific promoter). Alternatively, the polynucleotide encoding a SAMP (e.g., an HS peptide) described herein can be expressed constitutively (e.g., using the CaMV 35S promoter).

To use a polynucleotide encoding a SAMP (e.g., an HS peptide) described herein in the above techniques, recombinant DNA vectors suitable for transformation of plant cells are prepared. Techniques for transforming a wide variety of higher plant species are well known and described in the technical and scientific literature. See, e.g., Weising et al *Ann. Rev. Genet.* 22:421-477 (1988). A DNA sequence coding for the SAMP preferably will be combined with transcriptional and translational initiation regulatory sequences which will direct the transcription of the sequence from the gene in the intended tissues of the transformed plant.

For example, a plant promoter fragment may be employed to direct expression of the SAMP (e.g., an HS peptide) in all tissues of a transgenic plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumafaciens*, and other transcription initiation regions from various plant genes known to those of skill.

Alternatively, the plant promoter may direct expression of the SAMP (e.g., an HS peptide) in a specific tissue (tissue-specific promoters) or may be otherwise under more precise environmental control (inducible promoters). Examples of tissue-specific promoters under developmental control include promoters that initiate transcription only in certain tissues, such as phloem, tubers, stems, trunks, leaves, or guard cells. Examples of environmental conditions that may affect transcription by inducible promoters include, but are not limited to, anaerobic conditions, elevated temperature, and the presence of light.

In some embodiments, a polyadenylation region at the 3'-end of the coding region of the SAMP may be included. The polyadenylation region can be derived from a naturally occurring SAMP gene, from a variety of other plant genes, or from T-DNA.

The vector comprising the polynucleotide sequences (e.g., promoters or SAMP coding regions) may include a marker gene that confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosluforon or Basta.

In some embodiments, the polynucleotide encoding the SAMP (e.g., an HS peptide) is expressed recombinantly in plant cells. A variety of different expression constructs, such as expression cassettes and vectors suitable for transformation of plant cells, can be prepared. Techniques for transforming a wide variety of higher plant species are well known and described in the technical and scientific literature. See, e.g., Weising et al. *Ann. Rev. Genet.* 22:421-477 (1988). A DNA sequence coding for a SAMP (e.g., an HS peptide) described herein can be combined with cA-acting (promoter) and trans-acting (enhancer) transcriptional regulatory sequences to direct the timing, tissue type, and levels of transcription in the intended tissues of the transformed plant. Translational control elements can also be used.

Embodiments of the present disclosure also provide for a polynucleotide encoding the SAMP (e.g., an HS peptide) to be operably linked to a promoter which, in some embodiments, is capable of driving the transcription of the SAMP coding sequence in plants. The promoter can be, e.g., derived from plant or viral sources. The promoter can be, e.g., constitutively active, inducible, or tissue specific. In construction of recombinant expression cassettes, vectors, transgenics, of the disclosure, a different promoter can be chosen and employed to differentially direct gene expression, e.g., in some or all tissues of a plant or animal.

Constitutive Promoters

A fragment can be employed to direct expression of a polynucleotide encoding the SAMP (e.g., an HS peptide) in all transformed cells or tissues, e.g., as those of a transgenic plant. The term "constitutive regulatory element" means a regulatory element that confers a level of expression upon an operatively linked nucleic molecule that is relatively independent of the cell or tissue type in which the constitutive regulatory element is expressed. A constitutive regulatory element that is expressed in a plant generally is widely expressed in a large number of cell and tissue types. Promoters that drive expression continuously under physiological conditions are referred to as "constitutive" promoters and are active under most environmental conditions and states of development or cell differentiation.

A variety of constitutive regulatory elements useful for ectopic expression in a transgenic plant are well known in the art. The cauliflower mosaic virus 35S (CaMV 35S) promoter, for example, is a well-characterized constitutive regulatory element that produces a high level of expression in all plant tissues (Odell et al., *Nature* 313:810-812 (1985)). The CaMV 35S promoter can be particularly useful due to its activity in numerous diverse plant species (Benfey and Chua, *Science* 250:959-966 (1990); Futterer et al., *Physiol. Plant* 79:154 (1990); Odell et al., supra, 1985). A tandem 35S promoter, in which the intrinsic promoter element has been duplicated, confers higher expression levels in comparison to the unmodified 35S promoter (Kay et al., *Science* 236:1299 (1987)). Other useful constitutive regulatory elements include, for example, the cauliflower mosaic vims 19S promoter; the Figwort mosaic virus promoter; and the nopaline synthase (nos) gene promoter (Singer et al., *Plant Mol. Biol.* 14:433 (1990); An, *Plant Physiol.* 81:86 (1986)).

Additional constitutive regulatory elements including those for efficient expression in monocots also are known in the art, for example, the pEmu promoter and promoters based on the rice Actin-1 5' region (Last et al, *Theor. Appl. Genet.* 81:581 (1991); Mcelroy et al., *Mol. Gem Genet.* 231:150 (1991); Mcelroy et al., *Plant Cell* 2:163 (1990)). Chimeric regulatory elements, which combine elements from different genes, also can be useful for ectopically expressing a nucleic acid molecule encoding a SAMP (e.g., an HS peptide) described herein (Comai et al., *Plant Mol. Biol.* 15:373 (1990)).

Other examples of constitutive promoters include the 1'- or 2'-promoter derived from T-DNA of *Agrobacterium tumafaciens* (see, e.g., Mengiste (1997) supra; O'Grady (1995) *Plant Mol. Biol.* 29:99-108); actin promoters, such as the *Arabidopsis* actin gene promoter (see, e.g., Huang (1997) *Plant Mol. Biol.* 1997 33:125-139); alcohol dehydrogenase (Adh) gene promoters (see, e.g., Millar (1996) *Plant Mol. Biol.* 31:897-904); ACTII from *Arabidopsis* (Huang et al. *Plant Mol. Biol.* 33:125-139 (1996)), Cat3 from *Arabidopsis* (GenBank No. U43147, Zhong et al, *Mol. Gen. Genet.* 251:196-203 (1996)), the gene encoding stearoyl-acyl carrier protein desaturase from *Brassica napus* (Genbank No. X74782, Solocombe et al. *Plant Physiol.* 104:1167-1176 (1994)), GPc1 from maize (GenBank No. X15596, Martinez et al *J. Mol. Biol* 208:551-565 (1989)), Gpc2 from maize (GenBank No. U45855, Manjunath et al, *Plant Mol. Biol.* 33:97-112 (1997)), other transcription initiation regions from various plant genes known to those of skill. See also Holtorf *Plant Mol Biol.* 29:637-646 (1995).

Inducible Promoters

Alternatively, a plant promoter may direct expression of the polynucleotide encoding the SAMP (e.g., an HS peptide) under the influence of changing environmental conditions or developmental conditions. Examples of environmental conditions that may affect transcription by inducible promoters include anaerobic conditions, elevated temperature, drought, or the presence of light. Such promoters are referred to herein as "inducible" promoters. In some embodiments, an inducible promoter is one that is induced by one or more environmental stressors, including but not limited to, drought, freezing cold, and high salt. For example, the disclosure can incorporate a drought-specific promoter such as a drought-inducible promoter of maize (e.g., the maize rab17 drought-inducible promoter (Vilardell et al. (1991) *Plant Mol. Biol* 17:985-993; Vilardell et al. (1994) *Plant Mol. Biol* 24:561-569)); or alternatively a cold, drought, and high salt inducible promoter from potato (Kirch (1997) *Plant Mol. Biol.* 33:897-909) or from *Arabidopsis* (e.g., the rd29A promoter (Kasuga et al. (1999) *Nature Biotechnology* 17:287-291). Other environmental stress-inducible promoters include promoters from the following genes: Rab21, Wsi18, Lea3, Ugel, Dip1, and R1G1B in rice (Yi et al (2010) *Planta* 232:743-754).

In some embodiments, a plant promoter is a stress-inducible promoter (e.g., a drought-, cold-, or salt-inducible promoter) that comprises a dehydration-responsive element (DRE) and/or an ABA-responsive element (ABRE), including but not limited to the rd29A promoter.

Alternatively, plant promoters which are inducible upon exposure to plant hormones, such as auxins, are used to express the polynucleotide encoding the SAMP (e.g., an HS peptide). For example, the disclosure can use the auxin-response elements E1 promoter fragment (AuxREs) in the soybean (*Glycine max* L.) (Liu (1997) *Plant Physiol.* 115: 397-407); the auxin-responsive *Arabidopsis* GST6 promoter (also responsive to salicylic acid and hydrogen peroxide) (Chen (1996) *Plant J.* 10: 955-966); the auxin-inducible parC promoter from tobacco (Sakai (1996) 37:906-913); a plant biotin response element (Streit (1997) *Mol. Plant Microbe Interact.* 10:933-937); and, the promoter responsive to the stress hormone abscisic acid (Sheen (1996) Science 274:1900-1902).

Plant promoters inducible upon exposure to chemicals reagents that may be applied to the plant, such as herbicides or antibiotics, are also useful for expressing the polynucleotide encoding the SAMP (e.g., an HS peptide). For example, the maize In2-2 promoter, activated by benzenesulfonamide herbicide safeners, can be used (De Veylder (1997) *Plant Cell Physiol.* 38:568-577); application of different herbicide safeners induces distinct gene expression patterns, including expression in the root, hydathodes, and the shoot apical meristem. A SAMP (e.g., an HS peptide) coding sequence can also be under the control of, e.g., a tetracycline-inducible promoter, e.g., as described with transgenic tobacco plants containing the *Avena sativa* L. (oat) arginine decarboxylase gene (Masgrau (1997) *Plant J.* 11:465-473); or, a salicylic acid-responsive element (Stange (1997) *Plant J.* 11:1315-1324; Uknes et al., *Plant Cell* 5:159-169 (1993); Bi et al., *Plant J.* 8:235-245 (1995)).

Examples of useful inducible regulatory elements include copper-inducible regulatory elements (Mett et al., *Proc. Natl. Acad. Sci. USA* 90:4567-4571 (1993); Furst et al., *Cell* 55:705-717 (1988)); tetracycline and chlor-tetracycline-inducible regulatory elements (Gatz et al, Plant J. 2:397-404 (1992); Röder et al., *Mol. Gem Genet.* 243:32-38 (1994); Gatz, *Meth. Cell Biol.* 50:411-424 (1995)); ecdysone inducible regulatory elements (Christopherson et al., *Proc. Natl. Acad Sci. USA* 89:6314-6318 (1992); Kreutzweiser et al., Ecotoxicol. Environ. Safety 28:14-24 (1994)); heat shock inducible regulatory elements (Takahashi et al., *Plant Physiol.* 99:383-390 (1992); Yabe et al., *Plant Cell Physiol.* 35:1207-1219 (1994); Ueda et al., *Mol. Gem Genet.* 250:533-539 (1996)); and lac operon elements, which are used in combination with a constitutively expressed lac repressor to confer, for example, IPTG-inducible expression (Wilde et al, *EMBO J.* 11:1251-1259 (1992)). An inducible regulatory element useful in the transgenic plants of the disclosure also can be, for example, a nitrate-inducible promoter derived from the spinach nitrite reductase gene (Back et al., *Plant Mol. Biol.* 17:9 (1991)) or a light-inducible promoter, such as that associated with the small subunit of RuBP carboxylase or the LHCP gene families (Feinbaum et al., *Mol. Gem Genet.* 226:449 (1991); Lam and Chua, *Science* 248:471 (1990)).

Tissue-Specific Promoters

Alternatively, the plant promoter may direct expression of the polynucleotide encoding the SAMP (e.g., an HS peptide) in a specific tissue (tissue-specific promoters). Tissue specific promoters are transcriptional control elements that are only active in particular cells or tissues at specific times during plant development, such as in vegetative tissues or reproductive tissues.

Examples of tissue-specific promoters under developmental control include promoters that initiate transcription only (or primarily only) in certain tissues, such as vegetative tissues, e.g., roots or leaves, or reproductive tissues, such as fruit, ovules, seeds, pollen, pistils, flowers, or any embryonic tissue, or epidermis or mesophyll. Reproductive tissue-specific promoters may be, e.g., ovule-specific, embryo-specific, endosperm-specific, integument-specific, seed and seed coat-specific, pollen-specific, petal-specific, sepal-specific, or some combination thereof. In some embodiments, the promoter is cell-type specific, e.g., guard cell-specific.

Epidermal-specific promoters include, for example, the *Arabidopsis* LTP1 promoter (Thoma et al. (1994) *Plant Physiol.* 105(1):35-45), the CER1 promoter (Aarts et al. (1995) *Plant Cell* 7:2115-27), and the CER6 promoter (Hooker et al. (2002) *Plant Physiol* 129:1568-80), and the orthologous tomato LeCER6 (Vogg el al. (2004) *J. Exp Bot.* 55:1401-10).

Guard cell-specific promoters include, for example, the DGP1 promoter (Li et al. (2005) *Science China C Life Sci.* 48:181-186).

Other tissue-specific promoters include seed promoters. Suitable seed-specific promoters are derived from the following genes: MAC1 from maize (Sheridan (1996) *Genetics* 142:1009-1020); Cat3 from maize (GenBank No. L05934, Abler (1993) *Plant Mol Biol.* 22:10131-1038); vivparous-1 from *Arabidopsis* (Genbank No. U93215); atmyc1 from *Arabidopsis* (Urao (1996) *Plant Mol. Biol* 32:571-57; Conceicao (1994) *Plant* 5:493-505); napA from *Brassica napus* (GenBank No. J02798, Josefsson (1987) JBL 26:12196-1301); and the napin gene family from *Brassica napus* (Sjodahl (1995) *Planta* 197:264-271).

A variety of promoters specifically active in vegetative tissues, such as leaves, stems, roots and tubers, can also be used to express polynucleotide encoding SAMPs (e.g., HS peptides) described herein. For example, promoters controlling patatin, the major storage protein of the potato tuber, can be used, see, e.g., Kim (1994) *Plant Mol. Biol.* 26:603-615; Martin (1997) *Plant J.* 11:53-62. The ORF13 promoter from *Agrobacterium rhizogenes* that exhibits high activity in roots can also be used (Hansen (1997) *Mol. Gen. Genet.* 254:337-343. Other useful vegetative tissue-specific promoters include: the tarin promoter of the gene encoding a globulin from a major taro (*Colocasia esculenta* L. Schott) corm protein family, tarin (Bezerra (1995) *Plant Mol. Biol.* 28:137-144); the curculin promoter active during taro corm development (de Castro (1992) *Plant Cell* 4:1549-1559) and the promoter for the tobacco root-specific gene TobRB7, whose expression is localized to root meristem and immature central cylinder regions (Yamamoto (1991) *Plant Cell* 3:371-382).

Leaf-specific promoters, such as the ribulose biphosphate carboxylase (RBCS) promoters, can also be used. For example, the tomato RBCS1, RBCS2 and RBCS3A genes are expressed in leaves and light-grown seedlings, only RBCS1 and RBCS2 are expressed in developing tomato fruits (Meier (1997) *FEBS Lett.* 415:91-95). Ribulose bisphosphate carboxylase promoters expressed almost exclusively in mesophyll cells in leaf blades and leaf sheaths at high levels, described by Matsuoka (1994) Plant J. 6:311-319, can be used. Another leaf-specific promoter is the light harvesting chlorophyll a/b binding protein gene promoter, see, e.g., Shiina (1997) *Plant Physiol.* 115:477-483; Casal (1998) *Plant Physiol.* 116:1533-1538. The *Arabidopsis thaliana* myb-related gene promoter (Atmyb5) described by Li (1996) *FEBS Lett.* 379:117-121, is leaf-specific. The Atmyb5 promoter is expressed in developing leaf trichomes, stipules, and epidermal cells on the margins of young rosette and cauline leaves, and in immature seeds. Atmyb5 mRNA appears between fertilization and the 16-cell stage of embryo development and persists beyond the heart stage. A leaf promoter identified in maize by Busk (1997) *Plant J.* 11:1285-1295, can also be used.

Another class of useful vegetative tissue-specific promoters are meristematic (root tip and shoot apex) promoters. For example, the "SHOOTMERISTEMLESS" and "SCARECROW" promoters, which are active in the developing shoot or root apical meristems, described by Di Laurenzio (1996) *Cell* 86:423-433; and, Long (1996) *Nature* 379:66-69; can be used. Another useful promoter is that which controls the expression of 3-hydroxy-3-methylglutaryl coenzyme A reductase HMG2 gene, whose expression is restricted to meristematic and floral (secretory zone of the stigma, mature pollen grains, gynoecium vascular tissue, and fertilized ovules) tissues (see, e.g., Enjuto (1995) *Plant Cell.* 7:517-527). Also useful are kn1-related genes from maize and other species which show meristem-specific expression, see, e.g., Granger (1996) *Plant Mol. Biol.* 31:373-378; Kerstetter (1994) *Plant Cell* 6:1877-1887; Hake (1995) *Philos. Trans. R. Soc. Lond. B. Biol. Sci.*

350:45-51. For example, the *Arabidopsis thaliana* KNAT1 promoter (see, e.g., Lincoln (1994) *Plant Cell* 6:1859-1876).

One of skill will recognize that a tissue-specific promoter may drive expression of operably linked sequences in tissues other than the target tissue. Thus, as used herein a tissue-specific promoter is one that drives expression preferentially in the target tissue, but may also lead to some expression in other tissues as well.

In another embodiment, the polynucleotide encoding the SAMP (e.g., an HS peptide) is expressed through a transposable element. This allows for constitutive, yet periodic and infrequent expression of the constitutively active polypeptide. The disclosure also provides for use of tissue-specific promoters derived from viruses including, e.g., the tobamovirus subgenomic promoter (Kumagai (1995) *Proc. Natl. Acad. Sci. USA* 92:1679-1683; the rice tungro bacilliform virus (RTBV), which replicates only in phloem cells in infected rice plants, with its promoter which drives strong phloem-specific reporter gene expression; the cassava vein mosaic vims (CVMV) promoter, with highest activity in vascular elements, in leaf mesophyll cells, and in root tips (Verdaguer (1996) *Plant Mol. Biol.* 31:1129-1139).

In another embodiment, the present disclosure provides for expression vectors comprising an expression cassette of the disclosure (e.g., as described herein).

VII. Plants

In some embodiments, the plant is a *citrus* plant. In some embodiments, the *citrus* plant is an orange tree, a lemon tree, a lime tree, or a grapefruit tree. In one embodiment, the *citrus* plant is a navel orange, Valencia orange, sweet orange, mandarin orange, or sour orange. In one embodiment, the *citrus* plant is a lemon tree. In one embodiment, the *citrus* plant is a lime tree. In some embodiments, the plant is a relative of a *citrus* plant, such as orange jasmine, limeberry, and trifoliate orange. In some embodiments, the plant is a potato plant.

In some embodiments, the present disclosure provides for plants (or a plant cell, seed, flower, leaf, fruit, or other plant part from such plants or processed food or food ingredient from such plants) comprising an expression cassette comprising a promoter operably linked to a polynucleotide encoding a SAMP (e.g., an HS peptide) of the disclosure (e.g., as described herein). In some embodiments, the plant has decreased UBC expression or activity and/or increased expression or activity of Pi transporters.

EXAMPLES

Example 1—Expression of Antimicrobial SAMP Genes

The expression levels of SAMPs in HLB-susceptible and HLB-tolerant plants were detected by quantitative RT-PCR. The expression level of *citrus* actin was used as an internal control. The expression level of SAMPs is higher in two different HLB-tolerant/resistant varieties from totally different geographic and genetic backgrounds (a hybrid of Cleopatra mandarin (*Citrus reticulata*) and *Poncirus trifoliate* US942, and a *Eremocitrus glauca* hybrid) than in their corresponding HLB-sensitive close relatives (FIGS. 1A and 1B).

Figure 3A:
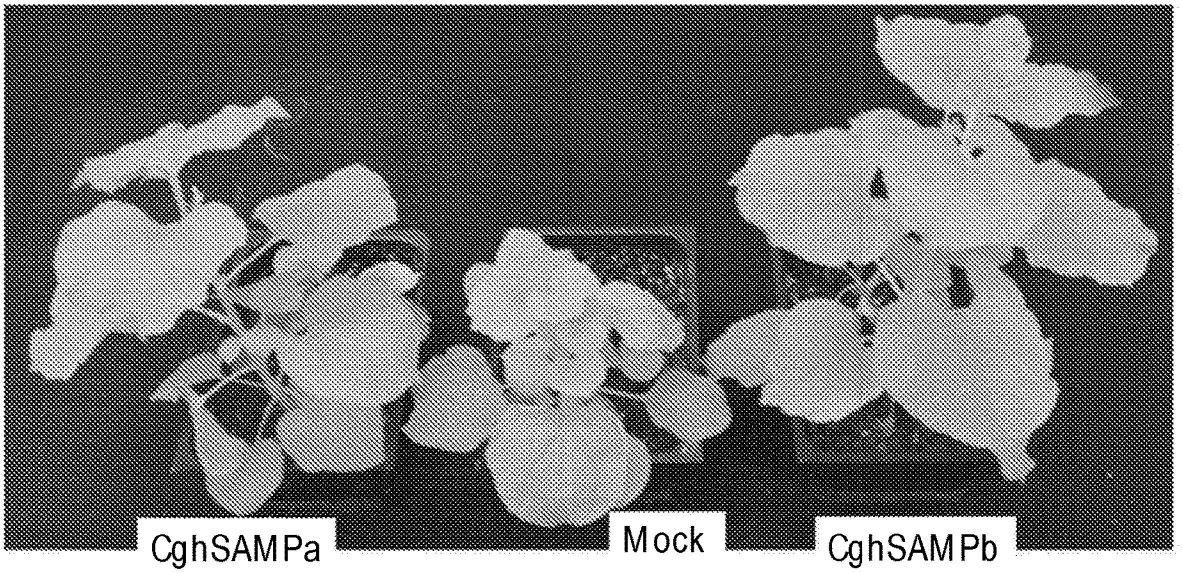
FIG. 3A shows photographs of *Ca. L. solanacearum*-infected *Nb* plants treated with CghSAMPa (SAMPa) or CghSAMPb (SAMPb) peptide, or mock solution.
Figure 3B:
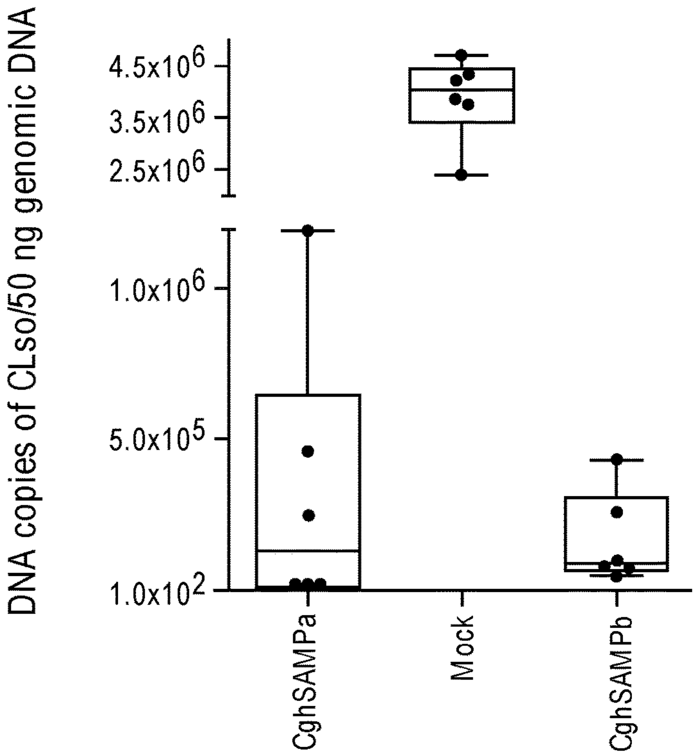
FIG. 3B shows the bacterial titers of *Ca. L. solanacearum*-infected *Nb* plants treated with CghSAMPa (SAMPa) or CghSAMPb (SAMPb) peptide, or mock solution.
Figure 7:
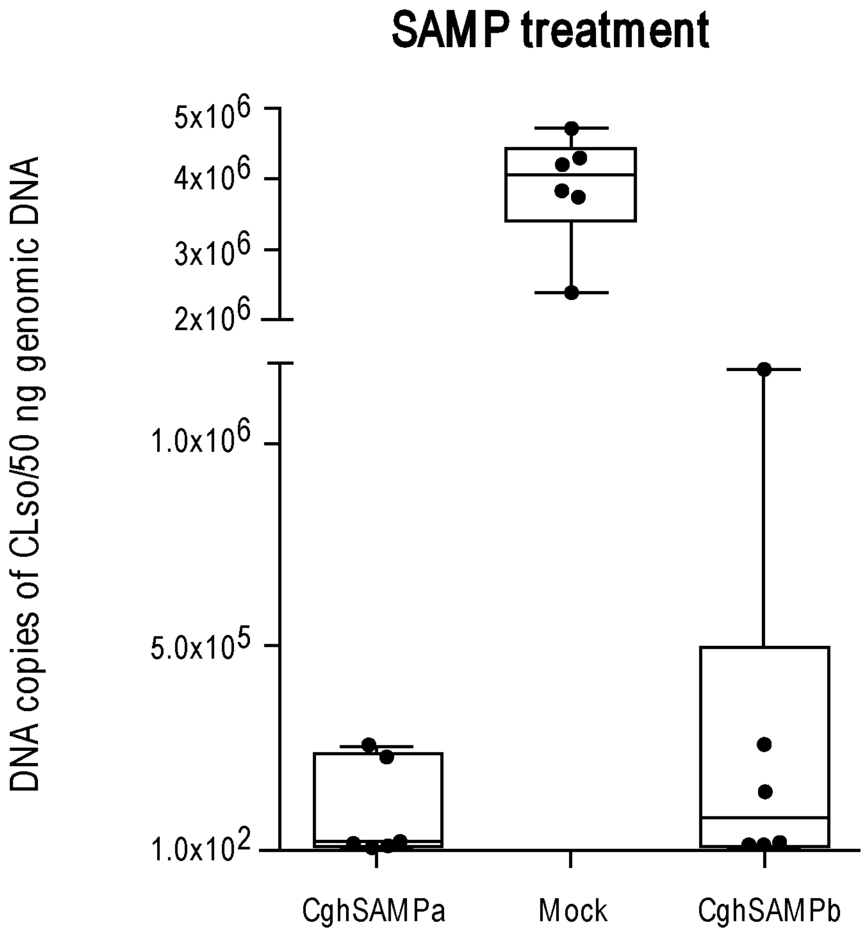
FIG. 7 shows the bacterial titers of *Ca. L. solanacearum*-infected tomato plants treated with CghSAMPa or CghSAMPb peptide, or mock solution.

Example 2—Effects of SAMPs in Suppressing *Candidatus Liberibacter Solanacearum* (*Ca. L. Solanacearum*) Infection Solanaceae plant *Nicotiana benthamiana* (*Nb*) is commonly used for gene function studies against pathogen infections. *Nb* can be infected by *Ca. L. solanacearum* by being infested with *Ca. L. solanacearum*-positive potato psyllid, which is a pathosystem highly similar to potato ZC disease and *citrus* HLB. The effects of two SAMPs, CghSAMPa and CghSAMPb (SEQ ID NOs:1 and 2, respectively, which are hybrids from crossing *Citrus glauca* with *Citrus* sp.), were tested using the *Nb*/potato psyllid/*Ca. L. solanacearum* pathosystem. The CghSAMPa and CghSAMPb peptides were expressed and purified in *E. coli. Ca. L. solanacearum*-infected *Nb* plants were treated with 30 μM CghSAMPa or CghSAMPb peptide, or mock solution by stem injection. The photos in FIG. 3A were taken after 3 weeks of treatment. FIG. 3A shows that the infected plants treated with the SAMPs were able to grow much better than the plants that received mock treatment. FIGS. 3B and 7 further show that the plants treated with CghSAMPa and CghSAMPb peptides had much lower bacterial titer compared to the plants treated with mock solution. The results demonstrated that the two SAMPs from resistant/tolerant *citrus* rootstocks significantly controlled the titer of *Ca. L. solanacearum* in *Nb* plants and promoted plant growth.

Example 3—Effects of SAMPs Delivered Via Trunk Delivery

Figure 4A:
FIG. 4A-B shows SAMP effectively suppresses the growth of C. Las (*Candidatus Liberibacter asiaticus*) in HLB-positive *citrus* plants and the new shoots have no HLB symptoms.
Figure 4B:
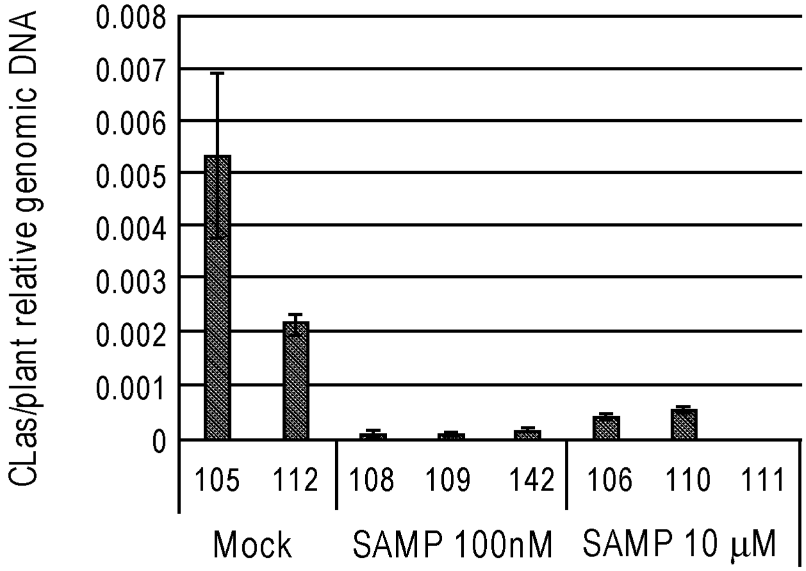

We have tested effective SAMP treatment on HLB-positive *citrus* plants using trunk delivery method, and the bacterial titer of all the treated trees are largely reduced, about 30-100 folds. No bacteria were detected in the treated trees. All the new shoots and leaves from the treated trees were no longer symptomatic, and the new shoots and leaves from the mock treated plants still have yellow patch symptoms (FIG. 4)

Figure 5C:
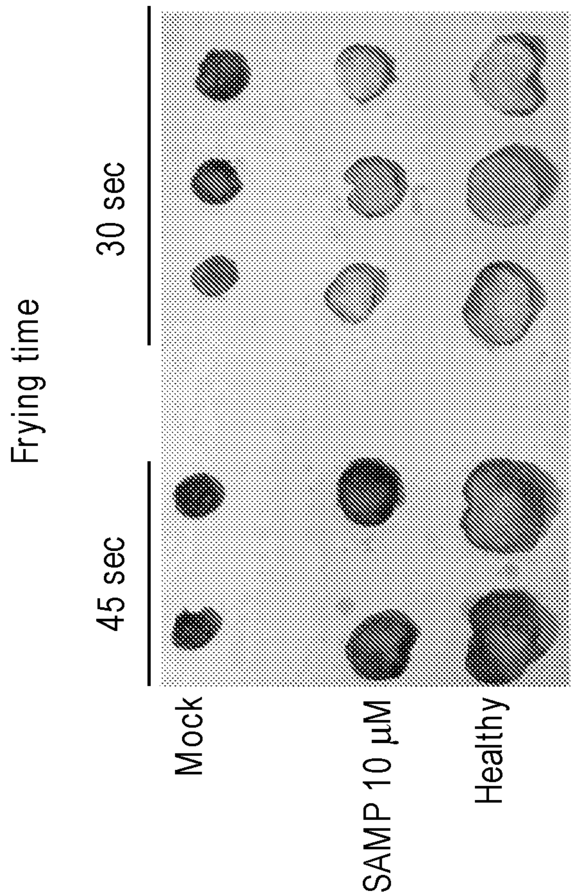
FIG. 5A-C shows SAMP pre-treated potato plants grew better and produced more tubers after *C. Lso* (*Ca. L. solanacearum*) infection by potato psyllid feeding.
Figure 5A:
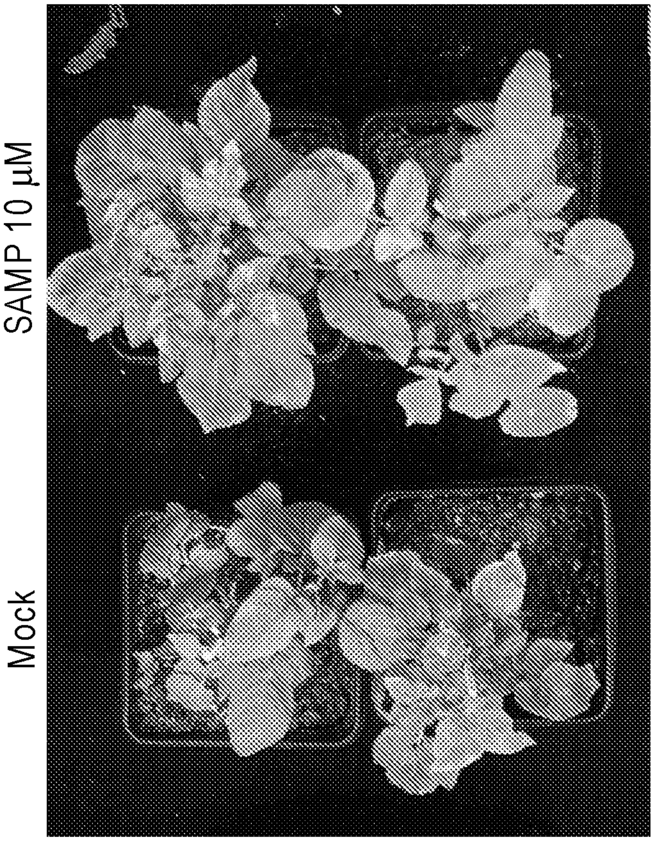
Figure 5B:

Example 4—Effects of SAMPs in Suppressing *Candidatus Liberibacter Solanacearum* (*Ca. L. Solanacearum*) Infection in Potato and Tomato We have also performed the effective SAMP treatment on C. Lso-infected potato. The disease symptom was clearly inhibited, and the yield of tuber production was increased. (FIG. 5)

Figure 6A:
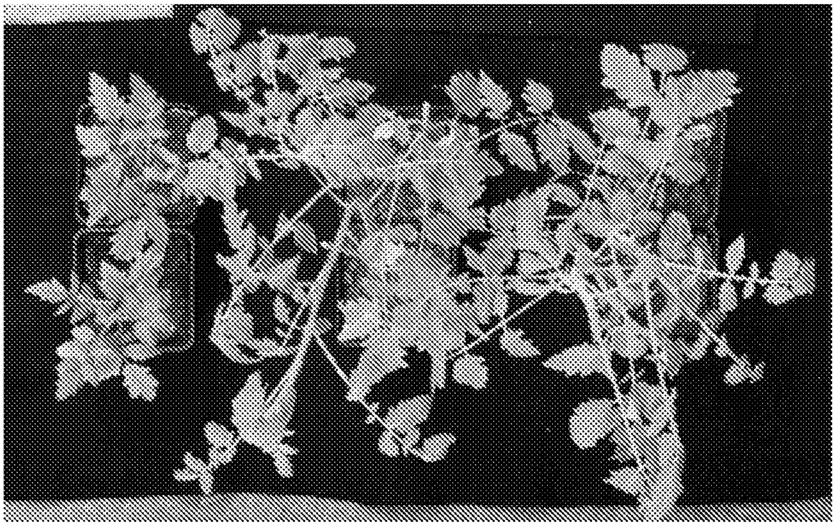
FIG. 6A-B show SAMP pre-treated tomato plants grew better after *C. Lso* infection by potato psyllid feeding.
Figure 6B:
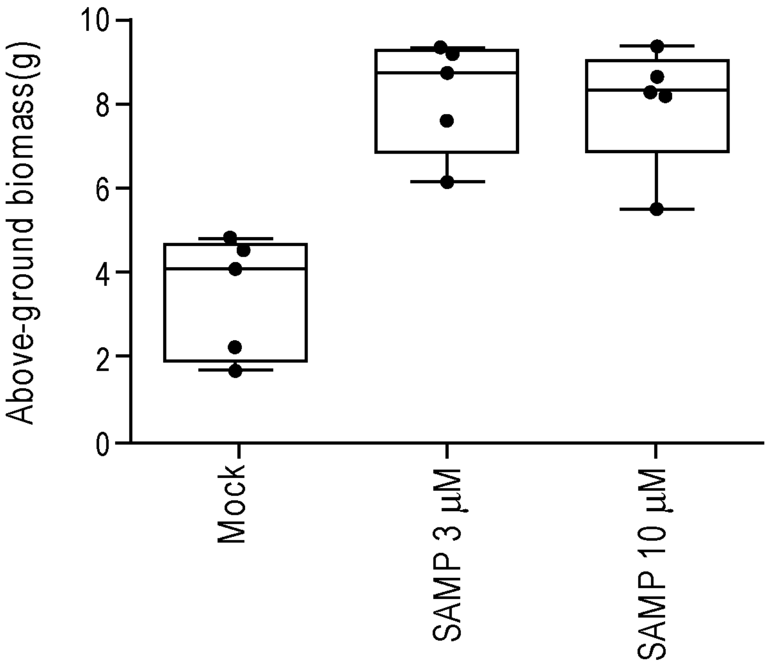

We also tested the effective SAMP on C. Lso-infected tomato, and the disease symptom was largely reduced as well. (FIG. 6)

Example 5—Effects of SAMPs in *Citrus* Plants

Figure 8A:
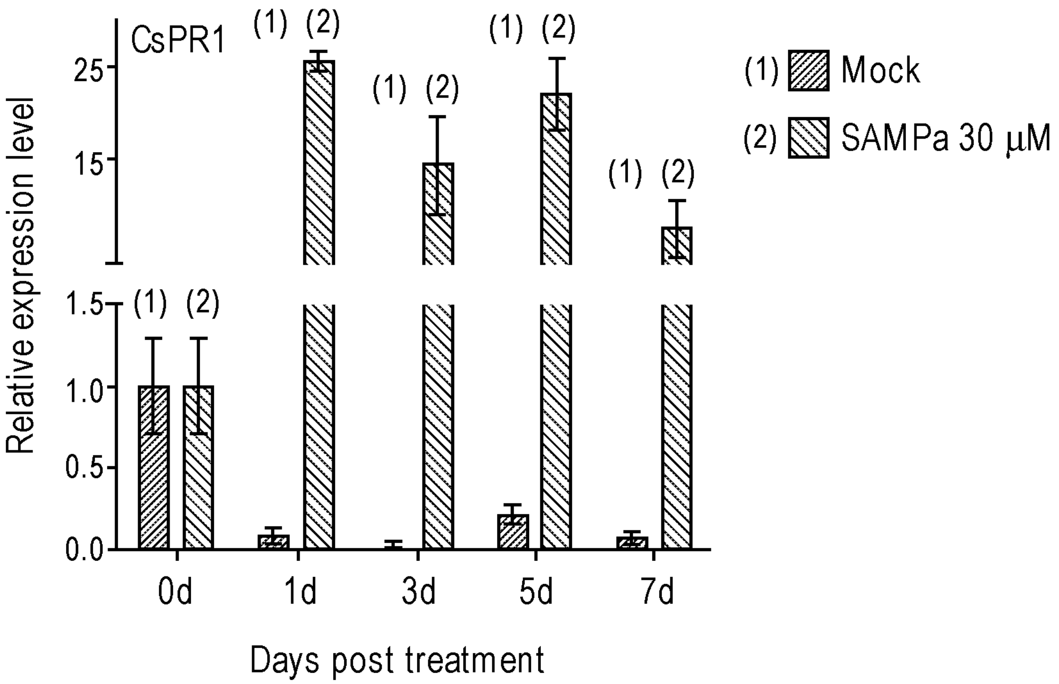
FIGS. 8A-8C show that SAMPs have priming effect on *citrus* plants and can be used to vaccinate the seedlings in the nursery.
Figure 8B:
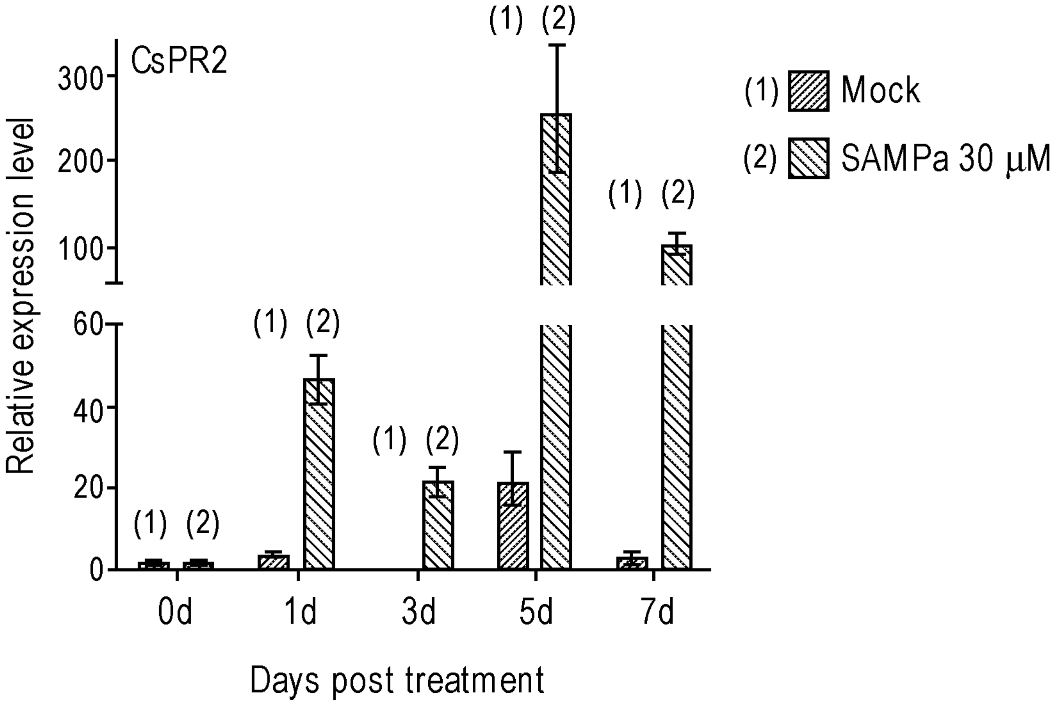
Figure 8C:
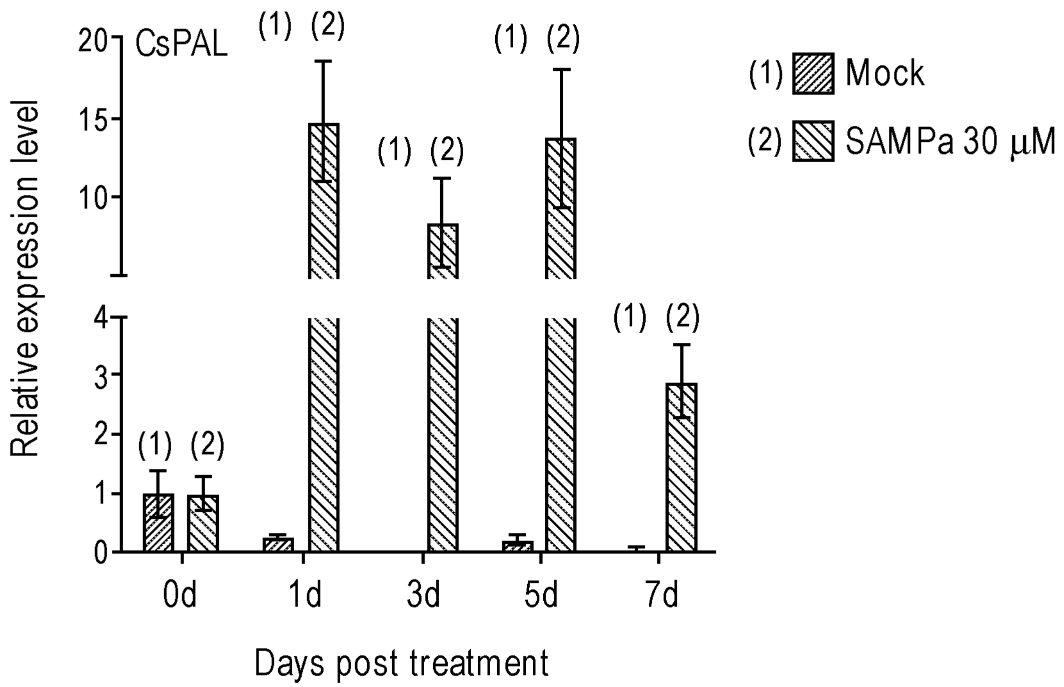

SAMP was apply by foliar sprayed with 5% Southern Ag Methylated Seed Oil (MSO) on the 1 year old seedlings. The expression level of defense response marker genes CsPR1, CsPR2, and CAPAL were evaluated by qRT-PCR with the ubiquitin gene as an internal control for up to 7 days after treatment. FIGS. 8A-8C show that SAMPs primed the *citrus* plants to have increased expression of the defense response marker genes.

Figure 9A:
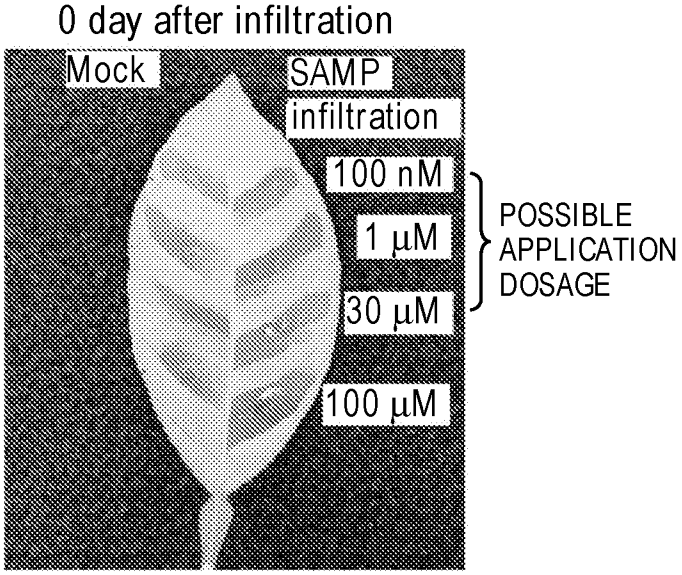
FIGS. 9A and 9B show that SAMPs have low phytotoxic activity on *citrus* leaves.
Figure 9B:
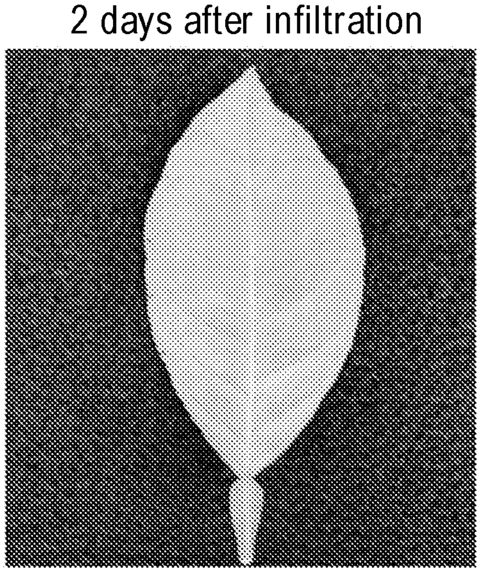

Further, different concentrations of SAMP solutions were infiltrated into sweet orange leaves. No cell death was observed with 30 μM treatment. FIGS. 9A and 9B show that SAMPs have low phytotoxic activity on *citrus* leaves.

Figure 10:
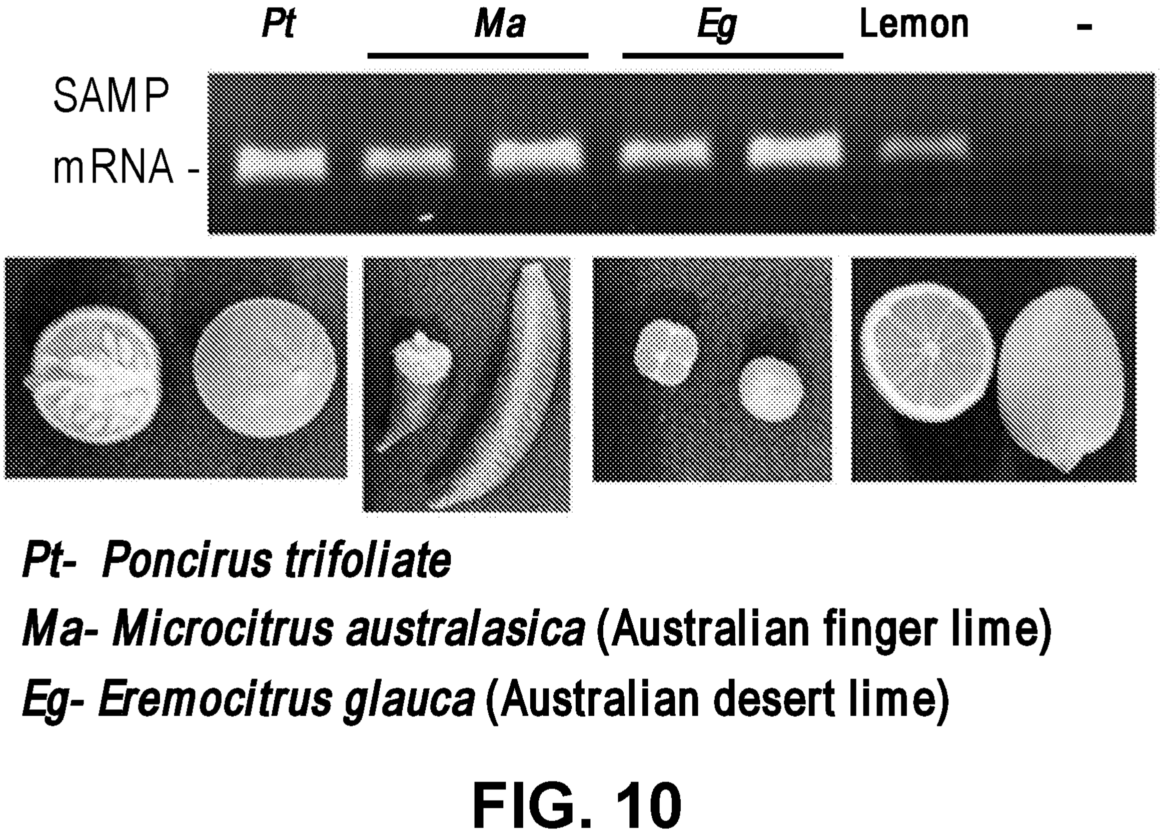
FIG. 10 shows that SAMPs are highly expressed in the fruit of Australian finger lime, Australian desert lime, lemon, and *Poncirus trifoliate* (common root stock).

Moreover, mRNA expression analysis (FIG. 10) demonstrates that SAMPs are highly expressed in the fruit of Australian finger lime, Australian desert lime, lemon, and *Poncirus trifoliate* (common root stock), which have already been consumed by humans for hundreds of years. The mRNA expression was detected by RT-PCR.

Example 6—Protease Digestion of SAMPs

Figure 11:
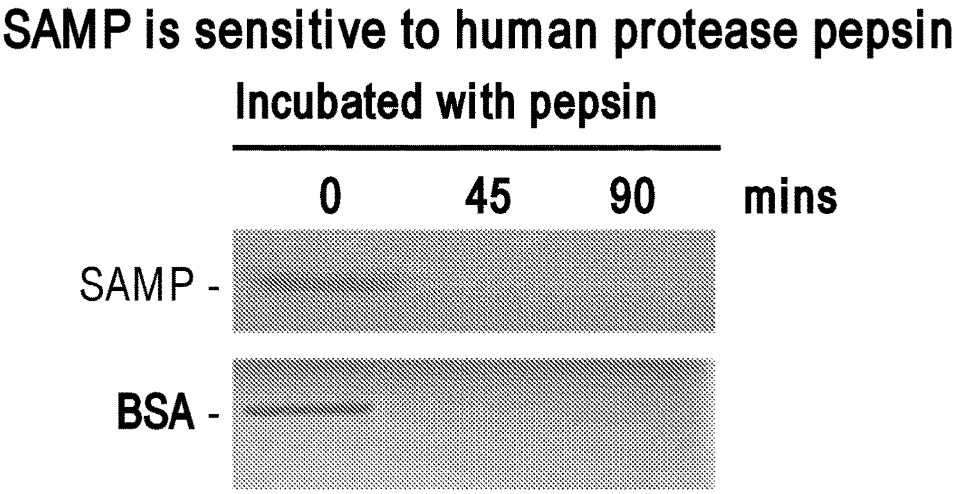
FIG. 11 shows that SAMPs are sensitive to human protease pepsin, a major gastric enzyme.

FIG. 11 shows that SAMPs are sensitive to human protease pepsin, a major gastric enzyme. 20 μg of SAMP were incubated with 0.4% solution of pepsin in 10 mM HCl at 37° C. The reaction was analyzed with 18% SDS-PAGE gel and visualized with coomassie blue staining. SAMP was completely digested within 45 min.

Example 7—Stability of SAMPs

Figure 12:
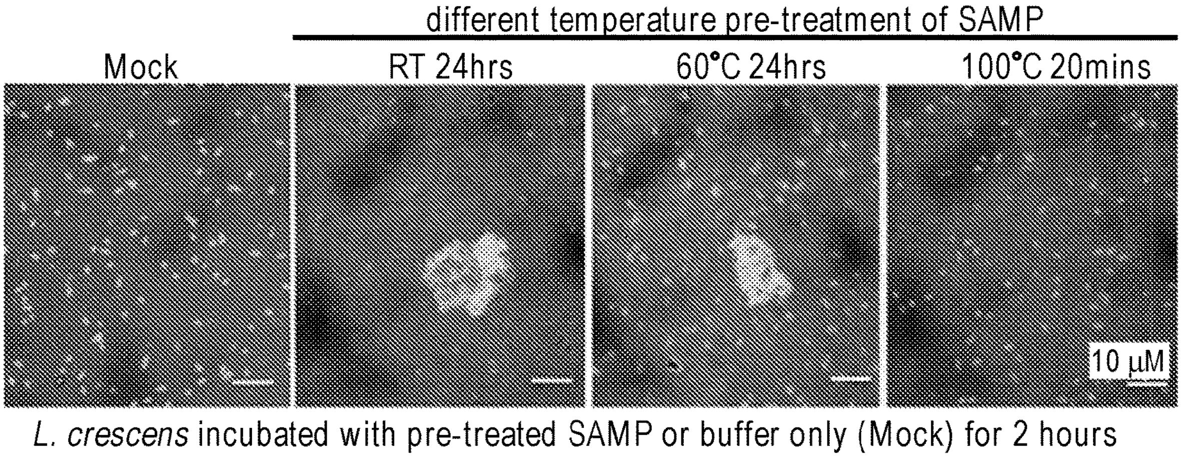
FIG. 12 shows that SAMPs are stable after storing at room temperature for 24 hours, or 60° C. for 24 hours, or 100° C. for 20 mins, and remain active to kill *Liberibacter crescens* as shown by the viability/cytotoxicity assay for visualizing live and dead bacterial cells (DMAO (green): a membrane-permeable DNA dye for visualizing live bacteria, and EthD-III (red): a membrane-impermeable DNA dye for visualizing dead bacteria).

SAMPs were incubated at room temperature (RT) for 24 hours, 60° C. for 24 hours, or 100° C. for 20 mins. Subsequently, the SAMPs were used for viability/cytotoxicity assay. The assay was done by incubating $10^7$ cells/mL of *Liberbacter crescens* with the pre-treated SAMP or buffer only as mock treatment for 2 hours. The samples were then stained with DMAO (green) and EthD-III (orange), which represent live and dead cells, respectively. FIG. 12 shows that SAMPs are stable at up to 100° C.

Figure 13:
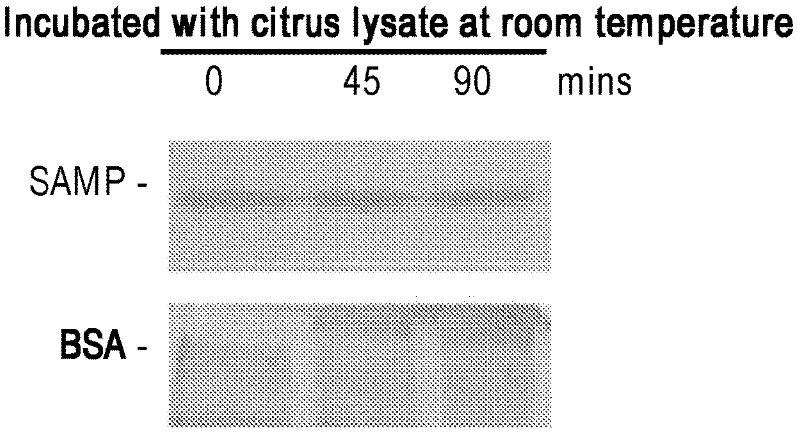
FIG. 13 shows that SAMPs are stable in *citrus* cell lysate, which indicates that they are also stable in trees.

Further, to investigate the stability of SAMPs in *citrus* plants, 20 μg of SAMPs were incubated with 200 μg fresh *citrus* lysate in 1×PBS buffer at room temperature. The reaction was analyzed with 18% SDS-PAGE gel and visualized with coomassie blue staining. FIG. 13 shows that SAMPs are stable in *citrus* cell lysate, which indicates that they are also stable in trees.

Example 8—Additional Antimicrobial Activity of SAMPs

Figure 14A:
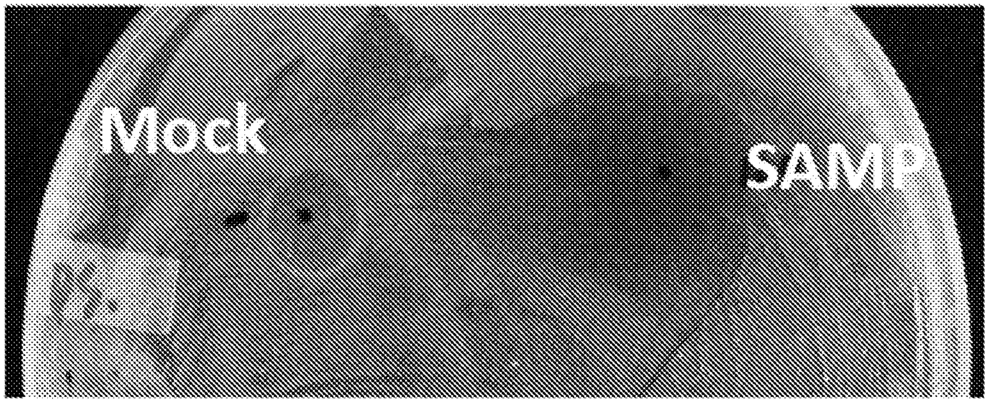
FIGS. 14A and 14B show that SAMPs exhibit antimicrobial activity against Gram-negative bacterial pathogens *Pseudomonas syringae* and *Agrobacterium tumefaciens* in the agar diffusion assay.
Figure 14B:
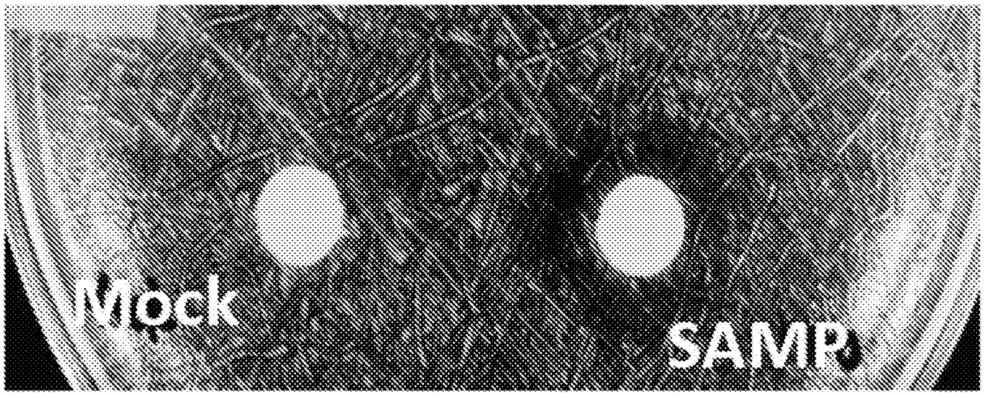

The antimicrobial activity of SAMPs against other Gram-negative bacterial pathogens was tested. Specifically, activity against *Pseudomonas syringae* and *Agrobacterium tumefaciens* was verified by agar diffusion assay, FIG. 14A and FIG. 14B respectively. Each essay was done by applying 10 μL SAMPs on the medium with bacteria, where the concentration for SAMPs was 100 μM for *Pseudomonas syringae* and 150 μM for *Agrobacterium tumefaciens* respectively. The culture plates were incubated at 28° C. and observed after 24 hours. The rings without bacterial growth confirm antimicrobial activity.

Figure 15:
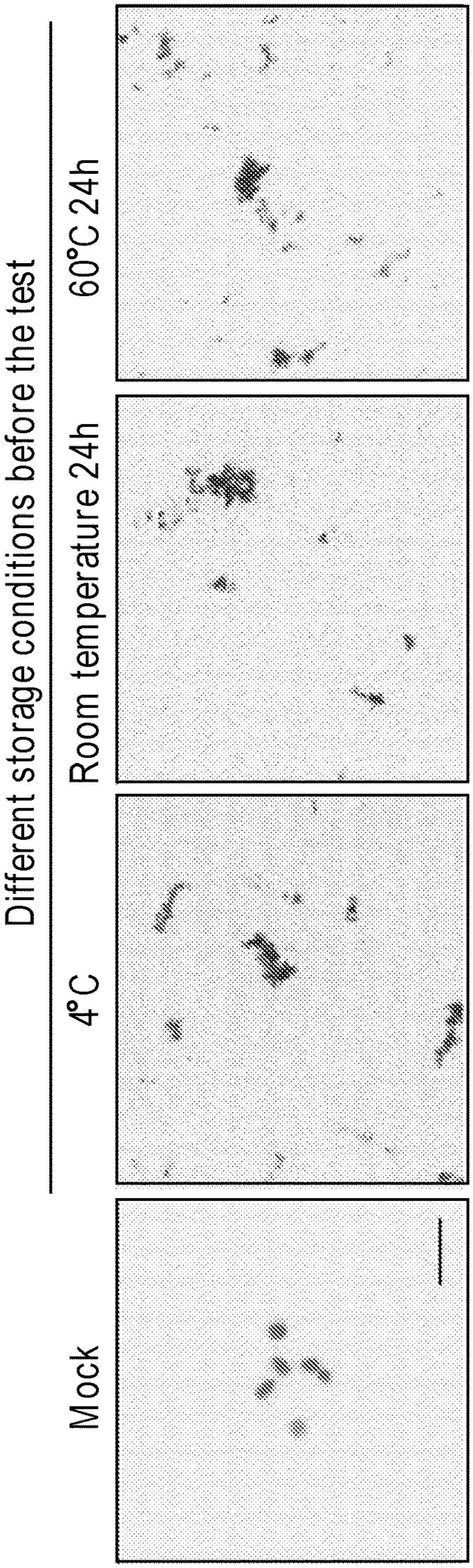
FIG. 15 shows that SAMPs, after storage for 24 hours at 4° C., room temperature, or 60° C., remain active to kill *Agrobacterium tumefaciens* as shown by the viability/cytotoxicity assay for visualizing live and dead bacterial cells (DMAO (green): a membrane-permeable DNA dye for visualizing live bacteria and EthD-III (red): a membrane-impermeable DNA dye for visualizing dead bacteria).

In addition, SAMPs were incubated at 4° C. for 24 hours, RT for 24 hours, or 60° C. for 24 hours. Subsequently, the SAMPs were used for viability/cytotoxicity assay. The assay was done by incubating $10^7$ cells/mL of *Agrobacterium tumefaciens* with the pre-treated SAMP or buffer only as mock treatment for 2 hours. The samples were then stained with DMAO (green) and EthD-III (orange), which represent live and dead cells, respectively. FIG. 15 shows that SAMPs are stable and have antimicrobial activity against *Agrobacterium tumefaciens* up to 60° C.

One or more features from any embodiments described herein or in the figures may be combined with one or more features of any other embodiment described herein in the figures without departing from the scope of the disclosure.

All publications, patents and patent applications cited in this specification are herein incorporated by reference as if each individual publication or patent application were specifically and individually indicated to be incorporated by reference. Although the foregoing disclosure has been described in some detail by way of illustration and example for purposes of clarity of understanding, it will be readily apparent to those of ordinary skill in the art in light of the teachings of this disclosure that certain changes and modifications may be made thereto without departing from the spirit or scope of the appended claims.

What is claimed:

1. An agricultural composition comprising an isolated stable antimicrobial peptide (SAMP) comprising a sequence of any one of SEQ ID NOs:1, 2, 36, and 37.

2. The agricultural composition of claim 1, wherein the isolated SAMP is a heat-stable (HS) peptide.

3. The agricultural composition of claim 1, wherein the isolated SAMP is stable in plant extracts and/or in plant lysates.

4. The agricultural composition of claim 1, further comprising at least one of an herbicide, an herbicide safener, a surfactant, a fungicide, a pesticide, a nematicide, a plant activator, a synergist, a plant growth regulator, an insect repellant, an acaricide, a molluscicide, or a fertilizer.

5. A method of preventing or treating a disease in a plant, comprising contacting the plant with the agricultural composition of claim 1.

6. A method of preventing or treating a bacterial infection in a plant caused by gram-negative bacteria, comprising contacting the plant with the agricultural composition of claim 1.

7. The method of claim 5, wherein the disease is a *Liberibacter* disease.

8. The method of claim 5, wherein the disease is an *Agrobacterium* or a *Pseudomonas syringae* disease.

9. The method of claim 5, wherein the isolated SAMP or agricultural composition is injected into the trunk of the plant.

10. The method of claim 5, wherein the isolated SAMP or agricultural composition is injected into the stem of the plant.

11. The method of claim 5, wherein the isolated SAMP or agricultural composition is foliar sprayed onto the plant or is applied to the plant by dripping irrigation to the roots or is applied to the plant by laser ablation.

12. The method of claim 7, wherein the *Liberibacter* disease is HLB.

13. The method of claim 6, wherein the bacterial infection causes potato zebra chip disease.

14. The method of claim 6, wherein the gram-negative bacteria is in the genus *Liberibacter, Agrobacterium*, or *Pseudomonas*.

15. The method of claim 14, wherein the genus *Liberibacter* is *Candidatus Liberibacter.*

16. The method of claim 14, wherein the bacteria in the genus *Liberibacter* are *Liberibacter crescens.*

17. An expression cassette comprising a promoter operably linked to a polynucleotide encoding an isolated SAMP comprising a sequence of any one of SEQ ID NOs:1, 2, 36, and 37, wherein introduction of the expression cassette into a plant results in the plant having enhanced disease resistance or disease tolerance, and wherein the promoter is heterologous to the polynucleotide.

18. The expression cassette of claim 17, wherein the promoter is selected from the group consisting of an inducible promoter, a tissue-specific promoter, and a phloem-specific promoter.

19. The expression cassette of claim 17, wherein the disease is caused by *Liberibacter.*

20. The expression cassette of claim 17, wherein the disease is caused by an *Agrobacterium* or a *Pseudomonas syringae.*

21. The expression cassette of claim 18, wherein the tissue-specific promoter is a phloem-specific promoter.

22. The expression cassette of claim 18, wherein the promoter is from a *citrus* or potato plant.

23. The expression cassette of claim 19, wherein the disease is HLB.

24. The expression cassette of claim 21, wherein phloem-specific promoter is the sucrose transporter protein SUC2 promoter.

* * * * *

SEQUENCE LISTING

```
<160> NUMBER OF SEQ ID NOS: 40

<210> SEQ ID NO 1
<211> LENGTH: 67
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Cys Cys Asn Arg Gly Lys Asn Val Ser Ile Glu Asn Leu His Gln
1               5                   10                  15

Gly Phe Thr His Ile Phe Glu Ser Thr Phe Glu Ser Thr Glu Gly Val
            20                  25                  30

Ala Glu Tyr Val Ser His Pro Ser His Val Glu Tyr Ala Asn Leu Phe
        35                  40                  45

Leu Ala Asn Leu Glu Lys Val Leu Val Ile Asp Tyr Lys Pro Thr Thr
    50                  55                  60

Val Arg Val
65


<210> SEQ ID NO 2
<211> LENGTH: 67
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 2

Met Cys Cys Asn Arg Gly Lys Asn Val Ser Ile Glu Asn Leu His Gln
1 5 10 15

Gly Phe Pro His Leu Phe Glu Phe Thr Phe Glu Ser Thr Glu Gly Val
20 25 30

Ala Glu Tyr Val Ser His Pro Ala His Val Glu Tyr Ala Asn Leu Phe
35 40 45

Leu Ala Asn Leu Glu Lys Val Leu Val Ile Asp Tyr Lys Pro Thr Thr
50 55 60

Val Arg Val
65

<210> SEQ ID NO 3
<211> LENGTH: 67
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 3

Met Cys Cys Asn Arg Gly Lys Asn Val Ser Ile Glu Asn Leu His Gln
1 5 10 15

Gly Phe Thr His Ile Phe Glu Ser Thr Phe Glu Ser Thr Glu Gly Val
20 25 30

Ala Glu Tyr Val Ala His Pro Ala His Val Glu Tyr Ala Asn Leu Phe
35 40 45

Leu Ala Asn Leu Glu Lys Val Leu Val Ile Asp Tyr Lys Pro Thr Thr
50 55 60

Glu Arg Val
65

<210> SEQ ID NO 4
<211> LENGTH: 67
<212> TYPE: PRT
<213> ORGANISM: Citrus sinensis

<400> SEQUENCE: 4

Met Cys Cys Asn Arg Gly Lys Asn Val Ser Ile Glu Asn Leu His Gln
1 5 10 15

Gly Phe Thr His Ile Phe Glu Ser Thr Phe Glu Ser Thr Glu Gly Val
20 25 30

Ala Glu Tyr Val Ala His Pro Ala His Val Glu Tyr Ala Asn Leu Phe
35 40 45

Leu Ala Asn Leu Glu Lys Val Leu Val Ile Asp Tyr Lys Pro Thr Thr
50 55 60

Val Arg Val
65

<210> SEQ ID NO 5
<211> LENGTH: 82
<212> TYPE: PRT
<213> ORGANISM: Citrus sinensis

<400> SEQUENCE: 5

Met Ile Ala Glu Leu Ile Arg Ser Cys Cys Gly Leu Glu Leu Leu Ala
1 5 10 15

Val Lys Tyr Lys Gly Lys Asn Val Ser Ile Glu Asn Leu His Gln Gly

```
            20                  25                  30

Phe Thr His Ile Phe Glu Ser Thr Phe Glu Ser Thr Glu Gly Val Ala
        35                  40                  45

Glu Tyr Val Ala His Pro Ala His Val Glu Tyr Ala Asn Leu Phe Leu
    50                  55                  60

Ala Asn Leu Glu Lys Val Leu Val Ile Asp Tyr Lys Pro Thr Thr Val
65                  70                  75                  80

Arg Val


<210> SEQ ID NO 6
<211> LENGTH: 109
<212> TYPE: PRT
<213> ORGANISM: Citrus sinensis

<400> SEQUENCE: 6

Met Glu Glu Ala Lys Gly Val Val Lys His Val Leu Leu Ala Lys Phe
1               5                   10                  15

Lys Glu Gly Thr Ala Gln Asp Gln Ile Asp Gln Leu Ile Lys Asp Tyr
            20                  25                  30

Ala Asn Leu Val Asn Leu Ile Glu Pro Met Lys Ser Phe Gln Trp Gly
        35                  40                  45

Lys Asp Val Ser Ile Glu Asn Arg His Gln Gly Phe Thr His Ile Phe
    50                  55                  60

Glu Ser Thr Phe Glu Ser Thr Glu Gly Val Ala Glu Tyr Val Ala His
65                  70                  75                  80

Pro Ala His Val Glu Tyr Ala Asn Leu Phe Leu Ala Asn Leu Glu Lys
                85                  90                  95

Val Leu Val Ile Asp Tyr Lys Pro Thr Thr Val Arg Val
            100                 105


<210> SEQ ID NO 7
<211> LENGTH: 114
<212> TYPE: PRT
<213> ORGANISM: Citrus sinensis

<400> SEQUENCE: 7

Met Gly Glu Gly Glu Glu Ala Ala Met Gly Glu Phe Lys His Leu Val
1               5                   10                  15

Ile Val Lys Phe Lys Glu Gly Val Val Val Glu Asp Ile Val Lys Gly
            20                  25                  30

Met Lys Lys Leu Val Ser Glu Ile Asp Ala Val Lys Ser Phe Glu Trp
        35                  40                  45

Gly Gln Asp Val Glu Gly Gln Glu Met Leu Arg Gln Gly Phe Thr His
    50                  55                  60

Ala Phe Leu Met Thr Phe Asn Lys Lys Glu Asp Tyr Thr Thr Phe Ala
65                  70                  75                  80

Ser His Pro Ser His Val Glu Phe Ser Ala Thr Phe Ser Ala Ala Ile
                85                  90                  95

Glu Lys Ile Val Leu Leu Asp Phe Pro Thr Val Leu Gly Lys Ala Pro
            100                 105                 110

Ala Ala


<210> SEQ ID NO 8
<211> LENGTH: 118
<212> TYPE: PRT
<213> ORGANISM: Citrus clementina
```

<400> SEQUENCE: 8

Met Lys Ala Glu Thr Lys Gly Arg Asp Met Glu Glu Ala Lys Gly Val
1               5                   10                  15

Val Lys His Val Leu Leu Ala Lys Phe Lys Glu Gly Thr Ala Gln Asp
            20                  25                  30

Gln Ile Asp Gln Leu Ile Lys Asp Tyr Ala Asn Leu Val Asn Leu Ile
        35                  40                  45

Glu Pro Met Lys Ser Phe Gln Trp Gly Lys Asp Val Ser Ile Glu Asn
    50                  55                  60

Leu His Gln Gly Phe Thr His Ile Phe Glu Ser Thr Phe Glu Ser Thr
65                  70                  75                  80

Glu Gly Val Ala Glu Tyr Val Ala His Pro Ala His Val Glu Tyr Ala
                85                  90                  95

Asn Leu Phe Leu Ala Asn Leu Glu Lys Val Leu Val Ile Asp Tyr Lys
            100                 105                 110

Pro Thr Thr Val Arg Val
        115

<210> SEQ ID NO 9
<211> LENGTH: 67
<212> TYPE: PRT
<213> ORGANISM: Capsicum annuum

<400> SEQUENCE: 9

Met Ser Tyr Gly Arg Gly Lys Asp Val Ser Thr Glu Asn Leu Gln Gln
1               5                   10                  15

Gly Phe Thr His Val Phe Glu Ser Thr Phe Asp Ser Thr Glu Gly Val
            20                  25                  30

Ala Glu Tyr Val Ser His Pro Val His Val Glu Phe Ala Asn Leu Met
        35                  40                  45

Leu Pro Gln Leu Glu Lys Val Leu Val Ile Asp Tyr Lys Pro Glu Lys
    50                  55                  60

Val Gly Pro
65

<210> SEQ ID NO 10
<211> LENGTH: 107
<212> TYPE: PRT
<213> ORGANISM: Nicotiana benthamiana

<400> SEQUENCE: 10

Met Glu Gly Gly Lys Val Lys His Ile Leu Leu Ala Lys Phe Lys Asp
1               5                   10                  15

Gly Ile Pro Ala Asp Gln Ile Asp Gln Leu Ile Lys Gln Tyr Ala Asn
            20                  25                  30

Leu Val Asn Leu Ile Glu Pro Met Lys Ala Phe His Trp Gly Glu Asn
        35                  40                  45

Val Ser Ile Glu Asn Phe His Gln Gly Phe Thr His Val Phe Glu Ser
    50                  55                  60

Thr Phe Asp Ser Thr Glu Gly Ile Ala Glu Tyr Ile Asp His Pro Ala
65                  70                  75                  80

His Val Glu Tyr Ala Asn Thr Leu Leu Pro Gln Leu Glu Lys Val Leu
                85                  90                  95

Val Ile Asp Tyr Lys Pro Glu Lys Val Gly Pro
            100                 105

```
<210> SEQ ID NO 11
<211> LENGTH: 106
<212> TYPE: PRT
<213> ORGANISM: Solanum lycopersicum

<400> SEQUENCE: 11

Met Glu Gly Gly Lys Gly Gly Val Val Lys His Ile Leu Leu Ala Lys
1               5                   10                  15

Phe Lys Asp Gly Ile Pro Pro Glu Gln Ile Asp Gln Leu Ile Lys Gln
            20                  25                  30

Tyr Ala Asn Leu Val Asn Leu Val Glu Pro Met Lys Ala Phe Gln Trp
        35                  40                  45

Gly Lys Asp Val Ser Ile Glu Asn Leu His Gln Gly Phe Thr His Val
    50                  55                  60

Phe Glu Ser Thr Phe Asp Ser Leu Glu Gly Val Ala Glu Tyr Ile Ala
65                  70                  75                  80

His Pro Val His Val Glu Tyr Ala Asn Thr Leu Leu Pro Gln Leu Glu
                85                  90                  95

Lys Phe Leu Ile Val Asp Tyr Lys Pro Gln
            100                 105


<210> SEQ ID NO 12
<211> LENGTH: 116
<212> TYPE: PRT
<213> ORGANISM: Solanum melongena

<400> SEQUENCE: 12

Met Asn Ile Ala Val Phe Leu Pro Ser Ser Cys Pro Ala Leu Pro Arg
1               5                   10                  15

Ser Lys Ala Ser Arg Pro Ser Pro Pro Gly Gln Phe Pro Phe Leu Ala
            20                  25                  30

Lys Asn Val Gln Leu Leu Leu Val Leu Arg Ser Tyr Ser Ser Thr Ala
        35                  40                  45

Arg Ala Met Ser Leu Arg Gly Glu Asn Val Ser Ile Glu Asn Leu His
    50                  55                  60

Gln Gly Phe Thr His Val Phe Glu Ser Thr Phe Asp Ser Val Glu Gly
65                  70                  75                  80

Ile Ala Glu Tyr Ile Asp His Pro Ala His Val Glu Tyr Ala Asn Ile
                85                  90                  95

Leu Leu Thr Gln Leu Glu Lys Val Leu Val Ile Asp Tyr Lys Pro Glu
            100                 105                 110

Lys Leu Ser Pro
        115


<210> SEQ ID NO 13
<211> LENGTH: 106
<212> TYPE: PRT
<213> ORGANISM: Solanum tuberosum

<400> SEQUENCE: 13

Met Glu Gly Gly Lys Gly Gly Val Val Lys His Ile Leu Leu Ala Lys
1               5                   10                  15

Phe Lys Asp Gly Ile Pro Pro Glu Gln Ile Asp Gln Leu Ile Lys Gln
            20                  25                  30

Tyr Ala Asn Leu Val Asn Leu Ile Glu Pro Met Lys Ala Phe Gln Trp
        35                  40                  45

Gly Lys Asp Val Ser Ile Glu Asn Leu His Gln Gly Phe Thr His Val
    50                  55                  60
```

-continued

```
Phe Glu Ser Thr Phe Asp Ser Leu Glu Gly Val Ala Glu Tyr Ile Ala
65                  70                  75                  80

His Pro Val His Val Glu Phe Ala Asn Thr Met Leu Pro Gln Leu Glu
                85                  90                  95

Lys Val Leu Ile Ile Asp Tyr Lys Pro Gln
            100                 105


<210> SEQ ID NO 14
<211> LENGTH: 259
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14

atgtgctgca acaggggcaa gaatgtgagc attgagaatc ttcatcaggg tttcactcat      60

atttttgaat ctacctttga gagcacagag ggtgttgcag agtatgtatc tcatccgtca     120

catgttgaat acgcaaactt gttcctggcc aacttggaga aagttctcgt gattgactac     180

aaaccgacaa cagtacgtgt ctgagaaggg tgggcgcgcc gacccagctt tcttgtacaa     240

agttggcatt ataagaaag                                                  259


<210> SEQ ID NO 15
<211> LENGTH: 234
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15

atgtgctgca acaggggcaa gaatgtgagc attgagaatc ttcatcaggg tttccctcat      60

cttttcgaat ttacctttga gagcacagag ggtgttgcag agtatgtatc tcatccggca     120

catgttgaat acgcaaactt gttcctggcc aacttggaga aagttctcgt gattgactac     180

aaaccgacaa cagtacgtgt ctgagaaggg tgggcgcgcc gacccagctt tctt           234


<210> SEQ ID NO 16
<211> LENGTH: 237
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16

atgtgctgca acaggggcaa gaatgtgagc attgagaatc ttcatcaggg tttcactcat      60

atttttgaat ctacctttga gagcacagag ggtgttgcag agtatgtagc tcatccggca     120

catgttgaat acgcaaactt gttcctggcc aacttggaga aagttctcgt gattgactac     180

aaaccgacaa cagaacgtgt ctaagggtgg gcgcgccgac ccagctttct tgtacaa        237


<210> SEQ ID NO 17
<211> LENGTH: 221
<212> TYPE: DNA
<213> ORGANISM: Citrus sinensis

<400> SEQUENCE: 17

atgtgctgca acaggggcaa gaatgtgagc attgagaatc ttcatcaggg tttcactcat      60
```

-continued atttttgaat ctacctttga gagcacagag ggtgttgcag agtatgtagc tcatccggca 120
catgttgaat acgcaaactt gttcctggcc aacttggaga aagttctcgt gattgactac 180
aaaccgacaa cagtacgtgt ctgagttgta ctagtaggga a 221

<210> SEQ ID NO 18
<211> LENGTH: 330
<212> TYPE: DNA
<213> ORGANISM: Citrus sinensis

<400> SEQUENCE: 18
atggaagaag ctaaaggagt ggtgaagcac gtacttctgg ccaagttcaa agaagggact 60
gctcaagatc aaattgatca gctcatcaaa gactatgcaa atcttgtgaa tctcattgaa 120
cccatgaagt ctttccaatg ggcaagaat gtgagcattg agaatcttca tcagggtttc 180
actcatattt ttgaatctac ctttgagagc acagagggtg ttgcagagta tgtagctcat 240
ccggcacatg ttgaatacgc aaacttgttc ctggccaact tggagaaagt tctcgtgatt 300
gactacaaac cgacaacagt acgtgtctga 330

<210> SEQ ID NO 19
<211> LENGTH: 330
<212> TYPE: DNA
<213> ORGANISM: Citrus sinensis

<400> SEQUENCE: 19
atggaagaag ctaaaggagt ggtgaagcac gtacttctgg ccaagttcaa agaagggact 60
gctcaagatc aaattgatca gctcatcaaa gactatgcaa atcttgtgaa tctcattgaa 120
cccatgaagt ctttccaatg ggcaagaat gtgagcattg agaatcttca tcagggtttc 180
actcatattt ttgaatctac ctttgagagc acagagggtg ttgcagagta tgtagctcat 240
ccggcacatg ttgaatacgc aaacttgttc ctggccaact tggagaaagt tctcgtgatt 300
gactacaaac cgacaacagt acgtgtctga 330

<210> SEQ ID NO 20
<211> LENGTH: 345
<212> TYPE: DNA
<213> ORGANISM: Citrus sinensis

<400> SEQUENCE: 20
atgggtgagg gtgaagaggc agcaatggga gagttcaagc acttggtgat tgttaagttc 60
aaggaaggtg tggttgtgga ggatattgtc aaagggatga aaaagctggt ttcagagatt 120
gatgctgtca aatcttttga atggggccaa gatgtagaag ggcaggagat gcttaggcaa 180
ggcttcacac atgcattctt gatgacattc aacaagaagg aagactatac aacctttgca 240
agccatccca gccacgtcga attctcggct acattttcag ctgctattga gaagattgtc 300
ctgcttgatt tccctaccgt gcttggcaaa gcaccagcag catga 345

<210> SEQ ID NO 21
<211> LENGTH: 357
<212> TYPE: DNA
<213> ORGANISM: Citrus clementina

<400> SEQUENCE: 21
atgaaagccg aaacaaaagg cagagatatg gaagaagcta aaggagtggt gaagcacgta 60
cttctggcca agttcaaaga agggactgct caagatcaaa ttgatcagct catcaaagac 120
tatgcaaatc ttgtgaatct cattgaaccc atgaagtctt tccaatgggg caaggatgtg 180
agcattgaga atcttcatca gggtttcact catatttttg aatctacctt tgagagcaca 240
gagggtgttg cagagtatgt agctcatccg gcacatgttg aatacgcaaa cttgttcctg 300
gccaacttgg agaaagttct cgtgattgac tacaaaccga caactgtacg tgtctga 357

<210> SEQ ID NO 22
<211> LENGTH: 204
<212> TYPE: DNA
<213> ORGANISM: Capsicum annuum

<400> SEQUENCE: 22
atgtcatatg gcaggggtaa ggatgtgagc acagagaacc tccagcaagg tttcactcat 60
gtttttgagt caacgttcga cagtacagaa ggtgttgcag agtatgtaag tcatccggtt 120
catgttgaat ttgcaaatct aatgcttcct cagctggaga aagtcctcgt catcgactac 180
aaaccggaga aagtcggtcc ctaa 204

<210> SEQ ID NO 23
<211> LENGTH: 321
<212> TYPE: DNA
<213> ORGANISM: Nicotiana benthamiana

<400> SEQUENCE: 23
atggagggtg gtaaagtgaa gcacatattg ctggccaagt tcaaagatgg aattccagca 60
gaccaaatcg accaactgat taagcaatat gctaatcttg tcaatctcat cgaaccaatg 120
aaagcttttc attggggtga gaatgtgagc atagagaact tccaccaagg tttcactcat 180
gtttttgagt caacgttcga cagtacagaa ggaattgcag agtatataga tcatccggct 240
catgttgaat atgcaaatac attgcttcct cagctggaga aagtccttgt catcgactac 300
aaaccagaga aagttggtcc c 321

<210> SEQ ID NO 24
<211> LENGTH: 318
<212> TYPE: DNA
<213> ORGANISM: Solanum lycopersicum

<400> SEQUENCE: 24
atggagggtg gcaaaggagg agttgtgaag cacattttgc tagcaaagtt caaagatggg 60
atcccacctg aacagattga tcaactcatt aagcagtatg ctaatcttgt caatcttgtt 120
gaacccatga aggcttttca atggggtaag gatgtgagca tagaaaatct tcatcaaggt 180
ttcactcatg ttttcgagtc tacgtttgac agtttagaag gtgttgcaga gtatatagct 240
catcctgttc atgttgaata tgcaaataca ttgcttcctc agctggagaa attccttatc 300
gtcgactaca aaccacag 318

<210> SEQ ID NO 25
<211> LENGTH: 351
<212> TYPE: DNA
<213> ORGANISM: Solanum melongena

<400> SEQUENCE: 25
atgaatattg ctgtctttct cccttcgtcc tgccctgccc tgccccgctc aaaggcttcc 60
cgcccatccc cacccggcca atttccgttc ctagccaaga atgttcagct tctactagtc 120
ttgaggtctt atagttccac cgctcgtgct atgtcactta ggggtgagaa tgtgagcata 180
gagaacctcc accaaggttt cactcacgtt ttcgagtcaa cgtttgacag tgtagaaggc 240

```
attgcagagt atatagatca tcctgctcat gttgaatatg caaatatatt gcttactcag    300

ctggagaaag tccttgtcat cgactacaaa ccagagaaac tcagccccta a             351
```

<210> SEQ ID NO 26
<211> LENGTH: 696
<212> TYPE: DNA
<213> ORGANISM: Solanum tuberosum

<400> SEQUENCE: 26

```
ctcatacaat caaccaaata aaggaccctt ttctctccac tatttttgct tgtctagtca     60

aggaagaaga gtgataaaat agaaatggag ggtggtaaag gaggagtggt gaagcacatt    120

ttgctagcaa agttcaaaga tgggatccca cctgaacaaa ttgatcaact cattaagcag    180

tatgctaatc ttgtcaatct tattgaaccc atgaaggctt ttcaatgggg caaggatgtg    240

agcatagaaa accttcacca aggtttcact catgtttttg agtcgacgtt tgacagttta    300

gaaggcgttg cagagtatat agctcatcct gttcatgttg aatttgcaaa tacaatgctt    360

cctcagctgg agaaagtcct tatcattgac tacaaaccac agtaactcag tccctaaact    420

ggattcacaa attgatgcac ttgatgtaat aggtatatca gttttacttt actgtactga    480

aatccaataa gaacacaaac ttttattaag ggtgtgtgtc ttgcttgttt gcaattattg    540

tattcacttc gtagacgcta atgcgagtaa cttatggtca gcttgggctg tttaaactcg    600

aggaagaatg ctcttcgttc ttctcttccc agggagaatg aatgatgaac aacatataag    660

tgcatcaata aactcagatt ggtgtttcca tttcct                              696
```

<210> SEQ ID NO 27
<211> LENGTH: 63
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(1)
<223> OTHER INFORMATION: Arg, Lys, or Trp
<220> FEATURE:
<221> NAME/KEY: MOD_RES
<222> LOCATION: (3)..(3)
<223> OTHER INFORMATION: Lys or Glu
<220> FEATURE:
<221> NAME/KEY: MOD_RES
<222> LOCATION: (4)..(4)
<223> OTHER INFORMATION: Asn or Asp
<220> FEATURE:
<221> NAME/KEY: MOD_RES
<222> LOCATION: (7)..(7)
<223> OTHER INFORMATION: Thr or Ile
<220> FEATURE:
<221> NAME/KEY: MOD_RES
<222> LOCATION: (10)..(10)
<223> OTHER INFORMATION: Leu, Phe or Arg
<220> FEATURE:
<221> NAME/KEY: MOD_RES
<222> LOCATION: (11)..(11)
<223> OTHER INFORMATION: His or Gln
<220> FEATURE:
<221> NAME/KEY: MOD_RES
<222> LOCATION: (15)..(15)
<223> OTHER INFORMATION: Pro or Thr
<220> FEATURE:
<221> NAME/KEY: MOD_RES
<222> LOCATION: (17)..(17)
<223> OTHER INFORMATION: Ile, Leu or Val
<220> FEATURE:
<221> NAME/KEY: MOD_RES
<222> LOCATION: (20)..(20)

<223> OTHER INFORMATION: Ser or Phe
<220> FEATURE:
<221> NAME/KEY: MOD_RES
<222> LOCATION: (23)..(23)
<223> OTHER INFORMATION: Glu or Asp
<220> FEATURE:
<221> NAME/KEY: MOD_RES
<222> LOCATION: (25)..(25)
<223> OTHER INFORMATION: Thr or Leu
<220> FEATURE:
<221> NAME/KEY: MOD_RES
<222> LOCATION: (28)..(28)
<223> OTHER INFORMATION: Val or Ile
<220> FEATURE:
<221> NAME/KEY: MOD_RES
<222> LOCATION: (32)..(32)
<223> OTHER INFORMATION: Val or Ile
<220> FEATURE:
<221> NAME/KEY: MOD_RES
<222> LOCATION: (33)..(33)
<223> OTHER INFORMATION: Ser, Ala or Asp
<220> FEATURE:
<221> NAME/KEY: MOD_RES
<222> LOCATION: (36)..(36)
<223> OTHER INFORMATION: Ser, Ala or Val
<220> FEATURE:
<221> NAME/KEY: MOD_RES
<222> LOCATION: (40)..(40)
<223> OTHER INFORMATION: Tyr or Phe
<220> FEATURE:
<221> NAME/KEY: MOD_RES
<222> LOCATION: (43)..(43)
<223> OTHER INFORMATION: Leu or Thr
<220> FEATURE:
<221> NAME/KEY: MOD_RES
<222> LOCATION: (44)..(44)
<223> OTHER INFORMATION: Phe, Met or Leu
<220> FEATURE:
<221> NAME/KEY: MOD_RES
<222> LOCATION: (46)..(46)
<223> OTHER INFORMATION: Ala, Pro or Thr
<220> FEATURE:
<221> NAME/KEY: MOD_RES
<222> LOCATION: (47)..(47)
<223> OTHER INFORMATION: Asn or Gln
<220> FEATURE:
<221> NAME/KEY: MOD_RES
<222> LOCATION: (51)..(51)
<223> OTHER INFORMATION: Val or Phe
<220> FEATURE:
<221> NAME/KEY: MOD_RES
<222> LOCATION: (53)..(54)
<223> OTHER INFORMATION: Val or Ile
<220> FEATURE:
<221> NAME/KEY: MOD_RES
<222> LOCATION: (59)..(59)
<223> OTHER INFORMATION: Thr, Glu or Gln
<220> FEATURE:
<221> NAME/KEY: MOD_RES
<222> LOCATION: (61)..(61)
<223> OTHER INFORMATION: Val, Glu or Leu

<400> SEQUENCE: 27

```
Xaa Gly Xaa Xaa Val Ser Xaa Glu Asn Xaa Xaa Gln Gly Phe Xaa His
1               5                   10                  15

Xaa Phe Glu Xaa Thr Phe Xaa Ser Xaa Glu Gly Xaa Ala Glu Tyr Xaa
            20                  25                  30

Xaa His Pro Xaa His Val Glu Xaa Ala Asn Xaa Xaa Leu Xaa Xaa Leu
        35                  40                  45

Glu Lys Xaa Leu Xaa Xaa Asp Tyr Lys Pro Xaa Thr Xaa Arg Val
    50                  55                  60
```

<210> SEQ ID NO 28
<211> LENGTH: 204

<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 28
atgtgctgca acaggggcaa gaatgtgagc attgagaatc ttcatcaggg tttcactcat 60
atttttgaat ctacctttga gagcacagag ggtgttgcag agtatgtatc tcatccgtca 120
catgttgaat acgcaaactt gttcctggcc aacttggaga aagttctcgt gattgactac 180
aaaccgacaa cagtacgtgt ctga 204

<210> SEQ ID NO 29
<211> LENGTH: 204
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 29
atgtgctgca acaggggcaa gaatgtgagc attgagaatc ttcatcaggg tttccctcat 60
cttttcgaat ttacctttga gagcacagag ggtgttgcag agtatgtatc tcatccggca 120
catgttgaat acgcaaactt gttcctggcc aacttggaga aagttctcgt gattgactac 180
aaaccgacaa cagtacgtgt ctga 204

<210> SEQ ID NO 30
<211> LENGTH: 204
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 30
atgtgctgca acaggggcaa gaatgtgagc attgagaatc ttcatcaggg tttcactcat 60
atttttgaat ctacctttga gagcacagag ggtgttgcag agtatgtagc tcatccggca 120
catgttgaat acgcaaactt gttcctggcc aacttggaga aagttctcgt gattgactac 180
aaaccgacaa cagaacgtgt ctaa 204

<210> SEQ ID NO 31
<211> LENGTH: 204
<212> TYPE: DNA
<213> ORGANISM: Citrus sinensis

<400> SEQUENCE: 31
atgtgctgca acaggggcaa gaatgtgagc attgagaatc ttcatcaggg tttcactcat 60
atttttgaat ctacctttga gagcacagag ggtgttgcag agtatgtagc tcatccggca 120
catgttgaat acgcaaactt gttcctggcc aacttggaga aagttctcgt gattgactac 180
aaaccgacaa cagtacgtgt ctga 204

<210> SEQ ID NO 32
<211> LENGTH: 324
<212> TYPE: DNA
<213> ORGANISM: Nicotiana benthamiana

<400> SEQUENCE: 32
atggagggtg gtaaagtgaa gcacatattg ctggccaagt tcaaagatgg aattccagca 60
gaccaaatcg accaactgat taagcaatat gctaatcttg tcaatctcat cgaaccaatg 120
aaagcttttc attggggtga gaatgtgagc atagagaact tccaccaagg tttcactcat 180
gtttttgagt caacgttcga cagtacagaa ggaattgcag agtatataga tcatccggct 240
catgttgaat atgcaaatac attgcttcct cagctggaga aagtccttgt catcgactac 300
aaaccagaga aagttggtcc ctaa 324

<210> SEQ ID NO 33
<211> LENGTH: 321
<212> TYPE: DNA
<213> ORGANISM: Solanum lycopersicum

<400> SEQUENCE: 33
atggagggtg gcaaaggagg agttgtgaag cacattttgc tagcaaagtt caaagatggg 60
atcccacctg aacagattga tcaactcatt aagcagtatg ctaatcttgt caatcttgtt 120
gaacccatga aggcttttca atggggtaag gatgtgagca tagaaaatct tcatcaaggt 180
ttcactcatg ttttcgagtc tacgtttgac agtttagaag gtgttgcaga gtatatagct 240
catcctgttc atgttgaata tgcaaataca ttgcttcctc agctggagaa attccttatc 300
gtcgactaca aaccacagta a 321

<210> SEQ ID NO 34
<211> LENGTH: 321
<212> TYPE: DNA
<213> ORGANISM: Solanum tuberosum

<400> SEQUENCE: 34
atggagggtg gtaaaggagg agtggtgaag cacattttgc tagcaaagtt caaagatggg 60
atcccacctg aacaaattga tcaactcatt aagcagtatg ctaatcttgt caatcttatt 120
gaacccatga aggcttttca atggggcaag gatgtgagca tagaaaacct tcaccaaggt 180
ttcactcatg tttttgagtc gacgtttgac agtttagaag gcgttgcaga gtatatagct 240
catcctgttc atgttgaatt tgcaaataca atgcttcctc agctggagaa agtccttatc 300
attgactaca aaccacagta a 321

<210> SEQ ID NO 35
<211> LENGTH: 67
<212> TYPE: PRT
<213> ORGANISM: Poncirus trifoliata

<400> SEQUENCE: 35

Met Cys Cys Asn Arg Gly Lys Asn Val Ser Ile Glu Asn Leu His Gln
1 5 10 15

Gly Phe Thr His Ile Phe Glu Ser Thr Phe Glu Ser Thr Glu Gly Val
20 25 30

Ala Glu Tyr Val Ala His Pro Ala His Val Glu Tyr Ala Asn Ser Phe
35 40 45

Leu Ala Asn Leu Glu Lys Val Leu Val Ile Asp Tyr Lys Pro Thr Thr
50 55 60

Val Arg Val
65

<210> SEQ ID NO 36
<211> LENGTH: 67
<212> TYPE: PRT
<213> ORGANISM: Poncirus trifoliata

<400> SEQUENCE: 36

Met Cys Cys Asn Arg Gly Lys Asn Val Ser Ile Glu Asn Leu His Gln
1               5                   10                  15

Gly Phe Thr His Ile Phe Glu Ser Thr Phe Glu Ser Thr Glu Gly Val
            20                  25                  30

Ala Glu Tyr Val Ala His Pro Ala His Val Glu Tyr Thr Asn Ser Phe
        35                  40                  45

Leu Ala Asn Leu Glu Lys Val Leu Val Ile Asp Tyr Lys Pro Thr Thr
    50                  55                  60

Val Arg Val
65

<210> SEQ ID NO 37
<211> LENGTH: 67
<212> TYPE: PRT
<213> ORGANISM: Unknown
<220> FEATURE:
<223> OTHER INFORMATION: Description of Unknown:
      Microcitrus australasica or Poncirus trifoliata SAMP

<400> SEQUENCE: 37

Met Cys Cys Asn Arg Gly Lys Asn Val Ser Ile Glu Asn Leu His Gln
1               5                   10                  15

Gly Phe Thr His Ile Phe Glu Ser Thr Phe Glu Ser Thr Glu Gly Val
            20                  25                  30

Ala Glu Tyr Val Ser His Pro Ala His Val Glu Tyr Ala Asn Leu Phe
        35                  40                  45

Leu Ala Asn Leu Glu Lys Val Leu Val Ile Asp Tyr Lys Pro Thr Thr
    50                  55                  60

Val Arg Val
65

<210> SEQ ID NO 38
<211> LENGTH: 204
<212> TYPE: DNA
<213> ORGANISM: Poncirus trifoliata

<400> SEQUENCE: 38
atgtgctgca acaggggcaa gaatgtgagc attgagaatc ttcatcaggg tttcactcat      60
atttttgaat ctacctttga gagcacagag ggtgttgcag agtatgtagc tcatccggca     120
catgttgaat acgcaaactc gttcctggcc aacttggaga aagttctcgt gattgactac     180
aaaccgacaa cagtacgtgt ctga                                            204

<210> SEQ ID NO 39
<211> LENGTH: 204
<212> TYPE: DNA
<213> ORGANISM: Poncirus trifoliata

<400> SEQUENCE: 39
atgtgctgca acaggggcaa gaatgtgagc attgagaatc ttcatcaggg tttcactcat      60
atttttgaat ctacctttga gagcacagag ggtgttgcag agtatgtagc tcatccggca     120
catgttgaat acacaaactc gttcctggcc aacttggaga aagttctcgt gattgactac     180
aaaccgacaa cagtacgtgt ctga                                            204

<210> SEQ ID NO 40
<211> LENGTH: 204

-continued

```
<212> TYPE: DNA
<213> ORGANISM: Microcitrus australasica

<400> SEQUENCE: 40

atgtgctgca acaggggcaa gaatgtgagt attgagaatc ttcatcaggg tttcactcat     60

atttttgaat ctacctttga gagcacagag ggtgttgcag agtatgtatc tcatccggca    120

catgttgaat acgcaaactt gttcctcgcc aacttggaga aagttctcgt gattgactac    180

aaaccgacaa cagtacgtgt ctga                                           204
```